US012672869B2

(12) United States Patent
Schings et al.

(10) Patent No.: US 12,672,869 B2
(45) Date of Patent: Jul. 7, 2026

(54) STAPLE CARTRIDGE IDENTIFICATION SYSTEMS

(71) Applicant: Cilag GmbH International, Zug (CH)

(72) Inventors: Brian D Schings, Cincinnati, OH (US); Zhifan F. Huang, Mason, OH (US)

(73) Assignee: Cilag GmbH International (CH)

( * ) Notice: Subject to any disclaimer, the term of this patent is extended or adjusted under 35 U.S.C. 154(b) by 0 days.

(21) Appl. No.: 18/814,945

(22) Filed: Aug. 26, 2024

(65) Prior Publication Data

US 2024/0415510 A1 Dec. 19, 2024

Related U.S. Application Data

(62) Division of application No. 17/513,697, filed on Oct. 28, 2021, now Pat. No. 12,089,841.

(51) Int. Cl.
| | |
|---|---|
| *A61B 17/072* | (2006.01) |
| *A61B 17/068* | (2006.01) |
| *A61B 90/98* | (2016.01) |

(52) U.S. Cl.
CPC ........ *A61B 17/0686* (2013.01); *A61B 17/072* (2013.01); *A61B 17/07207* (2013.01); *A61B 90/98* (2016.02); *A61B 2017/07214* (2013.01); *A61B 2017/07257* (2013.01); *A61B 2017/07271* (2013.01); *A61B 2017/07278* (2013.01); *A61B 2017/07285* (2013.01)

(58) Field of Classification Search
CPC . A61B 17/068; A61B 17/0686; A61B 17/072; A61B 17/07207; A61B 17/115; A61B 17/00234; A61B 2017/00477; A61B 2017/07214; A61B 2017/07256; A61B 2017/07271; A61B 2017/07285; A61B 90/98
USPC .............. 227/19, 175.1, 175.2, 176.1, 180.1; 606/1, 139, 153, 219
See application file for complete search history.

(56) References Cited

U.S. PATENT DOCUMENTS

| | | | | |
|---|---|---|---|---|
| 9,386,984 | B2 * | 7/2016 | Aronhalt | .......... A61B 17/07292 |
| 10,675,026 | B2 * | 6/2020 | Harris | ................ A61B 17/0682 |
| 2007/0119900 | A1 * | 5/2007 | Ehrenfels | ......... A61B 17/07207 |
| | | | | 227/176.1 |

(Continued)

OTHER PUBLICATIONS

PCT International Search Report dated Jan. 25, 2023.

*Primary Examiner* — Scott A Smith

(57) ABSTRACT

A surgical stapling system comprising an instrument interface comprising a control circuit and an RFID reader is disclosed. The surgical stapling system further comprises a shaft assembly comprising a shaft and an end effector. The end effector comprises a first jaw, a second jaw, an anvil, and a cartridge channel. The surgical stapling system further comprises a replaceable staple cartridge assembly removably positioned within the cartridge channel. The replaceable staple cartridge assembly comprises a cartridge body, a longitudinal slot, a plurality of staple cavities, a plurality of staples, and a staple cartridge retainer. The staple cartridge retainer comprises a rib, a body portion, and an RFID tag embedded within the body portion, wherein the RFID tag comprises a memory, wherein the memory comprises identifier information stored in the memory specific to the staple cartridge, and wherein the identifier information is accessible by the RFID reader.

11 Claims, 21 Drawing Sheets

(56) References Cited

U.S. PATENT DOCUMENTS

| | | | |
|---|---|---|---|
| 2008/0185419 A1* | 8/2008 | Smith ................... | A61B 17/115 |
| | | | 227/179.1 |
| 2014/0224856 A1* | 8/2014 | Smith ................... | A61B 17/115 |
| | | | 227/175.1 |
| 2015/0196348 A1* | 7/2015 | Yates ..................... | A61B 90/98 |
| | | | 227/182.1 |
| 2020/0261085 A1* | 8/2020 | Boudreaux .......... | A61B 17/072 |
| 2020/0405302 A1 | 12/2020 | Shelton, IV et al. | |
| 2020/0405303 A1* | 12/2020 | Shelton, IV ......... | A61B 17/115 |
| 2021/0401433 A1* | 12/2021 | Freidel ................. | A61B 17/072 |
| 2022/0133304 A1* | 5/2022 | Leimbach ........ | A61B 17/07207 |
| | | | 227/180.1 |
| 2023/0135282 A1* | 5/2023 | Schings ............. | A61B 17/0686 |
| | | | 227/180.1 |

* cited by examiner

STAPLE CARTRIDGE IDENTIFICATION SYSTEMS

The present application is a divisional of U.S. patent application Ser. No. 17/513,697 filed Oct. 28, 2021 now U.S. Pat. No. 12,089,841, and assigned to the assignee of the present application. The entire contents of U.S. patent application Ser. No. 17/513,697 are hereby explicitly incorporated by reference herein.

BACKGROUND

The present disclosure relates to surgical instruments, including surgical staplers configured to staple and cut tissue, which are usable as handheld instruments and/or as surgical tools connectable to surgical robots.

BRIEF DESCRIPTION OF THE FIGURES

The various aspects described herein, both as to organization and methods of operation, together with further objects and advantages thereof, may best be understood by reference to the following description, taken in conjunction with the accompanying drawings as follows.

Corresponding reference characters indicate corresponding parts throughout the several views. The exemplifications set out herein illustrate various embodiments of the invention, in one form, and such exemplifications are not to be construed as limiting the scope of the invention in any manner.

DESCRIPTION

Figure 1:
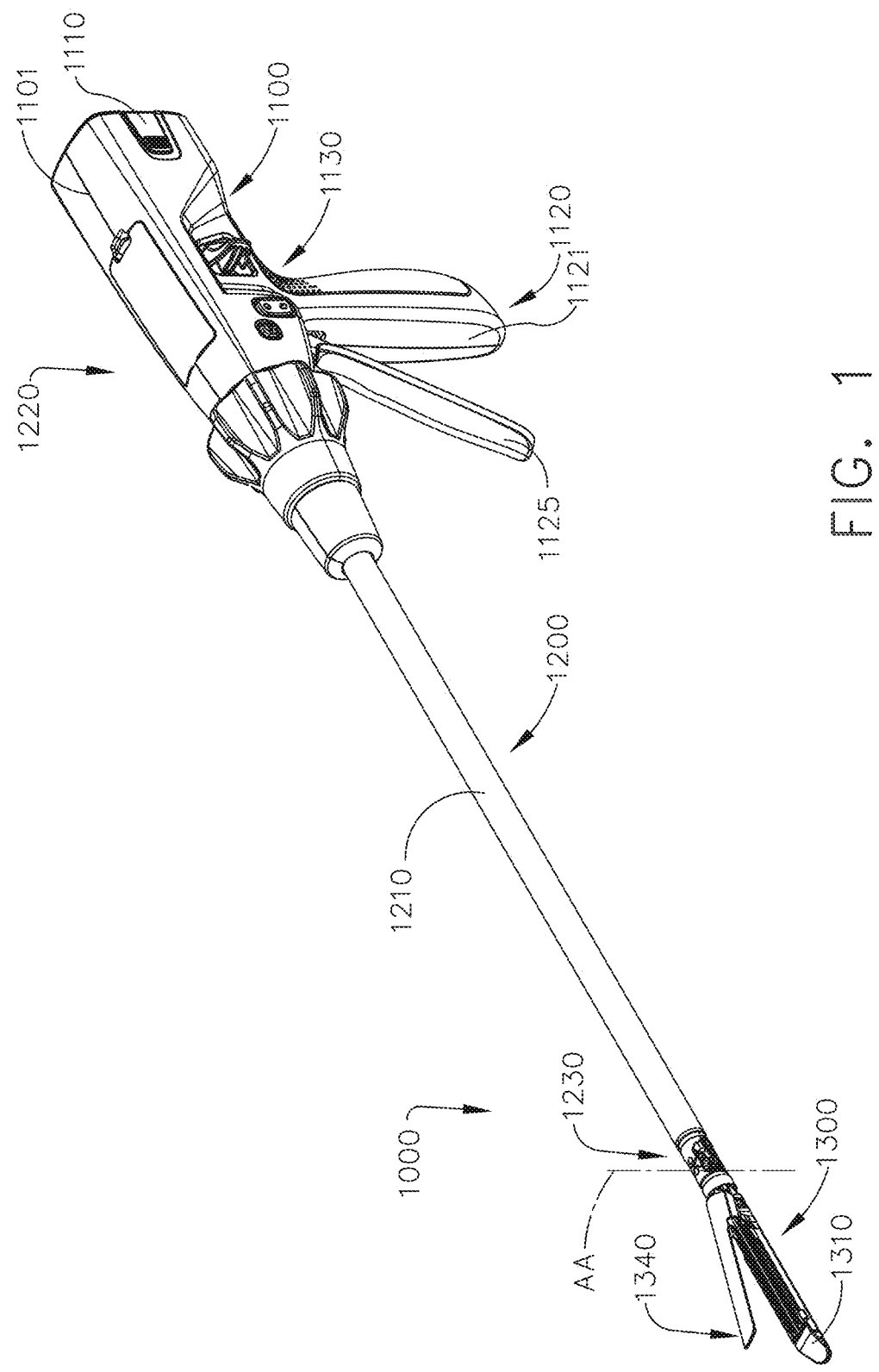
FIG. 1 is a perspective view of a surgical stapling instrument comprising a handle, a shaft assembly, and an end effector assembly.
Figure 2:
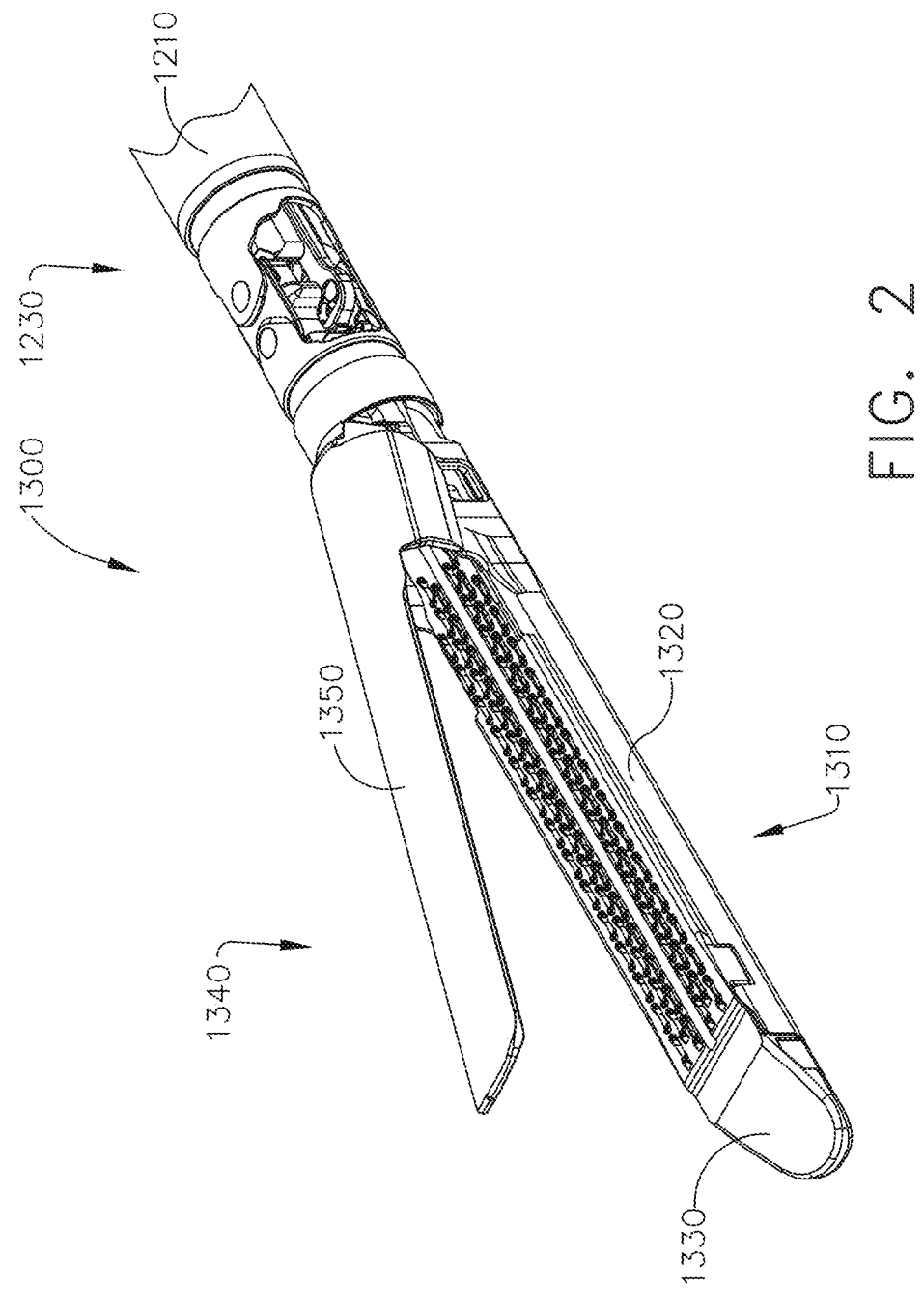
FIG. 2 is a perspective view of the end effector assembly of FIG. 1.
Figure 3:
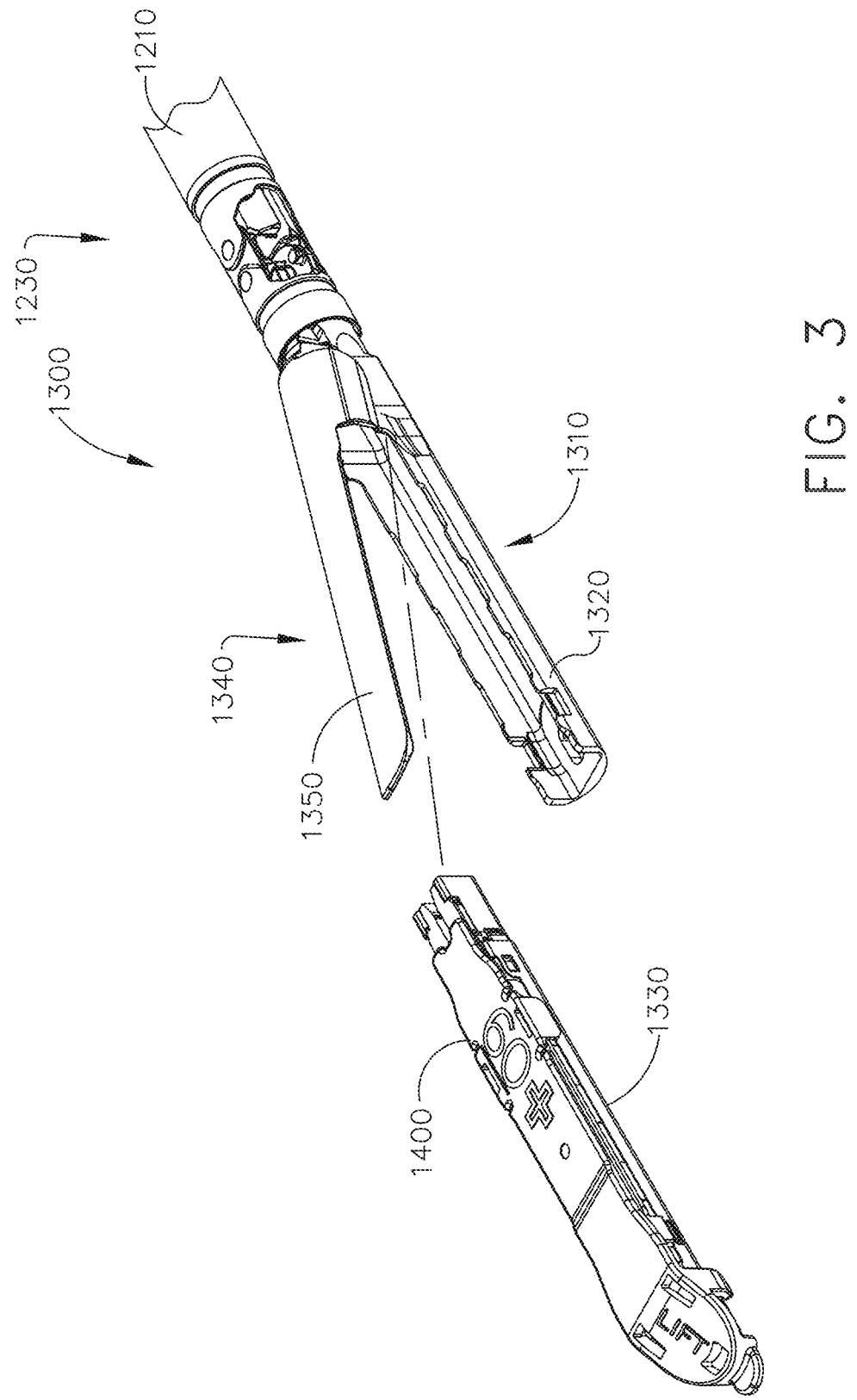
FIG. 3 is a perspective view of the end effector assembly of FIG. 1, wherein the end effector assembly comprises a staple cartridge assembly, and wherein the staple cartridge assembly comprises a retainer, and wherein the staple cartridge assembly is illustrated removed from a cartridge channel of the end effector assembly.
Figure 4:
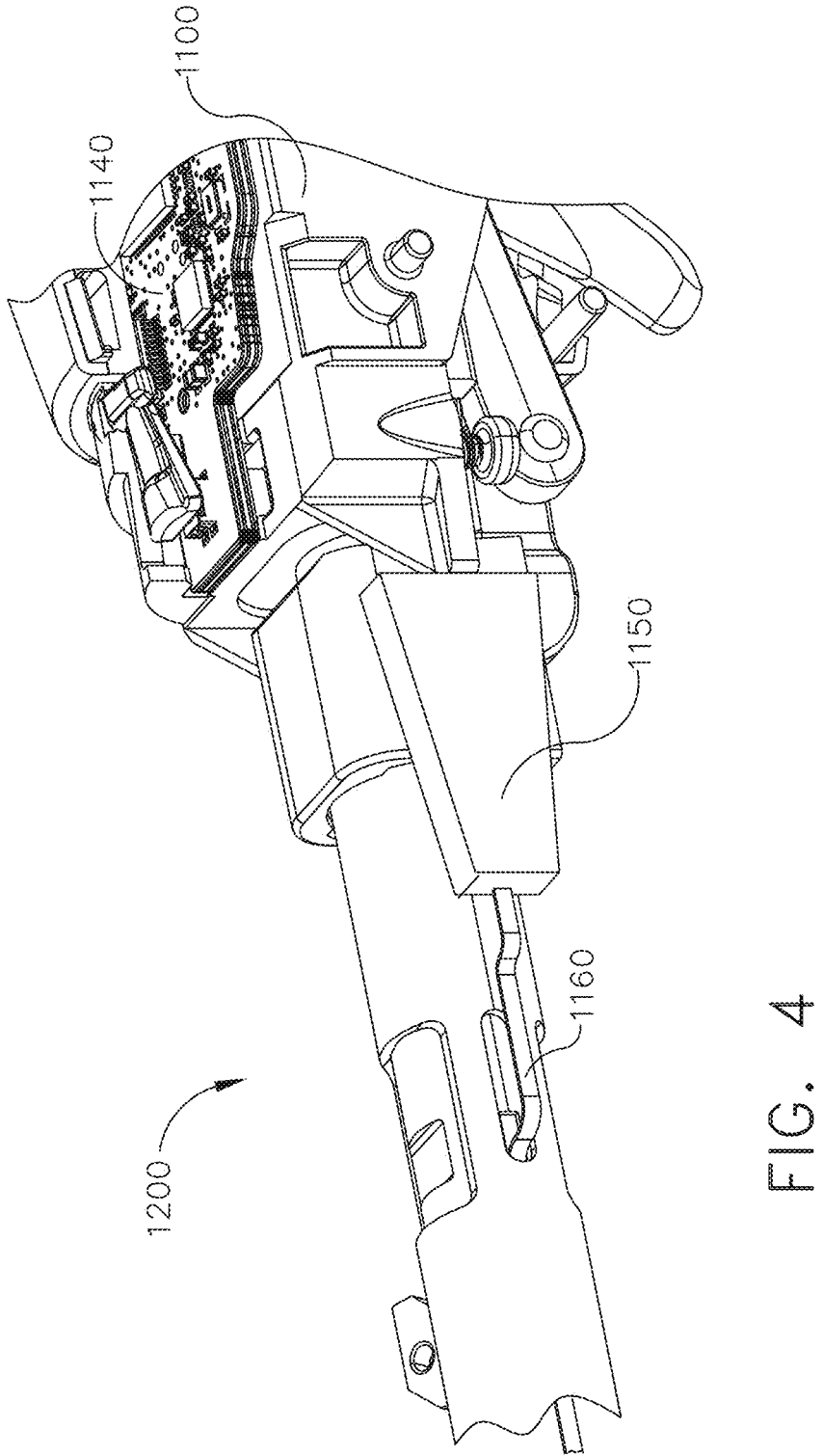
FIG. 4 is perspective view of a portion of the shaft assembly and the handle of FIG. 1.
Figure 5:
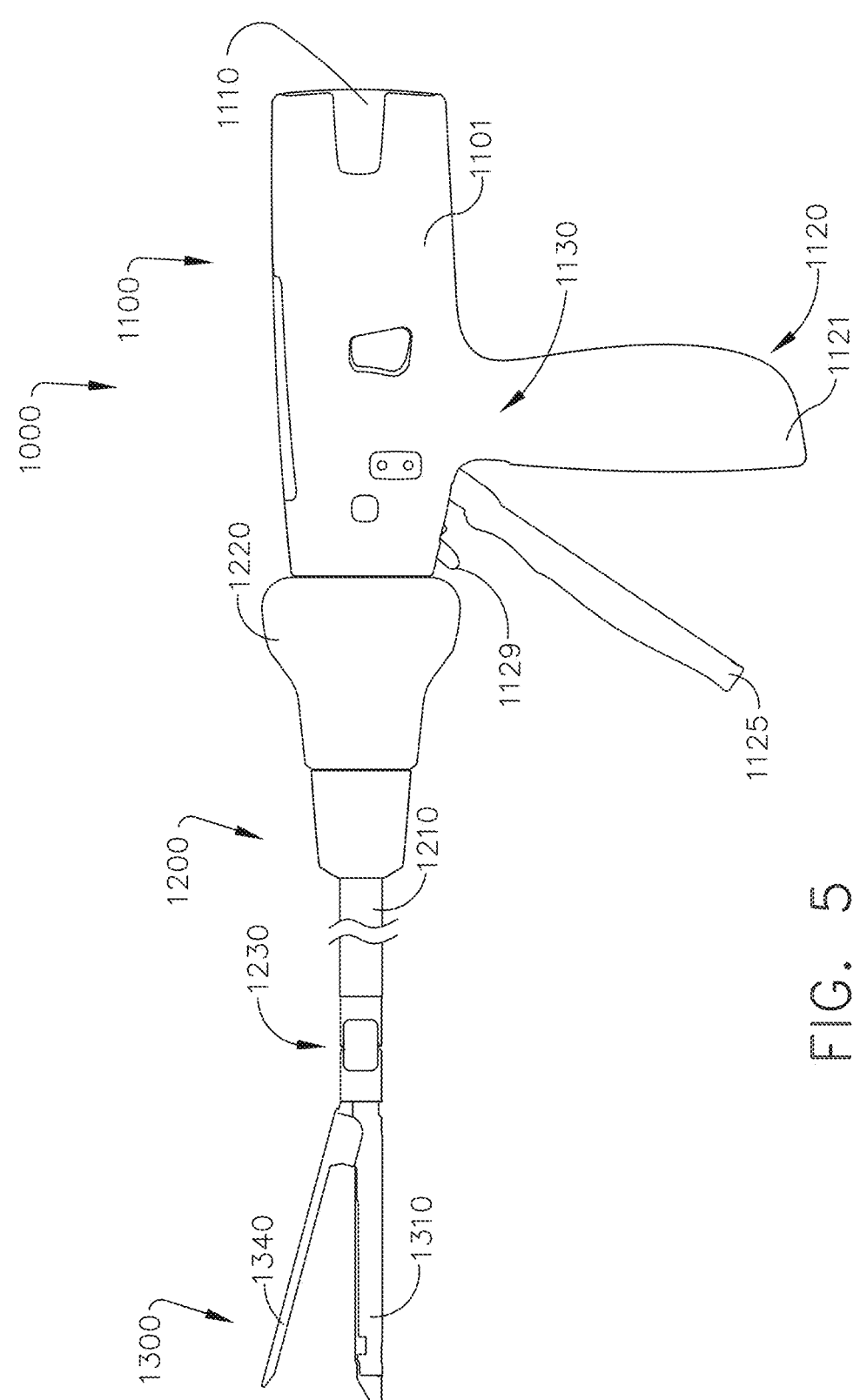
FIG. 5 is schematic view of the surgical stapling instrument of FIG. 1.

Applicant of the present application owns the following U.S. Patent Applications filed concurrently herewith, the disclosure of each of which is herein incorporated by reference in its entirety:

U.S. patent application Ser. No. 17/513,690 entitled ELECTRICAL LEAD ARRANGEMENTS FOR SURGICAL INSTRUMENTS;

U.S. patent application Ser. No. 17/513,694 entitled SURGICAL DEVICE WITH INTERNAL COMMUNICATION THAT COMBINES MULTIPLE SIGNALS PER WIRE;

U.S. patent application Ser. No. 17/513,700 entitled SURGICAL INSTRUMENT CARTRIDGE WITH UNIQUE RESISTOR FOR SURGICAL INSTRUMENT IDENTIFICATION;

U.S. patent application Ser. No. 17/513,703 entitled METHOD AND DEVICE FOR TRANSMITTING UART COMMUNICATIONS OVER A SECURITY SHORT RANGE WIRELESS COMMUNICATION; and U.S. patent application Ser. No. 17/513,705 entitled ALTERNATE MEANS TO ESTABLISH RESISTIVE LOAD FORCE.

Applicant of the present application also owns the following U.S. Patent Applications that were filed on Apr. 11, 2020 and which are each herein incorporated by reference in their respective entireties:

U.S. patent application Ser. No. 16/846,303, entitled METHODS FOR STAPLING TISSUE USING A SURGICAL INSTRUMENT;

U.S. patent application Ser. No. 16/846,304, entitled ARTICULATION ACTUATORS FOR A SURGICAL INSTRUMENT;

U.S. patent application Ser. No. 16/846,305, entitled ARTICULATION DIRECTIONAL LIGHTS ON A SURGICAL INSTRUMENT;

U.S. patent application Ser. No. 16/846,307, entitled SHAFT ROTATION ACTUATOR ON A SURGICAL INSTRUMENT;

U.S. patent application Ser. No. 16/846,308, entitled ARTICULATION CONTROL MAPPING FOR A SURGICAL INSTRUMENT;

U.S. patent application Ser. No. 16/846,309, entitled INTELLIGENT FIRING ASSOCIATED WITH A SURGICAL INSTRUMENT;

U.S. patent application Ser. No. 16/846,310, entitled INTELLIGENT FIRING ASSOCIATED WITH A SURGICAL INSTRUMENT;

U.S. patent application Ser. No. 16/846,311, entitled ROTATABLE JAW TIP FOR A SURGICAL INSTRUMENT;

U.S. patent application Ser. No. 16/846,312, entitled TISSUE STOP FOR A SURGICAL INSTRUMENT; and U.S. patent application Ser. No. 16/846,313, entitled ARTICULATION PIN FOR A SURGICAL INSTRUMENT.

The entire disclosure of U.S. Provisional Patent Application Ser. No. 62/840,715, entitled SURGICAL INSTRUMENT COMPRISING AN ADAPTIVE CONTROL SYSTEM, filed Apr. 30, 2019, is hereby incorporated by reference herein.

Applicant of the present application owns the following U.S. Patent Applications that were filed on Feb. 21, 2019 and which are each herein incorporated by reference in their respective entireties:

U.S. patent application Ser. No. 16/281,658, entitled METHODS FOR CONTROLLING A POWERED SURGICAL STAPLER THAT HAS SEPARATE ROTARY CLOSURE AND FIRING SYSTEMS;

U.S. patent application Ser. No. 16/281,670, entitled STAPLE CARTRIDGE COMPRISING A LOCKOUT KEY CONFIGURED TO LIFT A FIRING MEMBER;

U.S. patent application Ser. No. 16/281,675, entitled surgical staplers with arrangements for maintaining a firing member thereof in a locked configuration unless a compatible cartridge has been installed therein;

U.S. patent application Ser. No. 16/281,685, entitled SURGICAL INSTRUMENT COMPRISING CO-OPERATING LOCKOUT FEATURES;

U.S. patent application Ser. No. 16/281,693, entitled SURGICAL STAPLING ASSEMBLY COMPRISING A LOCKOUT AND AN EXTERIOR ACCESS ORIFICE TO PERMIT ARTIFICIAL UNLOCKING OF THE LOCKOUT;

U.S. patent application Ser. No. 16/281,704, entitled SURGICAL STAPLING DEVICES WITH FEATURES FOR BLOCKING ADVANCEMENT OF A CAMMING ASSEMBLY OF AN INCOMPATIBLE CARTRIDGE INSTALLED THEREIN;

U.S. patent application Ser. No. 16/281,707, entitled STAPLING INSTRUMENT COMPRISING A DEACTIVATABLE LOCKOUT;

U.S. patent application Ser. No. 16/281,741, entitled SURGICAL INSTRUMENT COMPRISING A JAW CLOSURE LOCKOUT;

U.S. patent application Ser. No. 16/281,762, entitled SURGICAL STAPLING DEVICES WITH CARTRIDGE COMPATIBLE CLOSURE AND FIRING LOCKOUT ARRANGEMENTS;

U.S. patent application Ser. No. 16/281,666, entitled SURGICAL STAPLING DEVICES WITH IMPROVED ROTARY DRIVEN CLOSURE SYSTEMS;

U.S. patent application Ser. No. 16/281,672, entitled SURGICAL STAPLING DEVICES WITH ASYMMETRIC CLOSURE FEATURES;

U.S. patent application Ser. No. 16/281,678, entitled ROTARY DRIVEN FIRING MEMBERS WITH DIFFERENT ANVIL AND CHANNEL ENGAGEMENT FEATURES; and U.S. patent application Ser. No. 16/281,682, entitled SURGICAL STAPLING DEVICE WITH SEPARATE ROTARY DRIVEN CLOSURE AND FIRING SYSTEMS AND FIRING MEMBER THAT ENGAGES BOTH JAWS WHILE FIRING.

Applicant of the present application owns the following U.S. Provisional Patent Applications that were filed on Feb. 19, 2019 and which are each herein incorporated by reference in their respective entireties:

U.S. Provisional Patent Application Ser. No. 62/807,310, entitled METHODS FOR CONTROLLING A POWERED SURGICAL STAPLER THAT HAS SEPARATE ROTARY CLOSURE AND FIRING SYSTEMS;

U.S. Provisional Patent Application Ser. No. 62/807,319, entitled SURGICAL STAPLING DEVICES WITH IMPROVED LOCKOUT SYSTEMS; and U.S. Provisional Patent Application Ser. No. 62/807,309, entitled SURGICAL STAPLING DEVICES WITH IMPROVED ROTARY DRIVEN CLOSURE SYSTEMS.

Applicant of the present application owns the following U.S. Provisional Patent Applications, filed on Mar. 28, 2018, each of which is herein incorporated by reference in its entirety:

5

U.S. Provisional Patent Application Ser. No. 62/649,302, entitled INTERACTIVE SURGICAL SYSTEMS WITH encrypted COMMUNICATION CAPABILITIES;

U.S. Provisional Patent Application Ser. No. 62/649,294, entitled DATA STRIPPING METHOD TO INTERROGATE PATIENT RECORDS AND CREATE ANONYMIZED RECORD;

U.S. Provisional Patent Application Ser. No. 62/649,300, entitled SURGICAL HUB SITUATIONAL AWARENESS;

U.S. Provisional Patent Application Ser. No. 62/649,309, entitled SURGICAL HUB SPATIAL AWARENESS TO DETERMINE DEVICES IN OPERATING THEATER;

U.S. Provisional Patent Application Ser. No. 62/649,310, entitled COMPUTER IMPLEMENTED INTERACTIVE SURGICAL SYSTEMS;

U.S. Provisional Patent Application Ser. No. 62/649,291, entitled USE OF LASER LIGHT AND RED-GREEN-BLUE COLORATION TO DETERMINE PROPERTIES OF BACK SCATTERED LIGHT;

U.S. Provisional Patent Application Ser. No. 62/649,296, entitled ADAPTIVE CONTROL PROGRAM UPDATES FOR SURGICAL DEVICES;

U.S. Provisional Patent Application Ser. No. 62/649,333, entitled CLOUD-BASED MEDICAL ANALYTICS FOR CUSTOMIZATION AND RECOMMENDATIONS TO A USER;

U.S. Provisional Patent Application Ser. No. 62/649,327, entitled CLOUD-BASED MEDICAL ANALYTICS FOR SECURITY AND AUTHENTICATION TRENDS AND REACTIVE MEASURES;

U.S. Provisional Patent Application Ser. No. 62/649,315, entitled DATA HANDLING AND PRIORITIZATION IN A CLOUD ANALYTICS NETWORK;

U.S. Provisional Patent Application Ser. No. 62/649,313, entitled CLOUD INTERFACE FOR COUPLED SURGICAL DEVICES;

U.S. Provisional Patent Application Ser. No. 62/649,320, entitled DRIVE ARRANGEMENTS FOR ROBOT-ASSISTED SURGICAL PLATFORMS;

U.S. Provisional Patent Application Ser. No. 62/649,307, entitled AUTOMATIC TOOL ADJUSTMENTS FOR ROBOT-ASSISTED SURGICAL PLATFORMS; and U.S. Provisional Patent Application Ser. No. 62/649,323, entitled SENSING ARRANGEMENTS FOR ROBOT-ASSISTED SURGICAL PLATFORMS.

Applicant of the present application owns the following U.S. Provisional Patent Application, filed on Mar. 30, 2018, which is herein incorporated by reference in its entirety:

U.S. Provisional Patent Application Ser. No. 62/650,887, entitled SURGICAL SYSTEMS WITH OPTIMIZED SENSING CAPABILITIES.

Applicant of the present application owns the following U.S. Patent Application, filed on Dec. 4, 2018, which is herein incorporated by reference in its entirety:

U.S. patent application Ser. No. 16/209,423, entitled METHOD OF COMPRESSING TISSUE WITHIN A STAPLING DEVICE AND SIMULTANEOUSLY DISPLAYING THE LOCATION OF THE TISSUE WITHIN THE JAWS.

Applicant of the present application owns the following U.S. Patent Applications that were filed on Aug. 20, 2018 and which are each herein incorporated by reference in their respective entireties:

6

U.S. patent application Ser. No. 16/105,101, entitled METHOD FOR FABRICATING SURGICAL STAPLER ANVILS;

U.S. patent application Ser. No. 16/105,183, entitled REINFORCED DEFORMABLE ANVIL TIP FOR SURGICAL STAPLER ANVIL;

U.S. patent application Ser. No. 16/105,150, entitled SURGICAL STAPLER ANVILS WITH STAPLE DIRECTING PROTRUSIONS AND TISSUE STABILITY FEATURES;

U.S. patent application Ser. No. 16/105,098, entitled FABRICATING TECHNIQUES FOR SURGICAL STAPLER ANVILS;

U.S. patent application Ser. No. 16/105,140, entitled SURGICAL STAPLER ANVILS WITH TISSUE STOP FEATURES CONFIGURED TO AVOID TISSUE PINCH;

U.S. patent application Ser. No. 16/105,081, entitled METHOD FOR OPERATING A POWERED ARTICULATABLE SURGICAL INSTRUMENT;

U.S. patent application Ser. No. 16/105,094, entitled SURGICAL INSTRUMENTS WITH PROGRESSIVE JAW CLOSURE ARRANGEMENTS;

U.S. patent application Ser. No. 16/105,097, entitled POWERED SURGICAL INSTRUMENTS WITH CLUTCHING ARRANGEMENTS TO CONVERT LINEAR DRIVE MOTIONS TO ROTARY DRIVE MOTIONS;

U.S. patent application Ser. No. 16/105,104, entitled POWERED ARTICULATABLE SURGICAL INSTRUMENTS WITH CLUTCHING AND LOCKING ARRANGEMENTS FOR LINKING AN ARTICULATION DRIVE SYSTEM TO A FIRING DRIVE SYSTEM;

U.S. patent application Ser. No. 16/105,119, entitled ARTICULATABLE MOTOR POWERED SURGICAL INSTRUMENTS WITH DEDICATED ARTICULATION MOTOR ARRANGEMENTS;

U.S. patent application Ser. No. 16/105,160, entitled SWITCHING ARRANGEMENTS FOR MOTOR POWERED ARTICULATABLE SURGICAL INSTRUMENTS; and U.S. Design patent application Ser. No. 29/660,252, entitled SURGICAL STAPLER ANVILS.

Applicant of the present application owns the following U.S. Patent Applications and U.S. Patents that are each herein incorporated by reference in their respective entireties:

U.S. patent application Ser. No. 15/386,185, entitled SURGICAL STAPLING INSTRUMENTS AND REPLACEABLE TOOL ASSEMBLIES THEREOF, now U.S. Patent Application Publication No. 2018/0168642;

U.S. patent application Ser. No. 15/386,230, entitled ARTICULATABLE SURGICAL STAPLING INSTRUMENTS, now U.S. Patent Application Publication No. 2018/0168649;

U.S. patent application Ser. No. 15/386,221, entitled LOCKOUT ARRANGEMENTS FOR SURGICAL END EFFECTORS, now U.S. Patent Application Publication No. 2018/0168646;

U.S. patent application Ser. No. 15/386,209, entitled SURGICAL END EFFECTORS AND FIRING MEMBERS THEREOF, now U.S. Patent Application Publication No. 2018/0168645;

U.S. patent application Ser. No. 15/386,198, entitled LOCKOUT ARRANGEMENTS FOR SURGICAL END EFFECTORS AND REPLACEABLE TOOL ASSEMBLIES, now U.S. Patent Application Publication No. 2018/0168644;

U.S. patent application Ser. No. 15/386,240, entitled SURGICAL END EFFECTORS AND ADAPTABLE FIRING MEMBERS THEREFOR, now U.S. Patent Application Publication No. 2018/0168651;

U.S. patent application Ser. No. 15/385,939, entitled STAPLE CARTRIDGES AND ARRANGEMENTS OF STAPLES AND STAPLE CAVITIES THEREIN, now U.S. Patent Application Publication No. 2018/0168629;

U.S. patent application Ser. No. 15/385,941, entitled SURGICAL TOOL ASSEMBLIES WITH CLUTCHING ARRANGEMENTS FOR SHIFTING BETWEEN CLOSURE SYSTEMS WITH CLOSURE STROKE REDUCTION FEATURES AND ARTICULATION AND FIRING SYSTEMS, now U.S. Patent Application Publication No. 2018/0168630;

U.S. patent application Ser. No. 15/385,943, entitled SURGICAL STAPLING INSTRUMENTS AND STAPLE-FORMING ANVILS, now U.S. Patent Application Publication No. 2018/0168631;

U.S. patent application Ser. No. 15/385,950, entitled SURGICAL TOOL ASSEMBLIES WITH CLOSURE STROKE REDUCTION FEATURES, now U.S. Patent Application Publication No. 2018/0168635;

U.S. patent application Ser. No. 15/385,945, entitled STAPLE CARTRIDGES AND ARRANGEMENTS OF STAPLES AND STAPLE CAVITIES THEREIN, now U.S. Patent Application Publication No. 2018/0168632;

U.S. patent application Ser. No. 15/385,946, entitled SURGICAL STAPLING INSTRUMENTS AND STAPLE-FORMING ANVILS, now U.S. Patent Application Publication No. 2018/0168633;

U.S. patent application Ser. No. 15/385,951, entitled SURGICAL INSTRUMENTS WITH JAW OPENING FEATURES FOR INCREASING A JAW OPENING DISTANCE, now U.S. Patent Application Publication No. 2018/0168636;

U.S. patent application Ser. No. 15/385,953, entitled METHODS OF STAPLING TISSUE, now U.S. Patent Application Publication No. 2018/0168637;

U.S. patent application Ser. No. 15/385,954, entitled FIRING MEMBERS WITH NON-PARALLEL JAW ENGAGEMENT FEATURES FOR SURGICAL END EFFECTORS, now U.S. Patent Application Publication No. 2018/0168638;

U.S. patent application Ser. No. 15/385,955, entitled SURGICAL END EFFECTORS WITH EXPANDABLE TISSUE STOP ARRANGEMENTS, now U.S. Patent Application Publication No. 2018/0168639;

U.S. patent application Ser. No. 15/385,948, entitled SURGICAL STAPLING INSTRUMENTS AND STAPLE-FORMING ANVILS, now U.S. Patent Application Publication No. 2018/0168584;

U.S. patent application Ser. No. 15/385,956, entitled SURGICAL INSTRUMENTS WITH POSITIVE JAW OPENING FEATURES, now U.S. Patent Application Publication No. 2018/0168640;

U.S. patent application Ser. No. 15/385,958, entitled SURGICAL INSTRUMENTS WITH LOCKOUT ARRANGEMENTS FOR PREVENTING FIRING SYSTEM ACTUATION UNLESS AN UNSPENT STAPLE CARTRIDGE IS PRESENT, now U.S. Patent Application Publication No. 2018/0168641;

U.S. patent application Ser. No. 15/385,947, entitled STAPLE CARTRIDGES AND ARRANGEMENTS OF STAPLES AND STAPLE CAVITIES THEREIN, now U.S. Patent Application Publication No. 2018/0168634;

U.S. patent application Ser. No. 15/385,896, entitled METHOD FOR RESETTING A FUSE OF A SURGICAL INSTRUMENT SHAFT, now U.S. Patent Application Publication No. 2018/0168597;

U.S. patent application Ser. No. 15/385,898, entitled STAPLE-FORMING POCKET ARRANGEMENT TO ACCOMMODATE DIFFERENT TYPES OF STAPLES, now U.S. Patent Application Publication No. 2018/0168599;

U.S. patent application Ser. No. 15/385,899, entitled SURGICAL INSTRUMENT COMPRISING IMPROVED JAW CONTROL, now U.S. Patent Application Publication No. 2018/0168600;

U.S. patent application Ser. No. 15/385,901, entitled STAPLE CARTRIDGE AND STAPLE CARTRIDGE CHANNEL COMPRISING WINDOWS DEFINED THEREIN, now U.S. Patent Application Publication No. 2018/0168602;

U.S. patent application Ser. No. 15/385,902, entitled SURGICAL INSTRUMENT COMPRISING A CUTTING MEMBER, now U.S. Patent Application Publication No. 2018/0168603;

U.S. patent application Ser. No. 15/385,904, entitled STAPLE FIRING MEMBER COMPRISING A MISSING CARTRIDGE AND/OR SPENT CARTRIDGE LOCKOUT, now U.S. Patent Application Publication No. 2018/0168605;

U.S. patent application Ser. No. 15/385,905, entitled FIRING ASSEMBLY COMPRISING A LOCKOUT, now U.S. Patent Application Publication No. 2018/0168606;

U.S. patent application Ser. No. 15/385,907, entitled SURGICAL INSTRUMENT SYSTEM COMPRISING AN END EFFECTOR LOCKOUT AND A FIRING ASSEMBLY LOCKOUT, now U.S. Patent Application Publication No. 2018/0168608;

U.S. patent application Ser. No. 15/385,908, entitled FIRING ASSEMBLY COMPRISING A FUSE, now U.S. Patent Application Publication No. 2018/0168609;

U.S. patent application Ser. No. 15/385,909, entitled FIRING ASSEMBLY COMPRISING A MULTIPLE FAILED-STATE FUSE, now U.S. Patent Application Publication No. 2018/0168610;

U.S. patent application Ser. No. 15/385,920, entitled STAPLE-FORMING POCKET ARRANGEMENTS, now U.S. Patent Application Publication No. 2018/0168620;

U.S. patent application Ser. No. 15/385,913, entitled ANVIL ARRANGEMENTS FOR SURGICAL STAPLERS, now U.S. Patent Application Publication No. 2018/0168614;

U.S. patent application Ser. No. 15/385,914, entitled METHOD OF DEFORMING STAPLES FROM TWO DIFFERENT TYPES OF STAPLE CARTRIDGES WITH THE SAME SURGICAL STAPLING INSTRUMENT, now U.S. Patent Application Publication No. 2018/0168615;

U.S. patent application Ser. No. 15/385,893, entitled BILATERALLY ASYMMETRIC STAPLE-FORMING POCKET PAIRS, now U.S. Patent Application Publication No. 2018/0168594;

U.S. patent application Ser. No. 15/385,929, entitled CLOSURE MEMBERS WITH CAM SURFACE ARRANGEMENTS FOR SURGICAL INSTRUMENTS WITH SEPARATE AND DISTINCT CLOSURE AND FIRING SYSTEMS, now U.S. Patent Application Publication No. 2018/0168626;

U.S. patent application Ser. No. 15/385,911, entitled SURGICAL STAPLERS WITH INDEPENDENTLY ACTUATABLE CLOSING AND FIRING SYSTEMS, now U.S. Patent Application Publication No. 2018/0168612;

U.S. patent application Ser. No. 15/385,927, entitled SURGICAL STAPLING INSTRUMENTS WITH SMART STAPLE CARTRIDGES, now U.S. Patent Application Publication No. 2018/0168625;

U.S. patent application Ser. No. 15/385,917, entitled STAPLE CARTRIDGE COMPRISING STAPLES WITH DIFFERENT CLAMPING BREADTHS, now U.S. Patent Application Publication No. 2018/0168617;

U.S. patent application Ser. No. 15/385,900, entitled STAPLE-FORMING POCKET ARRANGEMENTS COMPRISING PRIMARY SIDEWALLS AND POCKET SIDEWALLS, now U.S. Patent Application Publication No. 2018/0168601;

U.S. patent application Ser. No. 15/385,931, entitled NO-CARTRIDGE AND SPENT CARTRIDGE LOCKOUT ARRANGEMENTS FOR SURGICAL STAPLERS, now U.S. Patent Application Publication No. 2018/0168627;

U.S. patent application Ser. No. 15/385,915, entitled FIRING MEMBER PIN ANGLE, now U.S. Patent Application Publication No. 2018/0168616;

U.S. patent application Ser. No. 15/385,897, entitled STAPLE-FORMING POCKET ARRANGEMENTS COMPRISING ZONED FORMING SURFACE GROOVES, now U.S. Patent Application Publication No. 2018/0168598;

U.S. patent application Ser. No. 15/385,922, entitled SURGICAL INSTRUMENT WITH MULTIPLE FAILURE RESPONSE MODES, now U.S. Patent Application Publication No. 2018/0168622;

U.S. patent application Ser. No. 15/385,924, entitled SURGICAL INSTRUMENT WITH PRIMARY AND SAFETY PROCESSORS, now U.S. Patent Application Publication No. 2018/0168624;

U.S. patent application Ser. No. 15/385,910, entitled ANVIL HAVING A KNIFE SLOT WIDTH, now U.S. Patent Application Publication No. 2018/0168611;

U.S. patent application Ser. No. 15/385,903, entitled CLOSURE MEMBER ARRANGEMENTS FOR SURGICAL INSTRUMENTS, now U.S. Patent Application Publication No. 2018/0168604;

U.S. patent application Ser. No. 15/385,906, entitled FIRING MEMBER PIN CONFIGURATIONS, now U.S. Patent Application Publication No. 2018/0168607;

U.S. patent application Ser. No. 15/386,188, entitled STEPPED STAPLE CARTRIDGE WITH ASYMMETRICAL STAPLES, now U.S. Patent Application Publication No. 2018/0168585;

U.S. patent application Ser. No. 15/386,192, entitled STEPPED STAPLE CARTRIDGE WITH TISSUE RETENTION AND GAP SETTING FEATURES, now U.S. Patent Application Publication No. 2018/0168643;

U.S. patent application Ser. No. 15/386,206, entitled STAPLE CARTRIDGE WITH DEFORMABLE DRIVER RETENTION FEATURES, now U.S. Patent Application Publication No. 2018/0168586;

U.S. patent application Ser. No. 15/386,226, entitled DURABILITY FEATURES FOR END EFFECTORS AND FIRING ASSEMBLIES OF SURGICAL STAPLING INSTRUMENTS, now U.S. Patent Application Publication No. 2018/0168648;

U.S. patent application Ser. No. 15/386,222, entitled SURGICAL STAPLING INSTRUMENTS HAVING END EFFECTORS WITH POSITIVE OPENING FEATURES, now U.S. Patent Application Publication No. 2018/0168647;

U.S. patent application Ser. No. 15/386,236, entitled CONNECTION PORTIONS FOR DEPOSABLE LOADING UNITS FOR SURGICAL STAPLING INSTRUMENTS, now U.S. Patent Application Publication No. 2018/0168650;

U.S. patent application Ser. No. 15/385,887, entitled METHOD FOR ATTACHING A SHAFT ASSEMBLY TO A SURGICAL INSTRUMENT AND, ALTERNATIVELY, TO A SURGICAL ROBOT, now U.S. Patent Application Publication No. 2018/0168589;

U.S. patent application Ser. No. 15/385,889, entitled SHAFT ASSEMBLY COMPRISING A MANUALLY-OPERABLE RETRACTION SYSTEM FOR USE WITH A MOTORIZED SURGICAL INSTRUMENT SYSTEM, now U.S. Patent Application Publication No. 2018/0168590;

U.S. patent application Ser. No. 15/385,890, entitled SHAFT ASSEMBLY COMPRISING SEPARATELY ACTUATABLE AND RETRACTABLE SYSTEMS, now U.S. Patent Application Publication No. 2018/0168591;

U.S. patent application Ser. No. 15/385,891, entitled SHAFT ASSEMBLY COMPRISING A CLUTCH CONFIGURED TO ADAPT THE OUTPUT OF A ROTARY FIRING MEMBER TO TWO DIFFERENT SYSTEMS, now U.S. Patent Application Publication No. 2018/0168592;

U.S. patent application Ser. No. 15/385,892, entitled SURGICAL SYSTEM COMPRISING A FIRING MEMBER ROTATABLE INTO AN ARTICULATION STATE TO ARTICULATE AN END EFFECTOR OF THE SURGICAL SYSTEM, now U.S. Patent Application Publication No. 2018/0168593;

U.S. patent application Ser. No. 15/385,894, entitled SHAFT ASSEMBLY COMPRISING A LOCKOUT, now U.S. Patent Application Publication No. 2018/0168595;

U.S. patent application Ser. No. 15/385,895, entitled SHAFT ASSEMBLY COMPRISING FIRST AND SECOND ARTICULATION LOCKOUTS, now U.S. Patent Application Publication No. 2018/0168596;

U.S. patent application Ser. No. 15/385,916, entitled SURGICAL STAPLING SYSTEMS, now U.S. Patent Application Publication No. 2018/0168575;

U.S. patent application Ser. No. 15/385,918, entitled SURGICAL STAPLING SYSTEMS, now U.S. Patent Application Publication No. 2018/0168618;

U.S. patent application Ser. No. 15/385,919, entitled SURGICAL STAPLING SYSTEMS, now U.S. Patent Application Publication No. 2018/0168619;

U.S. patent application Ser. No. 15/385,921, entitled SURGICAL STAPLE CARTRIDGE WITH MOVABLE CAMMING MEMBER CONFIGURED TO

11

DISENGAGE FIRING MEMBER LOCKOUT FEATURES, now U.S. Patent Application Publication No. 2018/0168621;

U.S. patent application Ser. No. 15/385,923, entitled SURGICAL STAPLING SYSTEMS, now U.S. Patent Application Publication No. 2018/0168623;

U.S. patent application Ser. No. 15/385,925, entitled JAW ACTUATED LOCK ARRANGEMENTS FOR PREVENTING ADVANCEMENT OF A FIRING MEMBER IN A SURGICAL END EFFECTOR UNLESS AN UNFIRED CARTRIDGE IS INSTALLED IN THE END EFFECTOR, now U.S. Patent Application Publication No. 2018/0168576;

U.S. patent application Ser. No. 15/385,926, entitled AXIALLY MOVABLE CLOSURE SYSTEM ARRANGEMENTS FOR APPLYING CLOSURE MOTIONS TO JAWS OF SURGICAL INSTRUMENTS, now U.S. Patent Application Publication No. 2018/0168577;

U.S. patent application Ser. No. 15/385,928, entitled PROTECTIVE COVER ARRANGEMENTS FOR A JOINT INTERFACE BETWEEN A MOVABLE JAW AND ACTUATOR SHAFT OF A SURGICAL INSTRUMENT, now U.S. Patent Application Publication No. 2018/0168578;

U.S. patent application Ser. No. 15/385,930, entitled SURGICAL END EFFECTOR WITH TWO SEPARATE COOPERATING OPENING FEATURES FOR OPENING AND CLOSING END EFFECTOR JAWS, now U.S. Patent Application Publication No. 2018/0168579;

U.S. patent application Ser. No. 15/385,932, entitled ARTICULATABLE SURGICAL END EFFECTOR WITH ASYMMETRIC SHAFT ARRANGEMENT, now U.S. Patent Application Publication No. 2018/0168628;

U.S. patent application Ser. No. 15/385,933, entitled ARTICULATABLE SURGICAL INSTRUMENT WITH INDEPENDENT PIVOTABLE LINKAGE DISTAL OF AN ARTICULATION LOCK, now U.S. Patent Application Publication No. 2018/0168580;

U.S. patent application Ser. No. 15/385,934, entitled ARTICULATION LOCK ARRANGEMENTS FOR LOCKING AN END EFFECTOR IN AN ARTICULATED POSITION IN RESPONSE TO ACTUATION OF A JAW CLOSURE SYSTEM, now U.S. Patent Application Publication No. 2018/0168581;

U.S. patent application Ser. No. 15/385,935, entitled LATERALLY ACTUATABLE ARTICULATION LOCK ARRANGEMENTS FOR LOCKING AN END EFFECTOR OF A SURGICAL INSTRUMENT IN AN ARTICULATED CONFIGURATION, now U.S. Patent Application Publication No. 2018/0168582;

U.S. patent application Ser. No. 15/385,936, entitled ARTICULATABLE SURGICAL INSTRUMENTS WITH ARTICULATION STROKE AMPLIFICATION FEATURES, now U.S. Patent Application Publication No. 2018/0168583;

U.S. patent application Ser. No. 14/318,996, entitled FASTENER CARTRIDGES INCLUDING EXTENSIONS HAVING DIFFERENT CONFIGURATIONS, now U.S. Patent Application Publication No. 2015/0297228;

U.S. patent application Ser. No. 14/319,006, entitled FASTENER CARTRIDGE COMPRISING FASTENER CAVITIES INCLUDING FASTENER CONTROL FEATURES, now U.S. Pat. No. 10,010,324;

U.S. patent application Ser. No. 14/318,991, entitled SURGICAL FASTENER CARTRIDGES WITH DRIVER STABILIZING ARRANGEMENTS, now U.S. Pat. No. 9,833,241;

U.S. patent application Ser. No. 14/319,004, entitled SURGICAL END EFFECTORS WITH FIRING ELEMENT MONITORING ARRANGEMENTS, now U.S. Pat. No. 9,844,369;

U.S. patent application Ser. No. 14/319,008, entitled FASTENER CARTRIDGE COMPRISING NONUNIFORM FASTENERS, now U.S. Patent Application Publication No. 2015/0297232;

U.S. patent application Ser. No. 14/318,997, entitled FASTENER CARTRIDGE COMPRISING DEPLOYABLE TISSUE ENGAGING MEMBERS, now U.S. Patent Application Publication No. 2015/0297229;

U.S. patent application Ser. No. 14/319,002, entitled FASTENER CARTRIDGE COMPRISING TISSUE CONTROL FEATURES, now U.S. Pat. No. 9,877,721;

U.S. patent application Ser. No. 14/319,013, entitled FASTENER CARTRIDGE ASSEMBLIES AND STAPLE RETAINER COVER ARRANGEMENTS, now U.S. Patent Application Publication No. 2015/0297233; and U.S. patent application Ser. No. 14/319,016, entitled FASTENER CARTRIDGE INCLUDING A LAYER ATTACHED THERETO, now U.S. Patent Application Publication No. 2015/0297235.

Applicant of the present application owns the following U.S. Patent Applications that were filed on Jun. 24, 2016 and which are each herein incorporated by reference in their respective entireties:

U.S. patent application Ser. No. 15/191,775, entitled STAPLE CARTRIDGE COMPRISING WIRE STAPLES AND STAMPED STAPLES, now U.S. Patent Application Publication No. 2017/0367695;

U.S. patent application Ser. No. 15/191,807, entitled STAPLING SYSTEM FOR USE WITH WIRE STAPLES AND STAMPED STAPLES, now U.S. Patent Application Publication No. 2017/0367696;

U.S. patent application Ser. No. 15/191,834, entitled STAMPED STAPLES AND STAPLE CARTRIDGES USING THE SAME, now U.S. Patent Application Publication No. 2017/0367699;

U.S. patent application Ser. No. 15/191,788, entitled STAPLE CARTRIDGE COMPRISING OVERDRIVEN STAPLES, now U.S. Patent Application Publication No. 2017/0367698; and U.S. patent application Ser. No. 15/191,818, entitled STAPLE CARTRIDGE COMPRISING OFFSET LONGITUDINAL STAPLE ROWS, now U.S. Patent Application Publication No. 2017/0367697.

Applicant of the present application owns the following U.S. Patent Applications that were filed on Jun. 24, 2016 and which are each herein incorporated by reference in their respective entireties:

U.S. Design patent application Ser. No. 29/569,218, entitled SURGICAL FASTENER, now U.S. Design Pat. No. D826,405;

U.S. Design patent application Ser. No. 29/569,227, entitled SURGICAL FASTENER, now U.S. Design Pat. No. D822,206;

U.S. Design patent application Ser. No. 29/569,259, entitled SURGICAL FASTENER CARTRIDGE; and U.S. Design patent application Ser. No. 29/569,264, entitled SURGICAL FASTENER CARTRIDGE.

Applicant of the present application owns the following patent applications that were filed on Apr. 1, 2016 and which are each herein incorporated by reference in their respective entirety:

U.S. patent application Ser. No. 15/089,325, entitled METHOD FOR OPERATING A SURGICAL STAPLING SYSTEM, now U.S. Patent Application Publication No. 2017/0281171;

U.S. patent application Ser. No. 15/089,321, entitled MODULAR SURGICAL STAPLING SYSTEM COMPRISING A DISPLAY, now U.S. Pat. No. 10,271, 851;

U.S. patent application Ser. No. 15/089,326, entitled SURGICAL STAPLING SYSTEM COMPRISING A DISPLAY INCLUDING A RE-ORIENTABLE DISPLAY FIELD, now U.S. Patent Application Publication No. 2017/0281172;

U.S. patent application Ser. No. 15/089,263, entitled SURGICAL INSTRUMENT HANDLE ASSEMBLY WITH RECONFIGURABLE GRIP PORTION, now U.S. Patent Application Publication No. 2017/0281165;

U.S. patent application Ser. No. 15/089,262, entitled ROTARY POWERED SURGICAL INSTRUMENT WITH MANUALLY ACTUATABLE BAILOUT SYSTEM, now U.S. Patent Application Publication No. 2017/0281161;

U.S. patent application Ser. No. 15/089,277, entitled SURGICAL CUTTING AND STAPLING END EFFECTOR WITH ANVIL CONCENTRIC DRIVE MEMBER, now U.S. Patent Application Publication No. 2017/0281166;

U.S. patent application Ser. No. 15/089,296, entitled INTERCHANGEABLE SURGICAL TOOL ASSEMBLY WITH A SURGICAL END EFFECTOR THAT IS SELECTIVELY ROTATABLE ABOUT A SHAFT AXIS, now U.S. Patent Application Publication No. 2017/0281168;

U.S. patent application Ser. No. 15/089,258, entitled SURGICAL STAPLING SYSTEM COMPRISING A SHIFTABLE TRANSMISSION, now U.S. Patent Application Publication No. 2017/0281178;

U.S. patent application Ser. No. 15/089,278, entitled SURGICAL STAPLING SYSTEM CONFIGURED TO PROVIDE SELECTIVE CUTTING OF TISSUE, now U.S. Patent Application Publication No. 2017/0281162;

U.S. patent application Ser. No. 15/089,284, entitled SURGICAL STAPLING SYSTEM COMPRISING A CONTOURABLE SHAFT, now U.S. Patent Application Publication No. 2017/0281186;

U.S. patent application Ser. No. 15/089,295, entitled SURGICAL STAPLING SYSTEM COMPRISING A TISSUE COMPRESSION LOCKOUT, now U.S. Patent Application Publication No. 2017/0281187;

U.S. patent application Ser. No. 15/089,300, entitled SURGICAL STAPLING SYSTEM COMPRISING AN UNCLAMPING LOCKOUT, now U.S. Patent Application Publication No. 2017/0281179;

U.S. patent application Ser. No. 15/089,196, entitled SURGICAL STAPLING SYSTEM COMPRISING A JAW CLOSURE LOCKOUT, now U.S. Patent Application Publication No. 2017/0281183;

U.S. patent application Ser. No. 15/089,203, entitled SURGICAL STAPLING SYSTEM COMPRISING A JAW ATTACHMENT LOCKOUT, now U.S. Patent Application Publication No. 2017/0281184;

U.S. patent application Ser. No. 15/089,210, entitled SURGICAL STAPLING SYSTEM COMPRISING A SPENT CARTRIDGE LOCKOUT, now U.S. Patent Application Publication No. 2017/0281185;

U.S. patent application Ser. No. 15/089,324, entitled SURGICAL INSTRUMENT COMPRISING A SHIFTING MECHANISM, now U.S. Patent Application Publication No. 2017/0281170;

U.S. patent application Ser. No. 15/089,335, entitled SURGICAL STAPLING INSTRUMENT COMPRISING MULTIPLE LOCKOUTS, now U.S. Patent Application Publication No. 2017/0281155;

U.S. patent application Ser. No. 15/089,339, entitled SURGICAL STAPLING INSTRUMENT, now U.S. Patent Application Publication No. 2017/0281173;

U.S. patent application Ser. No. 15/089,253, entitled SURGICAL STAPLING SYSTEM CONFIGURED TO APPLY ANNULAR ROWS OF STAPLES HAVING DIFFERENT HEIGHTS, now U.S. Patent Application Publication No. 2017/0281177;

U.S. patent application Ser. No. 15/089,304, entitled SURGICAL STAPLING SYSTEM COMPRISING A GROOVED FORMING POCKET, now U.S. Patent Application Publication No. 2017/0281188;

U.S. patent application Ser. No. 15/089,331, entitled ANVIL MODIFICATION MEMBERS FOR SURGICAL STAPLERS, now U.S. Patent Application Publication No. 2017/0281180;

U.S. patent application Ser. No. 15/089,336, entitled STAPLE CARTRIDGES WITH ATRAUMATIC FEATURES, now U.S. Patent Application Publication No. 2017/0281164;

U.S. patent application Ser. No. 15/089,312, entitled CIRCULAR STAPLING SYSTEM COMPRISING AN INCISABLE TISSUE SUPPORT, now U.S. Patent Application Publication No. 2017/0281189;

U.S. patent application Ser. No. 15/089,309, entitled CIRCULAR STAPLING SYSTEM COMPRISING ROTARY FIRING SYSTEM, now U.S. Patent Application Publication No. 2017/0281169; and U.S. patent application Ser. No. 15/089,349, entitled CIRCULAR STAPLING SYSTEM COMPRISING LOAD CONTROL, now U.S. Patent Application Publication No. 2017/0281174.

Applicant of the present application also owns the U.S. Patent Applications identified below which were filed on Dec. 30, 2015 which are each herein incorporated by reference in their respective entirety:

U.S. patent application Ser. No. 14/984,488, entitled MECHANISMS FOR COMPENSATING FOR BATTERY PACK FAILURE IN POWERED SURGICAL INSTRUMENTS, now U.S. Patent Application Publication No. 2017/0189018;

U.S. patent application Ser. No. 14/984,525, entitled MECHANISMS FOR COMPENSATING FOR DRIVETRAIN FAILURE IN POWERED SURGICAL INSTRUMENTS, now U.S. Patent Application Publication No. 2017/0189019; and U.S. patent application Ser. No. 14/984,552, entitled SURGICAL INSTRUMENTS WITH SEPARABLE MOTORS AND MOTOR CONTROL CIRCUITS, now U.S. Pat. No. 10,265,068.

Applicant of the present application also owns the U.S. Patent Applications identified below which were filed on Feb. 9, 2016, which are each herein incorporated by reference in their respective entirety:

U.S. patent application Ser. No. 15/019,220, entitled SURGICAL INSTRUMENT WITH ARTICULATING AND AXIALLY TRANSLATABLE END EFFECTOR, now U.S. Pat. No. 10,245,029;

U.S. patent application Ser. No. 15/019,228, entitled SURGICAL INSTRUMENTS WITH MULTIPLE LINK ARTICULATION ARRANGEMENTS, now U.S. Patent Application Publication No. 2017/0224342;

U.S. patent application Ser. No. 15/019,196, entitled SURGICAL INSTRUMENT ARTICULATION MECHANISM WITH SLOTTED SECONDARY CONSTRAINT, now U.S. Patent Application Publication No. 2017/0224330;

U.S. patent application Ser. No. 15/019,206, entitled SURGICAL INSTRUMENTS WITH AN END EFFECTOR THAT IS HIGHLY ARTICULATABLE RELATIVE TO AN ELONGATE SHAFT ASSEMBLY, now U.S. Patent Application Publication No. 2017/0224331;

U.S. patent application Ser. No. 15/019,215, entitled SURGICAL INSTRUMENTS WITH NON-SYMMETRICAL ARTICULATION ARRANGEMENTS, now U.S. Patent Application Publication No. 2017/0224332;

U.S. patent application Ser. No. 15/019,227, entitled ARTICULATABLE SURGICAL INSTRUMENTS WITH SINGLE ARTICULATION LINK ARRANGEMENTS, now U.S. Patent Application Publication No. 2017/0224334;

U.S. patent application Ser. No. 15/019,235, entitled SURGICAL INSTRUMENTS WITH TENSIONING ARRANGEMENTS FOR CABLE DRIVEN ARTICULATION SYSTEMS, now U.S. Pat. No. 10,245,030;

U.S. patent application Ser. No. 15/019,230, entitled ARTICULATABLE SURGICAL INSTRUMENTS WITH OFF-AXIS FIRING BEAM ARRANGEMENTS, now U.S. Patent Application Publication No. 2017/0224335; and U.S. patent application Ser. No. 15/019,245, entitled SURGICAL INSTRUMENTS WITH CLOSURE STROKE REDUCTION ARRANGEMENTS, now U.S. Patent Application Publication No. 2017/0224343.

Applicant of the present application also owns the U.S. Patent Applications identified below which were filed on Feb. 12, 2016, which are each herein incorporated by reference in their respective entirety:

U.S. patent application Ser. No. 15/043,254, entitled MECHANISMS FOR COMPENSATING FOR DRIVETRAIN FAILURE IN POWERED SURGICAL INSTRUMENTS, now U.S. Pat. No. 10,258,331;

U.S. patent application Ser. No. 15/043,259, entitled MECHANISMS FOR COMPENSATING FOR DRIVETRAIN FAILURE IN POWERED SURGICAL INSTRUMENTS, now U.S. Patent Application Publication No. 2017/0231626;

U.S. patent application Ser. No. 15/043,275, entitled MECHANISMS FOR COMPENSATING FOR DRIVETRAIN FAILURE IN POWERED SURGICAL INSTRUMENTS, now U.S. Patent Application Publication No. 2017/0231627; and U.S. patent application Ser. No. 15/043,289, entitled MECHANISMS FOR COMPENSATING FOR DRIVETRAIN FAILURE IN POWERED SURGICAL INSTRUMENTS, now U.S. Patent Application Publication No. 2017/0231628.

Applicant of the present application owns the following patent applications that were filed on Jun. 18, 2015 and which are each herein incorporated by reference in their respective entirety:

U.S. patent application Ser. No. 14/742,925, entitled SURGICAL END EFFECTORS WITH POSITIVE JAW OPENING ARRANGEMENTS, now U.S. Pat. No. 10,182,818;

U.S. patent application Ser. No. 14/742,941, entitled SURGICAL END EFFECTORS WITH DUAL CAM ACTUATED JAW CLOSING FEATURES, now U.S. Pat. No. 10,052,102;

U.S. patent application Ser. No. 14/742,933, entitled SURGICAL STAPLING INSTRUMENTS WITH LOCKOUT ARRANGEMENTS FOR PREVENTING FIRING SYSTEM ACTUATION WHEN A CARTRIDGE IS SPENT OR MISSING, now U.S. Pat. No. 10,154,841;

U.S. patent application Ser. No. 14/742,914, entitled MOVABLE FIRING BEAM SUPPORT ARRANGEMENTS FOR ARTICULATABLE SURGICAL INSTRUMENTS, now U.S. Patent Application Publication No. 2016/0367255;

U.S. patent application Ser. No. 14/742,900, entitled ARTICULATABLE SURGICAL INSTRUMENTS WITH COMPOSITE FIRING BEAM STRUCTURES WITH CENTER FIRING SUPPORT MEMBER FOR ARTICULATION SUPPORT, now U.S. Patent Application Publication No. 2016/0367254;

U.S. patent application Ser. No. 14/742,885, entitled DUAL ARTICULATION DRIVE SYSTEM ARRANGEMENTS FOR ARTICULATABLE SURGICAL INSTRUMENTS, now U.S. Patent Application Publication No. 2016/0367246; and U.S. patent application Ser. No. 14/742,876, entitled PUSH/PULL ARTICULATION DRIVE SYSTEMS FOR ARTICULATABLE SURGICAL INSTRUMENTS, now U.S. Pat. No. 10,178,992.

Applicant of the present application owns the following patent applications that were filed on Mar. 6, 2015 and which are each herein incorporated by reference in their respective entirety:

U.S. patent application Ser. No. 14/640,746, entitled POWERED SURGICAL INSTRUMENT, now U.S. Pat. No. 9,808,246;

U.S. patent application Ser. No. 14/640,795, entitled MULTIPLE LEVEL THRESHOLDS TO MODIFY OPERATION OF POWERED SURGICAL INSTRUMENTS, now U.S. Patent Application Publication No. 2016/02561185;

U.S. patent application Ser. No. 14/640,832, entitled ADAPTIVE TISSUE COMPRESSION TECHNIQUES TO ADJUST CLOSURE RATES FOR MULTIPLE TISSUE TYPES, now U.S. Patent Application Publication No. 2016/0256154;

U.S. patent application Ser. No. 14/640,935, entitled OVERLAID MULTI SENSOR RADIO FREQUENCY (RF) ELECTRODE SYSTEM TO MEASURE TISSUE COMPRESSION, now U.S. Patent Application Publication No. 2016/0256071;

U.S. patent application Ser. No. 14/640,831, entitled MONITORING SPEED CONTROL AND PRECISION INCREMENTING OF MOTOR FOR POWERED SURGICAL INSTRUMENTS, now U.S. Pat. No. 9,895,148;

U.S. patent application Ser. No. 14/640,859, entitled TIME DEPENDENT EVALUATION OF SENSOR

17

DATA TO DETERMINE STABILITY, CREEP, AND VISCOELASTIC ELEMENTS OF MEASURES, now U.S. Pat. No. 10,052,044;

U.S. patent application Ser. No. 14/640,817, entitled INTERACTIVE FEEDBACK SYSTEM FOR POWERED SURGICAL INSTRUMENTS, now U.S. Pat. No. 9,924,961;

U.S. patent application Ser. No. 14/640,844, entitled CONTROL TECHNIQUES AND SUB-PROCESSOR CONTAINED WITHIN MODULAR SHAFT WITH SELECT CONTROL PROCESSING FROM HANDLE, now U.S. Pat. No. 10,045,776;

U.S. patent application Ser. No. 14/640,837, entitled SMART SENSORS WITH LOCAL SIGNAL PROCESSING, now U.S. Pat. No. 9,993,248;

U.S. patent application Ser. No. 14/640,765, entitled SYSTEM FOR DETECTING THE MIS-INSERTION OF A STAPLE CARTRIDGE INTO A SURGICAL STAPLER, now U.S. Patent Application Publication No. 2016/0256160;

U.S. patent application Ser. No. 14/640,799, entitled SIGNAL AND POWER COMMUNICATION SYSTEM POSITIONED ON A ROTATABLE SHAFT, now U.S. Pat. No. 9,901,342; and U.S. patent application Ser. No. 14/640,780, entitled SURGICAL INSTRUMENT COMPRISING A LOCKABLE BATTERY HOUSING, now U.S. Pat. No. 10,245,033.

Applicant of the present application owns the following patent applications that were filed on Feb. 27, 2015, and which are each herein incorporated by reference in their respective entirety:

U.S. patent application Ser. No. 14/633,576, entitled SURGICAL INSTRUMENT SYSTEM COMPRISING AN INSPECTION STATION, now U.S. Pat. No. 10,045,779;

U.S. patent application Ser. No. 14/633,546, entitled SURGICAL APPARATUS CONFIGURED TO ASSESS WHETHER A PERFORMANCE PARAMETER OF THE SURGICAL APPARATUS IS WITHIN AN ACCEPTABLE PERFORMANCE BAND, now U.S. Pat. No. 10,180,463;

U.S. patent application Ser. No. 14/633,560, entitled SURGICAL CHARGING SYSTEM THAT CHARGES AND/OR CONDITIONS ONE OR MORE BATTERIES, now U.S. Patent Application Publication No. 2016/0249910;

U.S. patent application Ser. No. 14/633,566, entitled CHARGING SYSTEM THAT ENABLES EMERGENCY RESOLUTIONS FOR CHARGING A BATTERY, now U.S. Pat. No. 10,182,816;

U.S. patent application Ser. No. 14/633,555, entitled SYSTEM FOR MONITORING WHETHER A SURGICAL INSTRUMENT NEEDS TO BE SERVICED, now U.S. Patent Application Publication No. 2016/0249916;

U.S. patent application Ser. No. 14/633,542, entitled REINFORCED BATTERY FOR A SURGICAL INSTRUMENT, now U.S. Pat. No. 9,931,118;

U.S. patent application Ser. No. 14/633,548, entitled POWER ADAPTER FOR A SURGICAL INSTRUMENT, now U.S. Pat. No. 10,245,028;

U.S. patent application Ser. No. 14/633,526, entitled ADAPTABLE SURGICAL INSTRUMENT HANDLE, now U.S. Pat. No. 9,993,258;

U.S. patent application Ser. No. 14/633,541, entitled MODULAR STAPLING ASSEMBLY, now U.S. Pat. No. 10,226,250; and U.S. patent application Ser. No. 14/633,562, entitled SURGICAL APPARATUS CONFIGURED TO TRACK AN END-OF-LIFE PARAMETER, now U.S. Pat. No. 10,159,483.

Applicant of the present application owns the following patent applications that were filed on Dec. 18, 2014 and which are each herein incorporated by reference in their respective entirety:

U.S. patent application Ser. No. 14/574,478, entitled SURGICAL INSTRUMENT SYSTEMS COMPRISING AN ARTICULATABLE END EFFECTOR AND MEANS FOR ADJUSTING THE FIRING STROKE OF A FIRING MEMBER, now U.S. Pat. No. 9,844,374;

U.S. patent application Ser. No. 14/574,483, entitled SURGICAL INSTRUMENT ASSEMBLY COMPRISING LOCKABLE SYSTEMS, now U.S. Pat. No. 10,188,385;

U.S. patent application Ser. No. 14/575,139, entitled DRIVE ARRANGEMENTS FOR ARTICULATABLE SURGICAL INSTRUMENTS, now U.S. Pat. No. 9,844,375;

U.S. patent application Ser. No. 14/575,148, entitled LOCKING ARRANGEMENTS FOR DETACHABLE SHAFT ASSEMBLIES WITH ARTICULATABLE SURGICAL END EFFECTORS, now U.S. Pat. No. 10,085,748;

U.S. patent application Ser. No. 14/575,130, entitled SURGICAL INSTRUMENT WITH AN ANVIL THAT IS SELECTIVELY MOVABLE ABOUT A DISCRETE NON-MOVABLE AXIS RELATIVE TO A STAPLE CARTRIDGE, now U.S. Pat. No. 10,245,027;

U.S. patent application Ser. No. 14/575,143, entitled SURGICAL INSTRUMENTS WITH IMPROVED CLOSURE ARRANGEMENTS, now U.S. Pat. No. 10,004,501;

U.S. patent application Ser. No. 14/575,117, entitled SURGICAL INSTRUMENTS WITH ARTICULATABLE END EFFECTORS AND MOVABLE FIRING BEAM SUPPORT ARRANGEMENTS, now U.S. Pat. No. 9,943,309;

U.S. patent application Ser. No. 14/575,154, entitled SURGICAL INSTRUMENTS WITH ARTICULATABLE END EFFECTORS AND IMPROVED FIRING BEAM SUPPORT ARRANGEMENTS, now U.S. Pat. No. 9,968,355;

U.S. patent application Ser. No. 14/574,493, entitled SURGICAL INSTRUMENT ASSEMBLY COMPRISING A FLEXIBLE ARTICULATION SYSTEM, now U.S. Pat. No. 9,987,000; and U.S. patent application Ser. No. 14/574,500, entitled SURGICAL INSTRUMENT ASSEMBLY COMPRISING A LOCKABLE ARTICULATION SYSTEM, now U.S. Pat. No. 10,117,649.

Applicant of the present application owns the following patent applications that were filed on Mar. 1, 2013 and which are each herein incorporated by reference in their respective entirety:

U.S. patent application Ser. No. 13/782,295, entitled Articulatable Surgical Instruments With Conductive Pathways For Signal Communication, now U.S. Pat. No. 9,700,309;

U.S. patent application Ser. No. 13/782,323, entitled Rotary Powered Articulation Joints For Surgical Instruments, now U.S. Pat. No. 9,782,169;

U.S. patent application Ser. No. 13/782,338, entitled Thumbwheel Switch Arrangements For Surgical Instruments, now U.S. Patent Application Publication No. 2014/0249557;

U.S. patent application Ser. No. 13/782,499, entitled Electromechanical Surgical Device with Signal Relay Arrangement, now U.S. Pat. No. 9,358,003;

U.S. patent application Ser. No. 13/782,460, entitled Multiple Processor Motor Control for Modular Surgical Instruments, now U.S. Pat. No. 9,554,794;

U.S. patent application Ser. No. 13/782,358, entitled Joystick Switch Assemblies For Surgical Instruments, now U.S. Pat. No. 9,326,767;

U.S. patent application Ser. No. 13/782,481, entitled Sensor Straightened End Effector During Removal Through Trocar, now U.S. Pat. No. 9,468,438;

U.S. patent application Ser. No. 13/782,518, entitled Control Methods for Surgical Instruments with Removable Implement Portions, now U.S. Patent Application Publication No. 2014/0246475;

U.S. patent application Ser. No. 13/782,375, entitled Rotary Powered Surgical Instruments With Multiple Degrees of Freedom, now U.S. Pat. No. 9,398,911; and U.S. patent application Ser. No. 13/782,536, entitled Surgical Instrument Soft Stop, now U.S. Pat. No. 9,307,986.

Applicant of the present application also owns the following patent applications that were filed on Mar. 14, 2013 and which are each herein incorporated by reference in their respective entirety:

U.S. patent application Ser. No. 13/803,097, entitled ARTICULATABLE SURGICAL INSTRUMENT COMPRISING A FIRING DRIVE, now U.S. Pat. No. 9,687,230;

U.S. patent application Ser. No. 13/803,193, entitled CONTROL ARRANGEMENTS FOR A DRIVE MEMBER OF A SURGICAL INSTRUMENT, now U.S. Pat. No. 9,332,987;

U.S. patent application Ser. No. 13/803,053, entitled INTERCHANGEABLE SHAFT ASSEMBLIES FOR USE WITH A SURGICAL INSTRUMENT, now U.S. Pat. No. 9,883,860;

U.S. patent application Ser. No. 13/803,086, entitled ARTICULATABLE SURGICAL INSTRUMENT COMPRISING AN ARTICULATION LOCK, now U.S. Patent Application Publication No. 2014/0263541;

U.S. patent application Ser. No. 13/803,210, entitled SENSOR ARRANGEMENTS FOR ABSOLUTE POSITIONING SYSTEM FOR SURGICAL INSTRUMENTS, now U.S. Pat. No. 9,808,244;

U.S. patent application Ser. No. 13/803,148, entitled MULTI-FUNCTION MOTOR FOR A SURGICAL INSTRUMENT, now U.S. Patent Application Publication No. 2014/0263554;

U.S. patent application Ser. No. 13/803,066, entitled DRIVE SYSTEM LOCKOUT ARRANGEMENTS FOR MODULAR SURGICAL INSTRUMENTS, now U.S. Pat. No. 9,629,623;

U.S. patent application Ser. No. 13/803,117, entitled ARTICULATION CONTROL SYSTEM FOR ARTICULATABLE SURGICAL INSTRUMENTS, now U.S. Pat. No. 9,351,726;

U.S. patent application Ser. No. 13/803,130, entitled DRIVE TRAIN CONTROL ARRANGEMENTS FOR MODULAR SURGICAL INSTRUMENTS, now U.S. Pat. No. 9,351,727; and U.S. patent application Ser. No. 13/803,159, entitled METHOD AND SYSTEM FOR OPERATING A SURGICAL INSTRUMENT, now U.S. Pat. No. 9,888,919.

Applicant of the present application also owns the following patent application that was filed on Mar. 7, 2014 and is herein incorporated by reference in its entirety:

U.S. patent application Ser. No. 14/200,111, entitled CONTROL SYSTEMS FOR SURGICAL INSTRUMENTS, now U.S. Pat. No. 9,629,629.

Applicant of the present application also owns the following patent applications that were filed on Mar. 26, 2014 and are each herein incorporated by reference in their respective entirety:

U.S. patent application Ser. No. 14/226,106, entitled POWER MANAGEMENT CONTROL SYSTEMS FOR SURGICAL INSTRUMENTS, now U.S. Patent Application Publication No. 2015/0272582;

U.S. patent application Ser. No. 14/226,099, entitled STERILIZATION VERIFICATION CIRCUIT, now U.S. Pat. No. 9,826,977;

U.S. patent application Ser. No. 14/226,094, entitled VERIFICATION OF NUMBER OF BATTERY EXCHANGES/PROCEDURE COUNT, now U.S. Patent Application Publication No. 2015/0272580;

U.S. patent application Ser. No. 14/226,117, entitled POWER MANAGEMENT THROUGH SLEEP OPTIONS OF SEGMENTED CIRCUIT AND WAKE UP CONTROL, now U.S. Pat. No. 10,013,049;

U.S. patent application Ser. No. 14/226,075, entitled MODULAR POWERED SURGICAL INSTRUMENT WITH DETACHABLE SHAFT ASSEMBLIES, now U.S. Pat. No. 9,743,929;

U.S. patent application Ser. No. 14/226,093, entitled FEEDBACK ALGORITHMS FOR MANUAL BAILOUT SYSTEMS FOR SURGICAL INSTRUMENTS, now U.S. Pat. No. 10,028,761;

U.S. patent application Ser. No. 14/226,116, entitled SURGICAL INSTRUMENT UTILIZING SENSOR ADAPTATION, now U.S. Patent Application Publication No. 2015/0272571;

U.S. patent application Ser. No. 14/226,071, entitled SURGICAL INSTRUMENT CONTROL CIRCUIT HAVING A SAFETY PROCESSOR, now U.S. Pat. No. 9,690,362;

U.S. patent application Ser. No. 14/226,097, entitled SURGICAL INSTRUMENT COMPRISING INTERACTIVE SYSTEMS, now U.S. Pat. No. 9,820,738;

U.S. patent application Ser. No. 14/226,126, entitled INTERFACE SYSTEMS FOR USE WITH SURGICAL INSTRUMENTS, now U.S. Pat. No. 10,004,497;

U.S. patent application Ser. No. 14/226,133, entitled MODULAR SURGICAL INSTRUMENT SYSTEM, now U.S. Patent Application Publication No. 2015/0272557;

U.S. patent application Ser. No. 14/226,081, entitled SYSTEMS AND METHODS FOR CONTROLLING A SEGMENTED CIRCUIT, now U.S. Pat. No. 9,804,618;

U.S. patent application Ser. No. 14/226,076, entitled POWER MANAGEMENT THROUGH SEGMENTED CIRCUIT AND VARIABLE VOLTAGE PROTECTION, now U.S. Pat. No. 9,733,663;

U.S. patent application Ser. No. 14/226,111, entitled SURGICAL STAPLING INSTRUMENT SYSTEM, now U.S. Pat. No. 9,750,499; and U.S. patent application Ser. No. 14/226,125, entitled SURGICAL INSTRUMENT COMPRISING A ROTATABLE SHAFT, now U.S. Pat. No. 10,201,364.

Applicant of the present application also owns the following patent applications that were filed on Sep. 5, 2014 and which are each herein incorporated by reference in their respective entirety:

U.S. patent application Ser. No. 14/479,103, entitled CIRCUITRY AND SENSORS FOR POWERED MEDICAL DEVICE, now U.S. Pat. No. 10,111,679;

U.S. patent application Ser. No. 14/479,119, entitled ADJUNCT WITH INTEGRATED SENSORS TO QUANTIFY TISSUE COMPRESSION, now U.S. Pat. No. 9,724,094;

U.S. patent application Ser. No. 14/478,908, entitled MONITORING DEVICE DEGRADATION BASED ON COMPONENT EVALUATION, now U.S. Pat. No. 9,737,301;

U.S. patent application Ser. No. 14/478,895, entitled MULTIPLE SENSORS WITH ONE SENSOR AFFECTING A SECOND SENSOR'S OUTPUT OR INTERPRETATION, now U.S. Pat. No. 9,757,128;

U.S. patent application Ser. No. 14/479,110, entitled POLARITY OF HALL MAGNET TO IDENTIFY CARTRIDGE TYPE, now U.S. Pat. No. 10,016,199;

U.S. patent application Ser. No. 14/479,098, entitled SMART CARTRIDGE WAKE UP OPERATION AND DATA RETENTION, now U.S. Pat. No. 10,135,242;

U.S. patent application Ser. No. 14/479,115, entitled MULTIPLE MOTOR CONTROL FOR POWERED MEDICAL DEVICE, now U.S. Pat. No. 9,788,836; and U.S. patent application Ser. No. 14/479,108, entitled LOCAL DISPLAY OF TISSUE PARAMETER STABILIZATION, now U.S. Patent Application Publication No. 2016/0066913.

Applicant of the present application also owns the following patent applications that were filed on Apr. 9, 2014 and which are each herein incorporated by reference in their respective entirety:

U.S. patent application Ser. No. 14/248,590, entitled MOTOR DRIVEN SURGICAL INSTRUMENTS WITH LOCKABLE DUAL DRIVE SHAFTS, now U.S. Pat. No. 9,826,976;

U.S. patent application Ser. No. 14/248,581, entitled SURGICAL INSTRUMENT COMPRISING A CLOSING DRIVE AND A FIRING DRIVE OPERATED FROM THE SAME ROTATABLE OUTPUT, now U.S. Pat. No. 9,649,110;

U.S. patent application Ser. No. 14/248,595, entitled SURGICAL SYSTEM COMPRISING FIRST AND SECOND DRIVE SYSTEMS, now U.S. Pat. No. 9,844,368;

U.S. patent application Ser. No. 14/248,588, entitled POWERED LINEAR SURGICAL STAPLER, now U.S. Patent Application Publication No. 2014/0309666;

U.S. patent application Ser. No. 14/248,591, entitled SURGICAL INSTRUMENT COMPRISING A GAP SETTING SYSTEM, now U.S. Pat. No. 10,149,680;

U.S. patent application Ser. No. 14/248,584, entitled MODULAR MOTOR DRIVEN SURGICAL INSTRUMENTS WITH ALIGNMENT FEATURES FOR ALIGNING ROTARY DRIVE SHAFTS WITH SURGICAL END EFFECTOR SHAFTS, now U.S. Pat. No. 9,801,626;

U.S. patent application Ser. No. 14/248,587, entitled POWERED SURGICAL STAPLER, now U.S. Pat. No. 9,867,612;

U.S. patent application Ser. No. 14/248,586, entitled DRIVE SYSTEM DECOUPLING ARRANGEMENT FOR A SURGICAL INSTRUMENT, now U.S. Pat. No. 10,136,887; and U.S. patent application Ser. No. 14/248,607, entitled MODULAR MOTOR DRIVEN SURGICAL INSTRUMENTS WITH STATUS INDICATION ARRANGEMENTS, now U.S. Pat. No. 9,814,460.

Applicant of the present application also owns the following patent applications that were filed on Apr. 16, 2013 and which are each herein incorporated by reference in their respective entirety:

U.S. Provisional Patent Application Ser. No. 61/812,365, entitled SURGICAL INSTRUMENT WITH MULTIPLE FUNCTIONS PERFORMED BY A SINGLE MOTOR;

U.S. Provisional Patent Application Ser. No. 61/812,376, entitled LINEAR CUTTER WITH POWER;

U.S. Provisional Patent Application Ser. No. 61/812,382, entitled LINEAR CUTTER WITH MOTOR AND PISTOL GRIP;

U.S. Provisional Patent Application Ser. No. 61/812,385, entitled SURGICAL INSTRUMENT HANDLE WITH MULTIPLE ACTUATION MOTORS AND MOTOR CONTROL; and U.S. Provisional Patent Application Ser. No. 61/812,372, entitled SURGICAL INSTRUMENT WITH MULTIPLE FUNCTIONS PERFORMED BY A SINGLE MOTOR.

Applicant of the present application owns the following U.S. Provisional Patent Applications, filed on Dec. 28, 2017, the disclosure of each of which is herein incorporated by reference in its entirety:

U.S. Provisional Patent Application Ser. No. 62/611,341, entitled INTERACTIVE SURGICAL PLATFORM;

U.S. Provisional Patent Application Ser. No. 62/611,340, entitled CLOUD-BASED MEDICAL ANALYTICS; and U.S. Provisional Patent Application Ser. No. 62/611,339, entitled ROBOT ASSISTED SURGICAL PLATFORM.

Applicant of the present application owns the following U.S. Provisional Patent Applications, filed on Mar. 28, 2018, each of which is herein incorporated by reference in its entirety:

U.S. Provisional Patent Application Ser. No. 62/649,302, entitled INTERACTIVE SURGICAL SYSTEMS WITH encrypted COMMUNICATION CAPABILITIES;

U.S. Provisional Patent Application Ser. No. 62/649,294, entitled DATA STRIPPING METHOD TO INTERROGATE PATIENT RECORDS AND CREATE ANONYMIZED RECORD;

U.S. Provisional Patent Application Ser. No. 62/649,300, entitled SURGICAL HUB SITUATIONAL AWARENESS;

U.S. Provisional Patent Application Ser. No. 62/649,309, entitled SURGICAL HUB SPATIAL AWARENESS TO DETERMINE DEVICES IN OPERATING THEATER;

U.S. Provisional Patent Application Ser. No. 62/649,310, entitled COMPUTER IMPLEMENTED INTERACTIVE SURGICAL SYSTEMS;

U.S. Provisional Patent Application Ser. No. 62/649,291, entitled USE OF LASER LIGHT AND RED-GREEN-BLUE COLORATION TO DETERMINE PROPERTIES OF BACK SCATTERED LIGHT;

U.S. Provisional Patent Application Ser. No. 62/649,296, entitled ADAPTIVE CONTROL PROGRAM UPDATES FOR SURGICAL DEVICES;

U.S. Provisional Patent Application Ser. No. 62/649,333, entitled CLOUD-BASED MEDICAL ANALYTICS FOR CUSTOMIZATION AND RECOMMENDATIONS TO A USER;

U.S. Provisional Patent Application Ser. No. 62/649,327, entitled CLOUD-BASED MEDICAL ANALYTICS FOR SECURITY AND AUTHENTICATION TRENDS AND REACTIVE MEASURES;

U.S. Provisional Patent Application Ser. No. 62/649,315, entitled DATA HANDLING AND PRIORITIZATION IN A CLOUD ANALYTICS NETWORK;

U.S. Provisional Patent Application Ser. No. 62/649,313, entitled CLOUD INTERFACE FOR COUPLED SURGICAL DEVICES;

U.S. Provisional Patent Application Ser. No. 62/649,320, entitled DRIVE ARRANGEMENTS FOR ROBOT-ASSISTED SURGICAL PLATFORMS;

U.S. Provisional Patent Application Ser. No. 62/649,307, entitled AUTOMATIC TOOL ADJUSTMENTS FOR ROBOT-ASSISTED SURGICAL PLATFORMS; and U.S. Provisional Patent Application Ser. No. 62/649,323, entitled SENSING ARRANGEMENTS FOR Robot-Assisted Surgical PlatformS.

Applicant of the present application owns the following U.S. Patent Applications, filed on Mar. 29, 2018, each of which is herein incorporated by reference in its entirety:

U.S. patent application Ser. No. 15/940,641, entitled INTERACTIVE SURGICAL SYSTEMS WITH encrypted COMMUNICATION CAPABILITIES;

U.S. patent application Ser. No. 15/940,648, entitled INTERACTIVE SURGICAL SYSTEMS WITH CONDITION HANDLING OF DEVICES AND DATA CAPABILITIES;

U.S. patent application Ser. No. 15/940,656, entitled Surgical hub coordination of control and communication of operating room devices;

U.S. patent application Ser. No. 15/940,666, entitled Spatial awareness of surgical hubs in operating rooms;

U.S. patent application Ser. No. 15/940,670, entitled Cooperative utilization of data derived from secondary sources by intelligent surgical hubs;

U.S. patent application Ser. No. 15/940,677, entitled Surgical hub control arrangements;

U.S. patent application Ser. No. 15/940,632, entitled DATA STRIPPING METHOD TO INTERROGATE PATIENT RECORDS AND CREATE ANONYMIZED RECORD;

U.S. patent application Ser. No. 15/940,640, entitled COMMUNICATION HUB AND STORAGE DEVICE FOR STORING PARAMETERS AND STATUS OF A SURGICAL DEVICE TO BE SHARED WITH CLOUD BASED ANALYTICS SYSTEMS;

U.S. patent application Ser. No. 15/940,645, entitled SELF DESCRIBING DATA PACKETS GENERATED AT AN ISSUING INSTRUMENT;

U.S. patent application Ser. No. 15/940,649, entitled DATA PAIRING TO INTERCONNECT A DEVICE MEASURED PARAMETER WITH AN OUTCOME;

U.S. patent application Ser. No. 15/940,654, entitled SURGICAL HUB SITUATIONAL AWARENESS;

U.S. patent application Ser. No. 15/940,663, entitled SURGICAL SYSTEM DISTRIBUTED PROCESSING;

U.S. patent application Ser. No. 15/940,668, entitled AGGREGATION AND REPORTING OF SURGICAL HUB DATA;

U.S. patent application Ser. No. 15/940,671, entitled SURGICAL HUB SPATIAL AWARENESS TO DETERMINE DEVICES IN OPERATING THEATER;

U.S. patent application Ser. No. 15/940,686, entitled DISPLAY OF ALIGNMENT OF STAPLE CARTRIDGE TO PRIOR LINEAR STAPLE LINE;

U.S. patent application Ser. No. 15/940,700, entitled STERILE FIELD INTERACTIVE CONTROL DISPLAYS;

U.S. patent application Ser. No. 15/940,629, entitled COMPUTER IMPLEMENTED INTERACTIVE SURGICAL SYSTEMS;

U.S. patent application Ser. No. 15/940,704, entitled USE OF LASER LIGHT AND RED-GREEN-BLUE COLORATION TO DETERMINE PROPERTIES OF BACK SCATTERED LIGHT;

U.S. patent application Ser. No. 15/940,722, entitled CHARACTERIZATION OF TISSUE IRREGULARITIES THROUGH THE USE OF MONO-CHROMATIC LIGHT REFRACTIVITY; and U.S. patent application Ser. No. 15/940,742, entitled DUAL CMOS ARRAY IMAGING.

Applicant of the present application owns the following U.S. Patent Applications, filed on Mar. 29, 2018, each of which is herein incorporated by reference in its entirety:

U.S. patent application Ser. No. 15/940,636, entitled ADAPTIVE CONTROL PROGRAM UPDATES FOR SURGICAL DEVICES;

U.S. patent application Ser. No. 15/940,653, entitled ADAPTIVE CONTROL PROGRAM UPDATES FOR SURGICAL HUBS;

U.S. patent application Ser. No. 15/940,660, entitled CLOUD-BASED MEDICAL ANALYTICS FOR CUSTOMIZATION AND RECOMMENDATIONS TO A USER;

U.S. patent application Ser. No. 15/940,679, entitled CLOUD-BASED MEDICAL ANALYTICS FOR LINKING OF LOCAL USAGE TRENDS WITH THE RESOURCE ACQUISITION BEHAVIORS OF LARGER DATA SET;

U.S. patent application Ser. No. 15/940,694, entitled Cloud-based Medical Analytics for Medical Facility Segmented Individualization of Instrument Function;

U.S. patent application Ser. No. 15/940,634, entitled CLOUD-BASED MEDICAL ANALYTICS FOR SECURITY AND AUTHENTICATION TRENDS AND REACTIVE MEASURES;

U.S. patent application Ser. No. 15/940,706, entitled DATA HANDLING AND PRIORITIZATION IN A CLOUD ANALYTICS NETWORK; and U.S. patent application Ser. No. 15/940,675, entitled CLOUD INTERFACE FOR COUPLED SURGICAL DEVICES.

Applicant of the present application owns the following U.S. Patent Applications, filed on Mar. 29, 2018, each of which is herein incorporated by reference in its entirety:

U.S. patent application Ser. No. 15/940,627, entitled DRIVE ARRANGEMENTS FOR ROBOT-AS-SISTED SURGICAL PLATFORMS;

U.S. patent application Ser. No. 15/940,637, entitled COMMUNICATION ARRANGEMENTS FOR ROBOT-ASSISTED SURGICAL PLATFORMS;

U.S. patent application Ser. No. 15/940,642, entitled CONTROLS FOR ROBOT-ASSISTED SURGICAL PLATFORMS;

U.S. patent application Ser. No. 15/940,676, entitled AUTOMATIC TOOL ADJUSTMENTS FOR ROBOT-ASSISTED SURGICAL PLATFORMS;

U.S. patent application Ser. No. 15/940,680, entitled CONTROLLERS FOR ROBOT-ASSISTED SURGI-CAL PLATFORMS;

U.S. patent application Ser. No. 15/940,683, entitled COOPERATIVE SURGICAL ACTIONS FOR ROBOT-ASSISTED SURGICAL PLATFORMS;

U.S. patent application Ser. No. 15/940,690, entitled DISPLAY ARRANGEMENTS FOR ROBOT-AS-SISTED SURGICAL PLATFORMS; and U.S. patent application Ser. No. 15/940,711, entitled SENSING ARRANGEMENTS FOR Robot-Assisted Surgical Platforms.

Applicant of the present application owns the following U.S. Patent Applications that were filed on Jun. 30, 2019 and which are each herein incorporated by reference in their respective entireties:

U.S. patent application Ser. No. 16/458,104, entitled METHOD FOR AUTHENTICATING THE COMPAT-IBILITY OF A STAPLE CARTRIDGE WITH A SUR-GICAL INSTRUMENT, now U.S. Patent Application Publication No. 2020/0405301;

U.S. patent application Ser. No. 16/458,108, entitled SURGICAL INSTRUMENT SYSTEM COMPRIS-ING AN RFID SYSTEM, now U.S. Patent Application Publication No. 2020/0405436;

U.S. patent application Ser. No. 16/458,111, entitled SURGICAL INSTRUMENT COMPRISING AN RFID SYSTEM FOR TRACKING A MOVABLE COMPONENT, now U.S. Patent Application Publica-tion No. 2020/0405437;

U.S. patent application Ser. No. 16/458,114, entitled SURGICAL INSTRUMENT COMPRISING AN ALIGNED RFID SENSOR, now U.S. Patent Applica-tion Publication No. 2020/0405438;

U.S. patent application Ser. No. 16/458,105, entitled SURGICAL STAPLING SYSTEM HAVING AN INFORMATION DECRYPTION PROTOCOL, now U.S. Patent Application Publication No. 2020/0405302;

U.S. patent application Ser. No. 16/458,110, entitled SURGICAL STAPLING SYSTEM HAVING AN INFORMATION ENCRYPTION PROTOCOL, now U.S. Patent Application Publication No. 2020/0405297;

U.S. patent application Ser. No. 16/458,120, entitled SURGICAL STAPLING SYSTEM HAVING A LOCKOUT MECHANISM FOR AN INCOMPAT-IBLE CARTRIDGE, now U.S. Patent Application Pub-lication No. 2020/0405303;

U.S. patent application Ser. No. 16/458,125, entitled SURGICAL STAPLING SYSTEM HAVING A FRANGIBLE RFID TAG, now U.S. Patent Application Publication No. 2020/0405441; and U.S. patent application Ser. No. 16/458,103, entitled PACKAGING FOR A REPLACEABLE COMPO-NENT OF A SURGICAL STAPLING SYSTEM, now U.S. Patent Application Publication No. 2020/0405296.

Applicant of the present application owns the following U.S. Patent Applications that were filed on Jun. 30, 2019 and which are each herein incorporated by reference in their respective entireties:

U.S. patent application Ser. No. 16/458,107, entitled METHOD OF USING MULTIPLE RFID CHIPS WITH A SURGICAL ASSEMBLY, now U.S. Patent Application Publication No. 2020/0405311;

U.S. patent application Ser. No. 16/458,109, entitled MECHANISMS FOR PROPER ANVIL ATTACH-MENT SURGICAL STAPLING HEAD ASSEMBLY, now U.S. Patent Application Publication No. 2020/0405312;

U.S. patent application Ser. No. 16/458,119, entitled MECHANISMS FOR MOTOR CONTROL ADJUST-MENTS OF A MOTORIZED SURGICAL INSTRU-MENT, now U.S. Patent Application Publication No. 2020/0405314;

U.S. patent application Ser. No. 16/458,115, entitled SURGICAL INSTRUMENT WITH BATTERY COM-PATIBILITY VERIFICATION FUNCTIONALITY, now U.S. Patent Application Publication No. 2020/0405313;

U.S. patent application Ser. No. 16/458,117, entitled SURGICAL SYSTEM WITH RFID TAGS FOR UPDATING MOTOR ASSEMBLY PARAMETERS, now U.S. Patent Application Publication No. 2020/0405439;

U.S. patent application Ser. No. 16/458,121, entitled SURGICAL SYSTEMS WITH MULTIPLE RFID TAGS, now U.S. Patent Application Publication No. 2020/0405440;

U.S. patent application Ser. No. 16/458,122, entitled RFID IDENTIFICATION SYSTEMS FOR SURGI-CAL INSTRUMENTS, now U.S. Patent Application Publication No. 2020/0410177;

U.S. patent application Ser. No. 16/458,106, entitled RFID IDENTIFICATION SYSTEMS FOR SURGI-CAL INSTRUMENTS, now U.S. Patent Application Publication No. 2020/0405316;

U.S. patent application Ser. No. 16/458,112, entitled SURGICAL RFID ASSEMBLIES FOR DISPLAY AND COMMUNICATION, now U.S. Patent Applica-tion Publication No. 2020/0405409;

U.S. patent application Ser. No. 16/458,116, entitled SURGICAL RFID ASSEMBLIES FOR COMPAT-IBILITY DETECTION, now U.S. Patent Application Publication No. 2020/0410180; and U.S. patent application Ser. No. 16/458,118, entitled SURGICAL RFID ASSEMBLIES FOR INSTRU-MENT OPERATIONAL SETTING CONTROL, now U.S. Patent Application Publication No. 2020/0405410.

Numerous specific details are set forth to provide a thorough understanding of the overall structure, function, manufacture, and use of the embodiments as described in the specification and illustrated in the accompanying drawings. Well-known operations, components, and elements have not been described in detail so as not to obscure the embodi-ments described in the specification. The reader will under-stand that the embodiments described and illustrated herein are non-limiting examples, and thus it can be appreciated that the specific structural and functional details disclosed herein may be representative and illustrative. Variations and changes thereto may be made without departing from the scope of the claims.

The terms "comprise" (and any form of comprise, such as "comprises" and "comprising"), "have" (and any form of have, such as "has" and "having"), "include" (and any form of include, such as "includes" and "including") and "contain" (and any form of contain, such as "contains" and "containing") are open-ended linking verbs. As a result, a surgical system, device, or apparatus that "comprises," "has," "includes" or "contains" one or more elements possesses those one or more elements, but is not limited to possessing only those one or more elements. Likewise, an element of a system, device, or apparatus that "comprises," "has," "includes" or "contains" one or more features possesses those one or more features, but is not limited to possessing only those one or more features.

The terms "proximal" and "distal" are used herein with reference to a clinician manipulating the handle portion of the surgical instrument. The term "proximal" refers to the portion closest to the clinician and the term "distal" refers to the portion located away from the clinician. It will be further appreciated that, for convenience and clarity, spatial terms such as "vertical", "horizontal", "up", and "down" may be used herein with respect to the drawings. However, surgical instruments are used in many orientations and positions, and these terms are not intended to be limiting and/or absolute.

Various exemplary devices and methods are provided for performing laparoscopic and minimally invasive surgical procedures. However, the reader will readily appreciate that the various methods and devices disclosed herein can be used in numerous surgical procedures and applications including, for example, in connection with open surgical procedures. As the present Detailed Description proceeds, the reader will further appreciate that the various instruments disclosed herein can be inserted into a body in any way, such as through a natural orifice, through an incision or puncture hole formed in tissue, etc. The working portions or end effector portions of the instruments can be inserted directly into a patient's body or can be inserted through an access device that has a working channel through which the end effector and elongate shaft of a surgical instrument can be advanced.

A surgical stapling system can comprise a shaft and an end effector extending from the shaft. The end effector comprises a first jaw and a second jaw. The first jaw comprises a staple cartridge. The staple cartridge is insertable into and removable from the first jaw; however, other embodiments are envisioned in which a staple cartridge is not removable from, or at least readily replaceable from, the first jaw. The second jaw comprises an anvil configured to deform staples ejected from the staple cartridge. The second jaw is pivotable relative to the first jaw about a closure axis; however, other embodiments are envisioned in which the first jaw is pivotable relative to the second jaw. The surgical stapling system further comprises an articulation joint configured to permit the end effector to be rotated, or articulated, relative to the shaft. The end effector is rotatable about an articulation axis extending through the articulation joint. Other embodiments are envisioned which do not include an articulation joint.

The staple cartridge comprises a cartridge body. The cartridge body includes a proximal end, a distal end, and a deck extending between the proximal end and the distal end. In use, the staple cartridge is positioned on a first side of the tissue to be stapled and the anvil is positioned on a second side of the tissue. The anvil is moved toward the staple cartridge to compress and clamp the tissue against the deck. Thereafter, staples removably stored in the cartridge body can be deployed into the tissue. The cartridge body includes staple cavities defined therein wherein staples are removably stored in the staple cavities. The staple cavities are arranged in six longitudinal rows. Three rows of staple cavities are positioned on a first side of a longitudinal slot and three rows of staple cavities are positioned on a second side of the longitudinal slot. Other arrangements of staple cavities and staples may be possible.

The staples are supported by staple drivers in the cartridge body. The drivers are movable between a first, or unfired position, and a second, or fired, position to eject the staples from the staple cavities. The drivers are retained in the cartridge body by a retainer which extends around the bottom of the cartridge body and includes resilient members configured to grip the cartridge body and hold the retainer to the cartridge body. The drivers are movable between their unfired positions and their fired positions by a sled. The sled is movable between a proximal position adjacent the proximal end and a distal position adjacent the distal end. The sled comprises a plurality of ramped surfaces configured to slide under the drivers and lift the drivers, and the staples supported thereon, toward the anvil.

Further to the above, the sled is moved distally by a firing member. The firing member is configured to contact the sled and push the sled toward the distal end. The longitudinal slot defined in the cartridge body is configured to receive the firing member. The anvil also includes a slot configured to receive the firing member. The firing member further comprises a first cam which engages the first jaw and a second cam which engages the second jaw. As the firing member is advanced distally, the first cam and the second cam can control the distance, or tissue gap, between the deck of the staple cartridge and the anvil. The firing member also comprises a knife configured to incise the tissue captured intermediate the staple cartridge and the anvil. It is desirable for the knife to be positioned at least partially proximal to the ramped surfaces such that the staples are ejected ahead of the knife.

Before explaining various aspects of surgical devices and generators in detail, it should be noted that the illustrative examples are not limited in application or use to the details of construction and arrangement of parts illustrated in the accompanying drawings and description. The illustrative examples may be implemented or incorporated in other aspects, variations and modifications, and may be practiced or carried out in various ways. Further, unless otherwise indicated, the terms and expressions employed herein have been chosen for the purpose of describing the illustrative examples for the convenience of the reader and are not for the purpose of limitation thereof. Also, it will be appreciated that one or more of the following-described aspects, expressions of aspects, and/or examples, can be combined with any one or more of the other following-described aspects, expressions of aspects and/or examples.

Certain exemplary embodiments will now be described to provide an overall understanding of the principles of the structure, function, manufacture, and use of the devices and methods disclosed herein. One or more examples of these exemplary embodiments are illustrated in the accompanying drawings. Those of ordinary skill in the art will understand that the devices and methods specifically described herein and illustrated in the accompanying drawings are non-limiting exemplary embodiments and that the scope of the various exemplary embodiments of the present invention is defined solely by the claims. The features illustrated or described in connection with one exemplary embodiment may be combined with the features of other exemplary embodiments. Such modifications and variations are intended to be included within the scope of the present invention.

FIGS. 1-5 depict a surgical stapling instrument 1000 configured to cut and staple tissue of a patient. The surgical stapling instrument 1000 comprises a housing, or handle, assembly 1100, a shaft assembly 1200 attached to the handle assembly 1100, and an end effector assembly 1300. The handle assembly 1100 comprises a housing 1101 configured to house various components therein such as, for example, electronics, motors, and/or drive train components. The handle assembly 1100 comprises a pistol grip portion 1120 comprising a handle 1121 configured to be held by a user, a closure trigger 1125 configured to clamp tissue with the end effector assembly 1300, and a firing trigger, or button, 1129 configured to cut and staple tissue with the end effector assembly 1300. The handle assembly 1100 further comprises a plurality of actuators and/or buttons 1130 configured to electronically actuate various functions of the surgical stapling instrument 1000. In at least one instance, the actuators 1130 are configured to actuate motorized articulation of the end effector assembly 1300 and/or rotation of the shaft assembly 1200 and/or end effector assembly 1300.

In at least one instance, the handle assembly 1100 comprises a plurality of motors positioned therein configured to drive one or more functions of the surgical stapling instrument 1000. The handle assembly 1100 further comprises one or more power sources such as, for example, batteries 1110 configured to power onboard electronics such as, for example, the printed circuit boards 1140, 1150 and/or power the motors positioned within the handle assembly 1100. In at least one instance, the handle assembly 1100 comprises one or more onboard memories, processors, and/or control circuits configured to analyze sensor data and/or control various electronic systems of the surgical stapling instrument such as, for example, motor control programs. The handle assembly 1100 may be in wireless communication with a surgical hub and/or various other components of a surgical operating suite to communicate various data between the handle assembly 1100 and the surgical hub, for example.

The shaft assembly 1200 is attached to the handle assembly 1100. In at least one instance, the shaft assembly 1200 is modular and can be replaced with another shaft assembly of another surgical instrument attachment, for example. In at least one instance, the shaft assembly 1200 comprises one or more of the printed circuit boards 1140, 1150. The shaft assembly 1200 is configured to house a plurality of components of the surgical stapling instrument 1000 such as, for example, drive shafts, electronics, sensors, wires, and/or frame components, for example. Such components are configured to be coupled to corresponding components positioned within the handle assembly 1100 such as, for example, motors, supply leads, wires, and/or drive train components, for example. The shaft assembly 1200 houses such components and transfers such components to the end effector assembly 1300 to drive various functions of the shaft assembly 1200 and/or end effector assembly 1300 and/or transfer electrical signals between the shaft assembly 1200 and the end effector assembly 1300 and to/from the handle assembly 1100, for example. The shaft assembly 1200 comprises electrical leads 1160 electrically coupled with one or more of the printed circuit boards 1140, 1150 and one or more components within the shaft assembly 1200 and/or the end effector assembly 1300.

The shaft assembly 1200 comprises a proximal attachment portion 1220, a primary outer shaft 1210, and an articulation joint 1230. The end effector assembly 1300 is articulatable relative to the shaft 1210 by way of the articulation joint 1230. The end effector assembly 1300 is articulatable about the articulation axis AA (FIG. 1). In at least one instance, the end effector assembly 1300 and shaft assembly 1200 are configured to be inserted through a trocar penetrating into a patient's body cavity to clamp, staple, and cut tissue of a patient. In at least one instance, the proximal attachment portion 1220 comprises one or more contacts configured to transmit electrical signals, power and/or data, for example, between the end effector assembly 1300, the shaft assembly 1200, and the handle assembly 1100. In at least one instance, the contacts comprises conductor rings configured to permit rotation of the shaft assembly 1200 relative to the handle assembly 1100 about a central longitudinal axis while still permitting electrical transmission between the shaft assembly 1200 and the handle assembly 1100.

The end effector assembly 1300 comprises a first jaw 1310 and a second jaw 1340 movable relative to the first jaw 1310 to grasp and ungrasp tissue therebetween. The first jaw 1310 is fixed relative to the second jaw 1340. In at least one instance, the first jaw 1310 is not fixed and both jaws 1310, 1340 are pivotable relative to each other. The first jaw 1310 comprises a cartridge channel 1320 configured to receive a replaceable staple cartridge assembly 1330 therein. The second jaw 1340 comprises an anvil 1350 configured to clamp onto tissue upon actuation of the closure trigger 1125 and form staples removably stored within the replaceable staple cartridge assembly 1330 upon actuation of the firing trigger 1129. The end effector assembly 1300 further comprises a firing member assembly configured to be actuated through a firing stroke to deploy staples from the replaceable staple cartridge assembly 1330 and cut tissue clamped between the jaws 1310, 1340.

As discussed above, the surgical stapling instrument 1000 may comprise various electronics. Such electronics may be wireless, wired, passively powered, and/or actively powered, for example. Such electronics may be positioned within the staple cartridge assembly 1330, on one or more components of the end effector assembly 1300 such as the cartridge channel jaw 1310 and/or the anvil jaw 1340, within the shaft assembly 1200, and/or within the handle assembly 1100. In at least one instance, electrical leads may be required to traverse the articulation joint 1230. Various arrangements disclosed herein illustrate various ways of passing electrical leads through the articulation joint 1230.

The staple cartridge assembly 1330 further comprises a retainer 1400 installed on the cartridge assembly 1330. In at least one instance, the retainer 1400 is configured to maintain staples within the cartridge assembly 1330 during shipping and/or installation of the cartridge assembly 1330 into the cartridge channel 1320. The retainer 1400 is configured to be removed prior to use of the surgical stapling instrument 1000 and the cartridge assembly 1330.

In various instances, surgical stapling systems comprise reloadable staple cartridge assemblies. Staple cartridge assemblies may be replaced during one or more surgical procedures. For example, a user may replace a used staple cartridge assembly with a new staple cartridge assembly comprising the same configuration as the used staple cartridge assembly. In at least one instance, the user may replace the used staple cartridge assembly with a new staple cartridge assembly comprising a different configuration as the used staple cartridge assembly. In at least one instance, the replaceable components include also a shaft assembly in addition to the staple cartridge assembly. At any rate, detecting the type of staple cartridge assembly to be used with the surgical stapling assembly can make a user and/or a control program, for example, aware of the type of staple cartridge assembly. Such information can be utilized in several ways.

In at least one instance, information specific to each staple cartridge assembly can be communicated to a control program wirelessly. In at least one instance, RFID tags and RFID readers are employed (radio frequency identification). In at least one instance, NFC (near field communication) technology is employed. In at least one instance, a staple retainer, a device configured to be attached to a staple cartridge assembly during manufacturing configured to prevent staples from falling out of the staple cartridge assembly and/or protect the staple cartridge assembly during shipping, for example, comprises an embedded wireless tag such as, for example, an RFID tag. Embodiments disclosed herein can employ any suitable wireless identification technology including but not limited to RFID technology and NFC technology.

In at least one instance, an instrument interface comprising a surgical instrument handle and/or robotic instrument interface, for example, comprises a reader device such as, for example, an RFID reader to detect an RFID tag embedded within a staple retainer.

In at least one instance, the RFID tag comprises a passive tag. In at least one instance the RFID tag comprises an active tag. In at least one instance, the RFID tag comprises a semi passive tag. In at least one instance, the RFID tag comprises only a readable tag. In at least one instance, the RFID tag comprises a writable storage medium. In at least one instance, the frequency of operation of the RFID systems disclosed herein comprise a low frequency range, a high frequency ranges, and/or a ultrahigh frequency range. In at least one instance, the RFID technology employed herein utilizes inductive coupling and/or near field coupling. In at least one instance, the RFID technology employed herein utilizes electromagnetic coupling and/or far field coupling. In at least one instance, the RFID technology employed herein comprises an RFID chip, a processor, a memory, a transmitter, a tag antenna, a reader antenna, a modulator, a rectifier, and/or a logic circuit, for example.

Detecting the type of staple cartridge assembly to be used with a surgical stapling system can be used to notify and/or alert a user and/or a control program of the type of staple cartridge assembly installed within an end effector, for example. The information may be made aware to a user by way of a display, for example, onboard a surgical instrument handle. The information may be automatically fed to a control program, or control circuit, of the surgical stapling system. In at least one instance, detecting the type of staple cartridge assembly to be used with a surgical stapling system can be used to alter a motor control program to specifically accommodate the type of staple cartridge assembly installed within the end effector. Firing speed, for example, can be altered based on cartridge color, length, and/or staple size.

Such information can be communicated to a surgical hub, for example. In at least one instance, the surgical hub is configured to suggest and/or automatically employ an operational adjustment to a control program of a surgical stapling system for a specific staple cartridge assembly. In at least one instance, a surgical hub is configured to alert a user if the correct staple cartridge assembly has been installed according to known patient and/or procedural data. For example, a surgical hub may already be aware of the specific patient being operated on and, in at least one instance, the surgical hub compares the type of staple cartridge assembly installed within the surgical stapling system against data known about the specific patient. Such a configuration can be utilized to detect if an incorrect staple cartridge assembly has been installed in an end effector, for example. At such a point, the surgical hub and/or a control program of the surgical stapling instrument can lock out the instrument until the correct staple cartridge assembly is installed within the end effector.

In at least one instance, a control program of the surgical stapling system monitors the force required to fire staples and cut tissue during a firing stroke. In such an instance, identifying the type of staple cartridge assembly being used can compare force to an expected feedback force profile, for example, specific to the staple cartridge assembly installed within the end effector. In at least one instance, taller staples may require greater force to be fired, for example. In such an instance, providing this information to a control program can allow the control program to increase the provided firing force during a firing stroke according to what force profile is expected.

In at least one instance, information specific to the staple cartridge assembly installed within the surgical stapling instrument can comprise a batch number and/or manufacturing information such as manufacturing date, for example, specific to the staple cartridge assembly. In at least one instance, information specific to the staple cartridge assembly can comprise writable information comprising, for example, the spent/unspent status of the staple cartridge assembly, for example. In such an instance, a control program is configured to write information onto an RFID tag of a staple retainer, for example, which indicates that the staple cartridge assembly has been spent. In such an instance, should a staple retainer comprising the RFID tag be reinstalled into a staple cartridge assembly making the staple cartridge assembly appear as though it is a new, unused staple cartridge assembly, a subsequent scan of the staple retainer would inform the control circuit and/or user that the staple cartridge assembly has, in fact, been used. Such a configuration can prevent the use of an already used staple cartridge assembly.

Surgical stapling systems utilizing RFID tags and/or readers such as those disclosed herein can reduce and/or eliminate the need for electrical leads passing through shaft assemblies, end effector assemblies, and/or articulation joints, for example to identify the type of staple cartridge assembly installed within an end effector assembly. Such staple cartridge assemblies may also be backwards compatible with a variety of different instruments as long as the instruments comprise RFID readers, for example, and the control circuits required for reading and interpreting the information gathered from the RFID tag.

Figure 6:
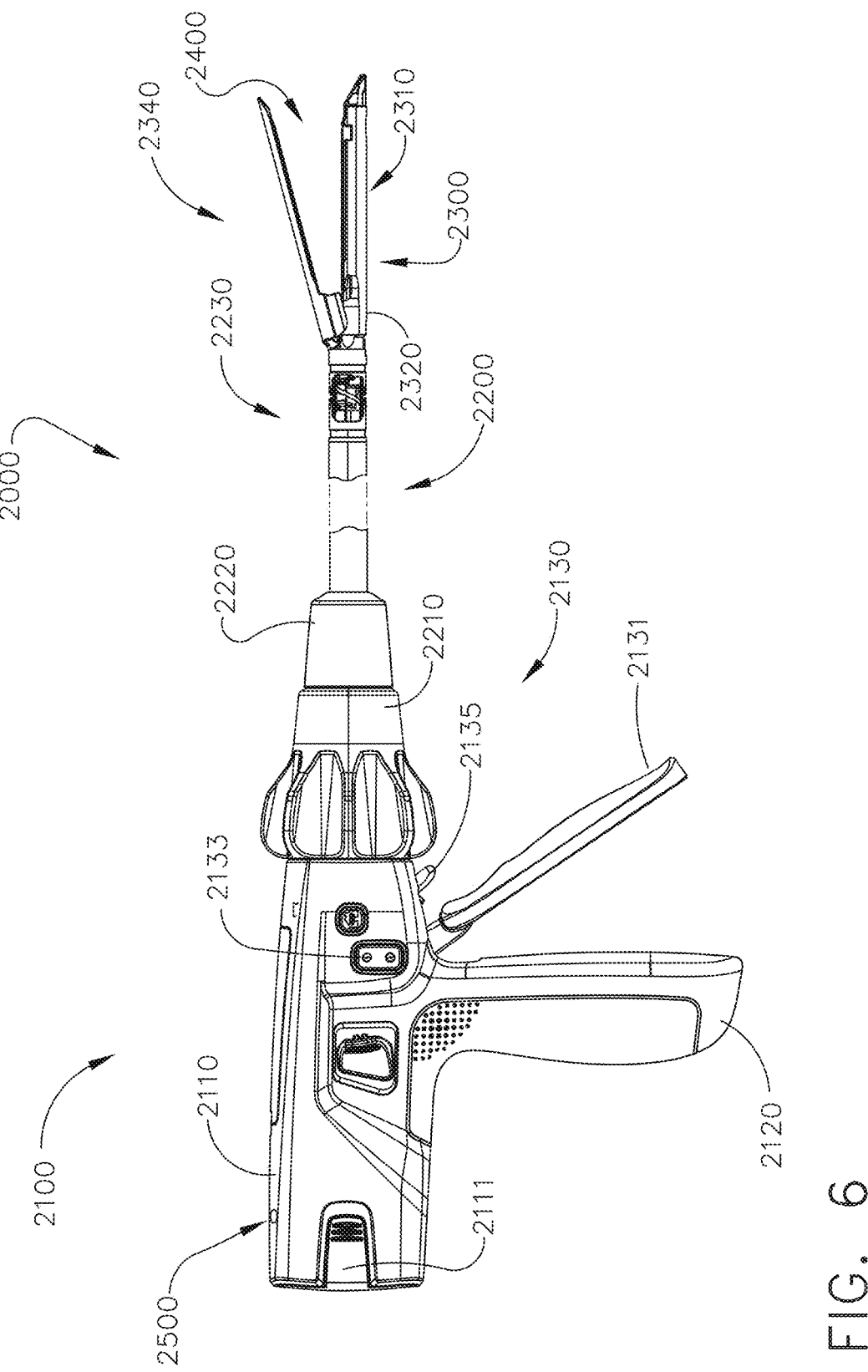
FIG. 6 is an elevational view of a surgical stapling assembly comprising a surgical instrument handle, a shaft assembly, an end effector assembly, and a staple cartridge assembly comprising a staple retainer and a cartridge assembly, wherein the staple retainer is detectable by the surgical instrument handle.
Figure 7:
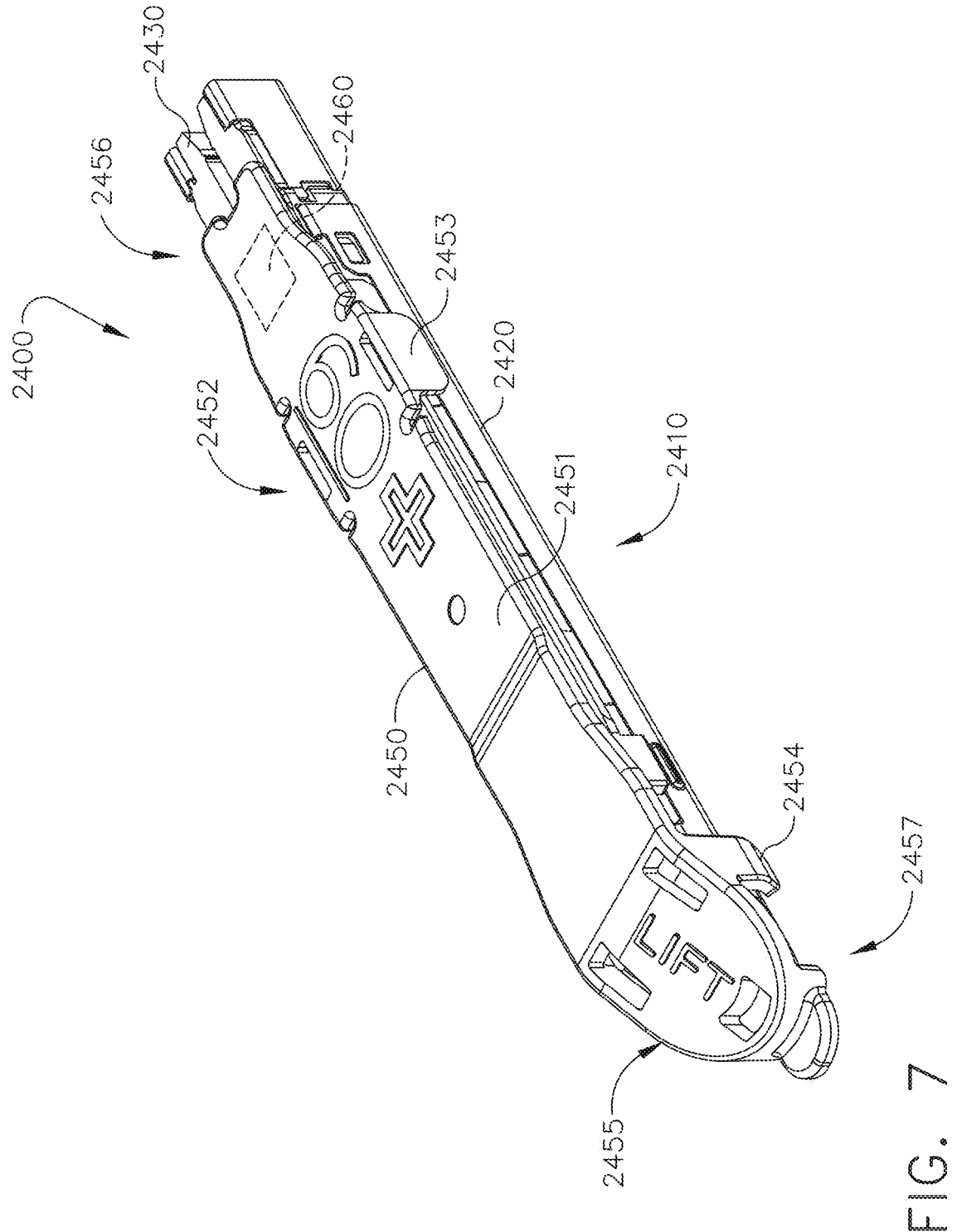
FIG. 7 is a perspective view of the staple cartridge assembly of FIG. 6, wherein the staple retainer comprises an RFID tag embedded therein.
Figure 8:
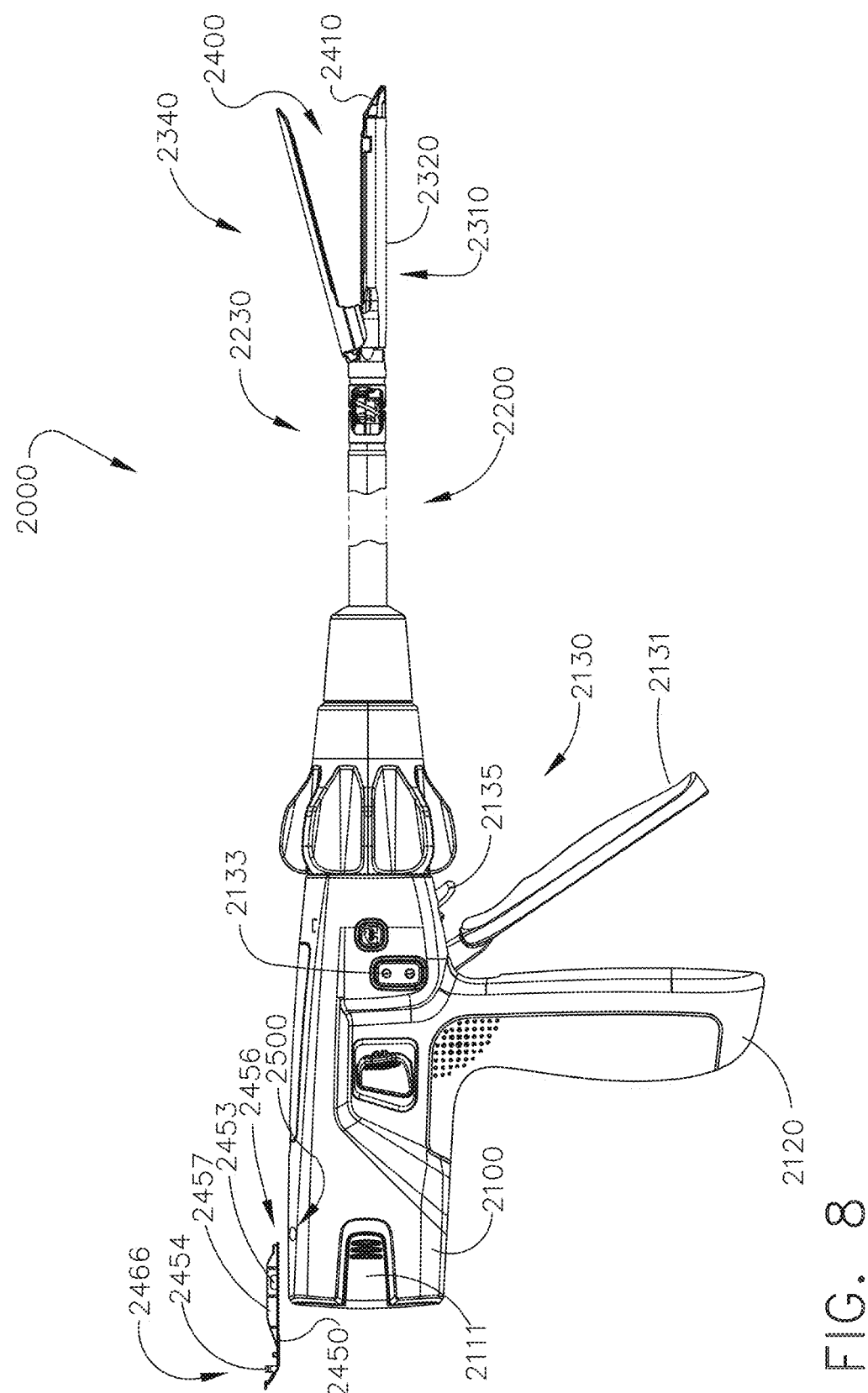
FIG. 8 is an elevational view of the surgical stapling assembly of FIG. 6, wherein the staple retainer is positioned near the surgical instrument handle for detection of the RFID tag.

FIGS. 6-8 depicts a surgical stapling assembly 2000 comprising a surgical instrument handle, or interface, 2100, a shaft assembly 2200 attachable to and detachable from the handle 2100, and an end effector assembly 2300. In at least one instance, the shaft assembly 2100 is attachable to and detachable from a surgical robotic interface, in lieu of or in addition to being attachable to and detachable from the surgical instrument handle 2100. The surgical stapling assembly 200 is configured to receive replaceable staple cartridge assembly reloads. The surgical stapling assembly 2000 comprises a staple cartridge assembly 2400 (FIG. 7) configured to be attached to the end effector assembly 2300. The staple cartridge assembly 2400 comprises a cartridge assembly 2410 and a staple retainer 2450 configured to be detached from the cartridge assembly 2410 after the staple cartridge assembly 2400 is installed within the end effector assembly 2300, discussed in greater detail below.

The handle 2100 comprises a housing 2110 configured to house a plurality of components therein such as, for example, electronics, printed circuit boards, and/or drive train components. The handle 2100 further comprises a battery 2111 configured to be attached to the housing 2110 to power various onboard electronics and/or motors of the handle 2100. The handle 2100 further comprises a pistol grip portion 2120 configured to be held by a user and a plurality of triggers 2130 configured to actuate various functions of the surgical stapling assembly 2000. The triggers 2130 may be mechanical and/or electromechanical. The triggers 2130 comprise a clamping trigger 2131 configured to clamp and unclamp tissue with the end effector assembly 2300 and a firing trigger 2135 configured to cut and staple tissue clamped with the end effector assembly 2300. The triggers 2130 further comprise an articulation rocker switch 2133 configured to articulate the end effector assembly 2300 about an articulation joint 2230 of the shaft assembly 2100. Discussed in greater detail below, the handle 2100 further comprises a wireless reader 2500 configured to identify the staple cartridge assembly 2400 installed within the end effector assembly 2300.

The shaft assembly 2200 is attachable to and detachable from the handle 2100. The shaft assembly 2200 houses drive shaft components, gear trains, electrical leads, sensors, and/or frame components, for example. The shaft assembly 2200 comprises a proximal nozzle attachment interface 2210, a shaft 2220 extending distally from the interface 2210, and the articulation joint 2230. The end effector assembly 2300 is articulatable relative to and attached to the shaft 2220 by way of the articulation joint 2230.

The end effector assembly 2300 is configured to clamp and unclamp tissue, cut tissue, and/or staple tissue. The end effector assembly 2300 comprises a cartridge channel jaw 2310 configured to receive the staple cartridge assembly 2400 and an anvil jaw 2340 configured to form staples ejected from the staple cartridge assembly 2400. The anvil jaw 2340 is pivotable relative to the cartridge channel jaw 2310. In at least one instance, the cartridge channel jaw 2310 is pivotable relative to the anvil jaw 2340. In at least one instance, the cartridge channel jaw 2310 and the anvil jaw 2340 are pivotable relative to one another.

As discussed herein, the staple cartridge assembly 2400 comprises a cartridge assembly 2410 and a staple retainer 2450. The cartridge assembly 2410 comprises a cartridge body 2430 and a pan 2420 configured to prevent drivers and/or staples from falling out of the bottom of the cartridge body 2430. The pan 2420 is also configured to be fitted within the cartridge channel jaw 2310 upon installation of the staple cartridge assembly 2400 in the end effector assembly 2300. In at least one instance, the staple retainer 2450 is attached to the cartridge assembly 2410 during manufacturing. The staple retainer 2450 is configured to protect the cartridge assembly 2410 during shipping and/or packaging and during installation of the staple cartridge assembly 2400 into the end effector assembly 2300, for example. After the staple cartridge assembly 2400 is installed into the end effector assembly 2300, the staple retainer 2450 is removed by a user.

The staple retainer 2450 comprises a body portion 2451 positioned adjacent to a deck of the cartridge body 2430. The body portion 2451 comprises identifying indicia 2452 configured to indicate one or more parameters of the staple cartridge assembly 2400. For example, the indicia 2452 may indicate an operable length of the staple cartridge assembly 2400. The staple retainer 2450 further comprises a proximal end 2456 and a distal end 2455. The staple retainer 2450 further comprises primary arms 2453 configured to hold the staple retainer 2450 to the cartridge assembly 2410 and distal nose arms 2454 also configured to hold the staple retainer 2450 to the cartridge assembly 2410. The arms 2453, 2454 may comprise a snap fit engagement with the cartridge assembly 2410. The staple retainer 2450 further comprises a slot rib 2457 (FIG. 8) configured to fit within a longitudinal slot of the cartridge body 2430. In at least one instance, the slot rib 2457 further holds the staple retainer 2450 to the cartridge body 2430 by way of a snap fit and/or press fit engagement, for example.

The distal end 2455 comprises a nose portion 2457 configured to be lifted by a user to pry the staple retainer 2450 and disengage the arms 2453, 2454 and/or slot rib 2457 from the cartridge assembly 2410 so that the staple retainer 2450 can be removed from the cartridge assembly 2410 prior to firing the cartridge assembly 2410. Discussed in greater detail below, the staple retainer 2450 comprises a wireless identification tag 2460 such as, for example, an RFID tag, configured to be detected by the wireless reader 2500 of the handle 2100.

To clamp tissue between the jaws 2310, 2340, the clamping trigger 2131 is depressed by a user. To unclamp tissue clamped between the jaws 2310, 2340, a user releases the trigger 2131 and, in at least one instance, the trigger 2131 is spring loaded such that the trigger 2131 is biased toward an unclamped, released position (FIG. 6). After tissue has been clamped between the jaws 2310, 2340, a firing member is configured to be actuated by the firing trigger 2135 to cut the tissue and eject staples from the staple cartridge assembly 2400.

The surgical stapling assembly 2000 allows a user to detect the type of staple cartridge assembly 2400 installed within the end effector assembly 2300. Before and/or after the staple cartridge assembly 2400 is installed within the end effector assembly 2300, the RFID tag 2460 is scanned by the wireless reader 2500. In at least one instance, the wireless reader 2500 comprises an RFID reader. In at least one instance, before and/or after the staple cartridge assembly 2400 is installed within the end effector assembly 2300 the RFID tag 2460, the staple retainer 2450 is brought into a detectable proximity range within the RFID reader 2500 of the handle 2100. At such point, the reader 2500 is configured to detect the RFID tag 2460. A control circuit may be configured to take several actions after the RFID tag 2460 is read such as those described herein. For example, a display may indicate that the correct and/or incorrect staple cartridge assembly 2400 for that specific operation has been installed within the end effector assembly 2300. In at least one instance, a control circuit makes a user and/or robotic control program aware of the type of staple cartridge installed within the end effector assembly 2300. In at least one instance, the control circuit is configured to lockout the use of the surgical stapling assembly 2000 upon detection of an incorrect RFID tag. In at least one instance, the RFID tag can indicate that the staple cartridge assembly 2400 has been spent. In such an instance, the control circuit can indicate the spent status to a user, for example.

In at least one instance, the RFID tag 2460 is embedded within the staple retainer 2450. In at least one instance, the RFID rag 2460 is over molded within the body 2451 during manufacturing of the staple retainer 2450. In at least one instance, the RFID tag 2460 is attached to an exterior surface of the staple retainer 2450 after the staple retainer 2450 is manufactured, for example. In at least one instance, an RFID reader is positioned within the end effector assembly 2300 and automatically reads the RFID tag 2460 upon installation of the staple cartridge assembly 2400 into the end effector assembly 2300.

FIG. 8 illustrates a scenario where a user removes the staple retainer 2450 from the cartridge assembly 2410 after installing the staple cartridge assembly 2400 into the end effector assembly 2300 and brings the staple retainer 2450 in the detectable proximity range to the reader 2500 of the handle 2100. In at least one instance, the detectable proximity range is relatively close to the handle 2100. In such an instance, the reader 2500 may not accidentally read other RFID tags of other replaceable staple cartridge assemblies within the operating room, for example. In at least one instance, the reader 2500 is activated on command such that the reader 2500 is not scanning for tags perpetually. In at least one instance, the detectable proximity range comprises a distance which can accommodate scanning the RFID tag 2460 when staple cartridge assembly 2400 is installed within the end effector assembly 2300. In such an instance, a user may be alerted of the type of staple cartridge assembly installed within the end effector assembly prior to removing the staple retainer 2450 from the cartridge assembly 2410.

In at least one instance, the RFID tag comprises authenticity information detectable by the reader. In such an instance, non-authentic staple cartridge assemblies can be detected by a reader of the surgical stapling assembly 2000 and can be alerted to a user and/or can cause a lockout condition of the surgical stapling assembly 2000.

Figure 9:
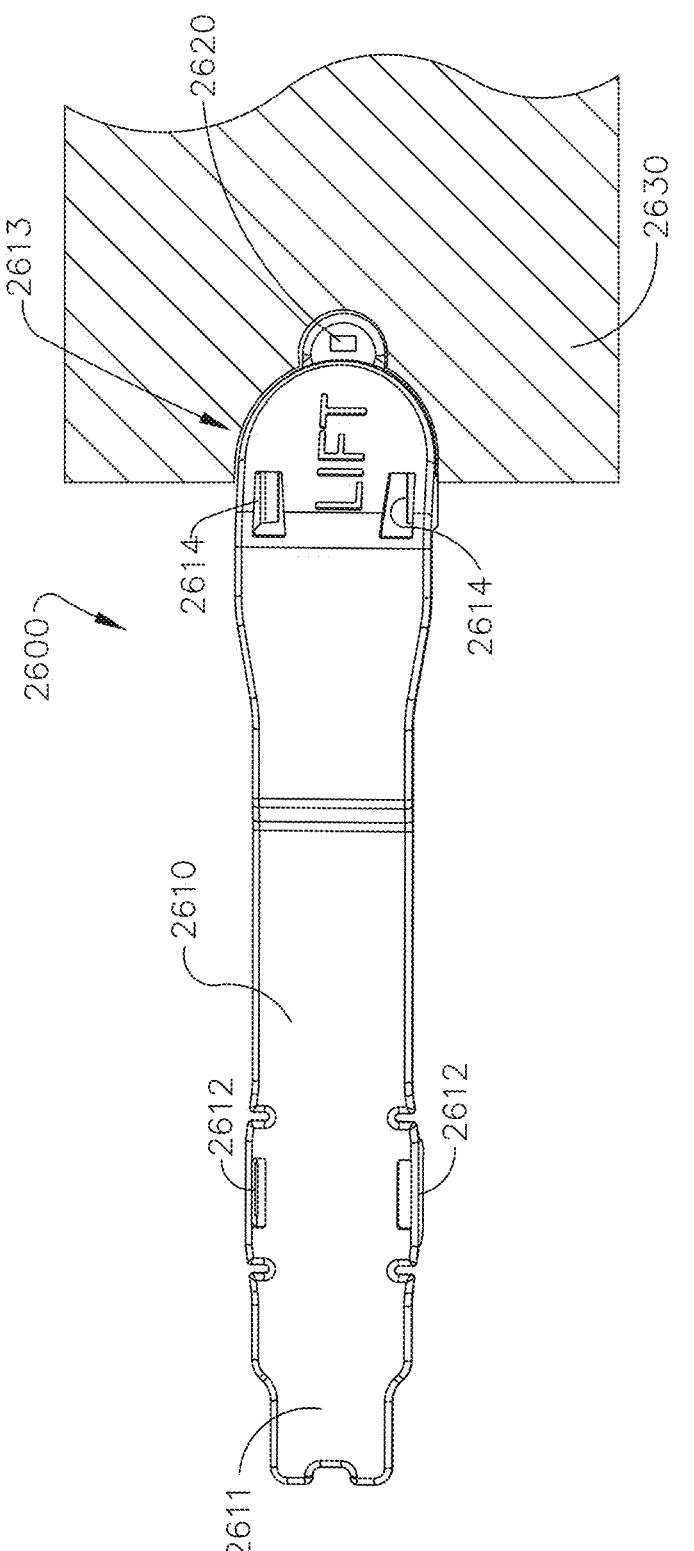
FIG. 9 is a plan view of a surgical instrument identification system comprising a housing and a staple retainer, wherein the staple retainer comprises an RFID tag, wherein the staple retainer is inserted into an aperture defined in the housing for detecting the RFID tag.

FIG. 9 depicts an identification system 2600 comprising a staple retainer 2610 and a housing 2630. The housing 2630 may comprise, for example, a surgical instrument handle housing and/or a robotic tool attachment housing, for example. The staple retainer 2610 comprises a proximal end 2611, attachment arms 2612, and a distal end 2613 comprising attachment arms 2614. The staple retainer 2610 further comprises an RFID tag 2620 positioned at the distal end 2613. In at least one instance, the RFID tag 2620 is embedded within the distal end 2613 of the staple retainer 2610. The staple retainer 2610 is configured to be inserted into a corresponding aperture defined in the housing 2630 such that an RFID reader can detect the RFID tag 2620. Such a configuration can prevent false detection scenarios by requiring a near scan configuration. For example, such a configuration may prevent inadvertent detection of an RFID tag near the housing 2630 which is not the target RFID tag for detection. With such a configuration, a user may be required to fully insert the distal end 2613 of the staple retainer 2610 into the housing 2630 to be able to detect the RFID tag 2620.

Figure 10:
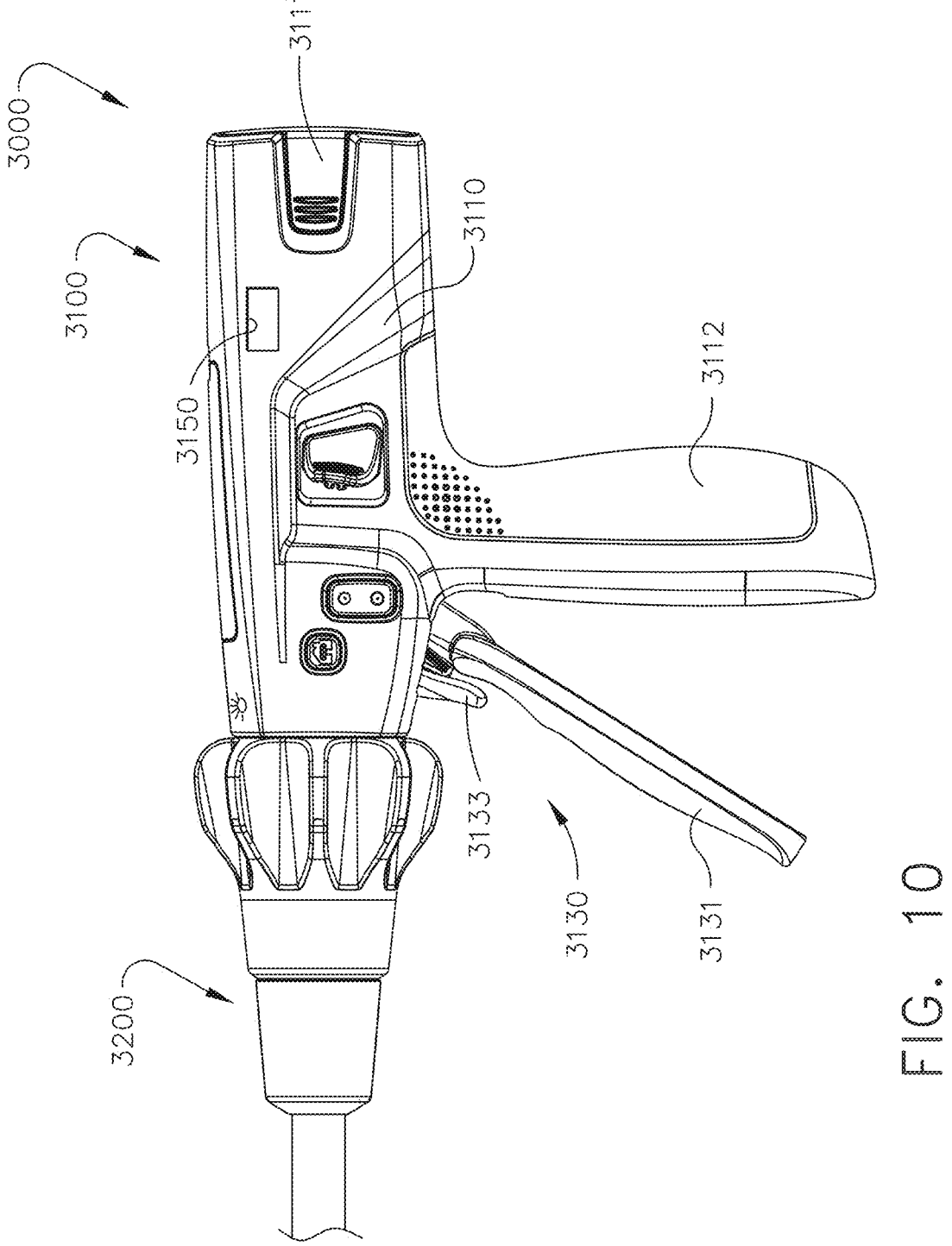
FIG. 10 is an elevational view of a surgical instrument interface comprising an instrument handle, wherein the instrument handle comprises a handle housing, and wherein the handle housing comprises an aperture defined therein for receiving one or more portions of a staple cartridge assembly.
Figure 11:
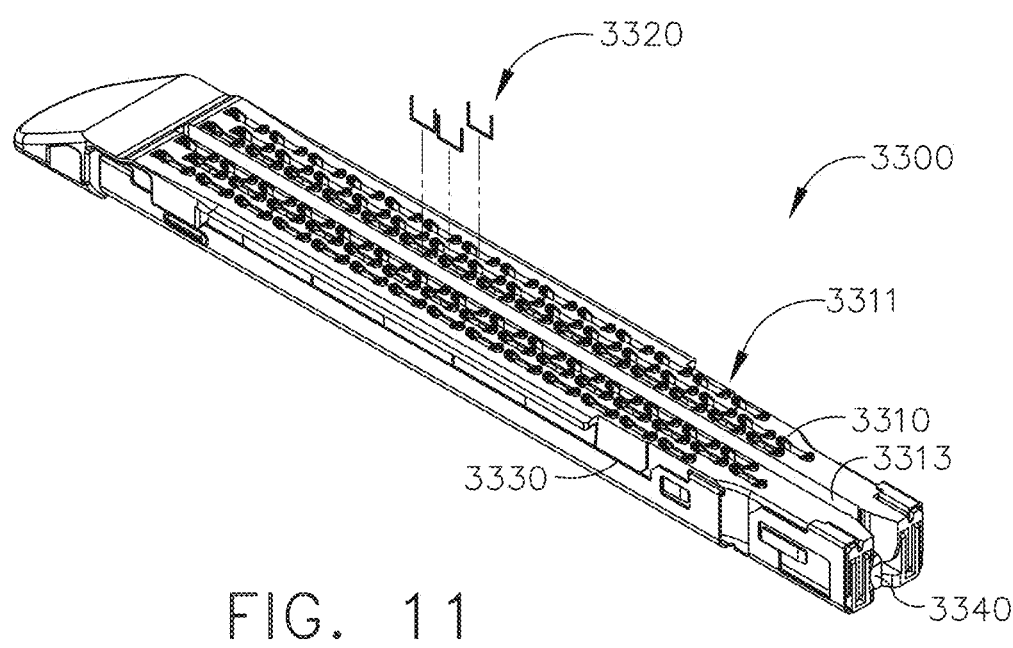
FIG. 11 is a perspective view of a staple cartridge assembly comprising a cartridge body, a cartridge pan, and a sled comprising an RFID tag.
Figure 12:
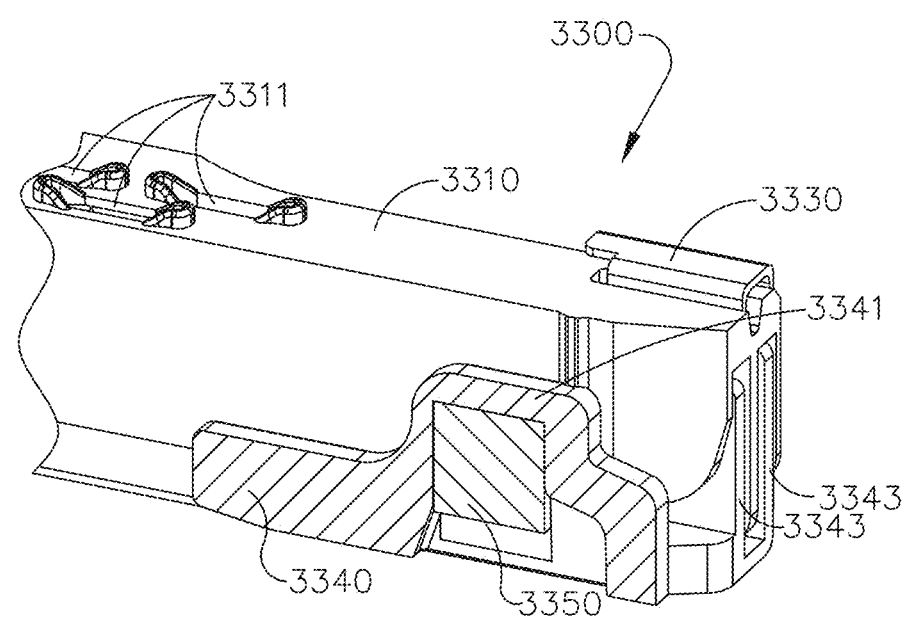
FIG. 12 is a partially cross-sectional view of the staple cartridge assembly of FIG. 11.

FIGS. 10-12 depict a surgical stapling assembly 3000 comprising a handle assembly 3100 and a shaft assembly 3200. The surgical stapling assembly 3000 further comprises an end effector assembly and a staple cartridge assembly 3300 configured to be installed into a cartridge channel jaw of the end effector assembly. The handle assembly 3100 comprises a housing 3110 comprising a pistol grip portion 3112. The handle assembly 3100 further comprises a battery 3111 configured to power various onboard electrical components of the stapling assembly 3000, a plurality of triggers 3130 configured to actuate various functions of the surgical stapling assembly 3000, and a housing aperture, or scanning window, 3150 defined in the housing 3110. The triggers 3130 comprise a clamping trigger 3131 configured to clamp and unclamp tissue and a firing trigger 3133 configured to cut and staple tissue. Discussed in greater detail below, a user is configured to insert the staple cartridge assembly 3330 which is about to be installed into the end effector assembly into the housing aperture 3150. Inserting the staple cartridge assembly 3300 can allow the handle assembly 3100 to scan for RFID tags, for example. In at least one instance, inserting an incorrect staple cartridge assembly into the housing aperture 3150 can lock out the incorrect staple cartridge assembly, discussed in greater detail below.

The staple cartridge assembly 3300 is configured to be installed into and removed from a cartridge channel jaw, for example. The staple cartridge assembly 3300 is replaceable with other staple cartridge assemblies. The staple cartridge assembly 3300 comprises a cartridge body 3310, a plurality of staples 3320, a pan 3330, and a firing member, or sled, 3340 configured to be pushed through the cartridge body 3310 by a firing drive to eject the staples 3320 from the cartridge body 3310. The cartridge body 3310 comprises a plurality of staple cavities 3311 configured to removably store the staples 3320 therein, a longitudinal slot 3313 configured to guide the sled 3340 through the cartridge body 3310 through a firing stroke and configured to receive a cutting member of the firing drive. The pan 3330 is configured to hold the staples 3320 and/or staple drivers within the staple cavities 3311. The sled 3340 is configured to lift the staple drivers and/or staples 3320 out of the staple cavities. The sled 3340 comprises ramps 3343 configured to engage the staple drivers and/or staples 3320 as the sled 3340 is pushed distally through the cartridge body 3310.

The sled 3340 comprises a central portion 3341 configured to be guided within the slot 3313. The sled 3340 further comprises an RFID tag 3350 embedded within the central portion 3341. The RFID tag 3350 is readable by a reader of the handle assembly 3100 upon insertion of the staple cartridge assembly 3330 into the housing aperture 3150. In at least one instance, a proximal end of the staple cartridge assembly 3330, where the sled 3340 resides in a proximal unfired position (FIGS. 11 and 12), is inserted into the housing aperture 3150 to scan the RFID tag 3350. In at least one instance, if the sled 3340 is not in its proximal unfired position, the RFID tag 3350 is unreadable, or undetectable, by a reader of the handle assembly 3100. Such a configuration may prevent the need to write the spent/unspent status of the staple cartridge assembly onto the RFID tag 3350 at least because the physical position of the sled 3340 and the detectability of the RFID rag 3350 determines if the staple cartridge assembly 3300 is spent or unspent. A staple cartridge assembly 3300 can be considered spent if the sled 3340 is not in the position illustrated in FIGS. 11 and 12. The RFID tag 3350 may also comprise identifiable information to determine one or more other parameters of the staple cartridge assembly 3300 such as those disclosed herein.

Figure 13:
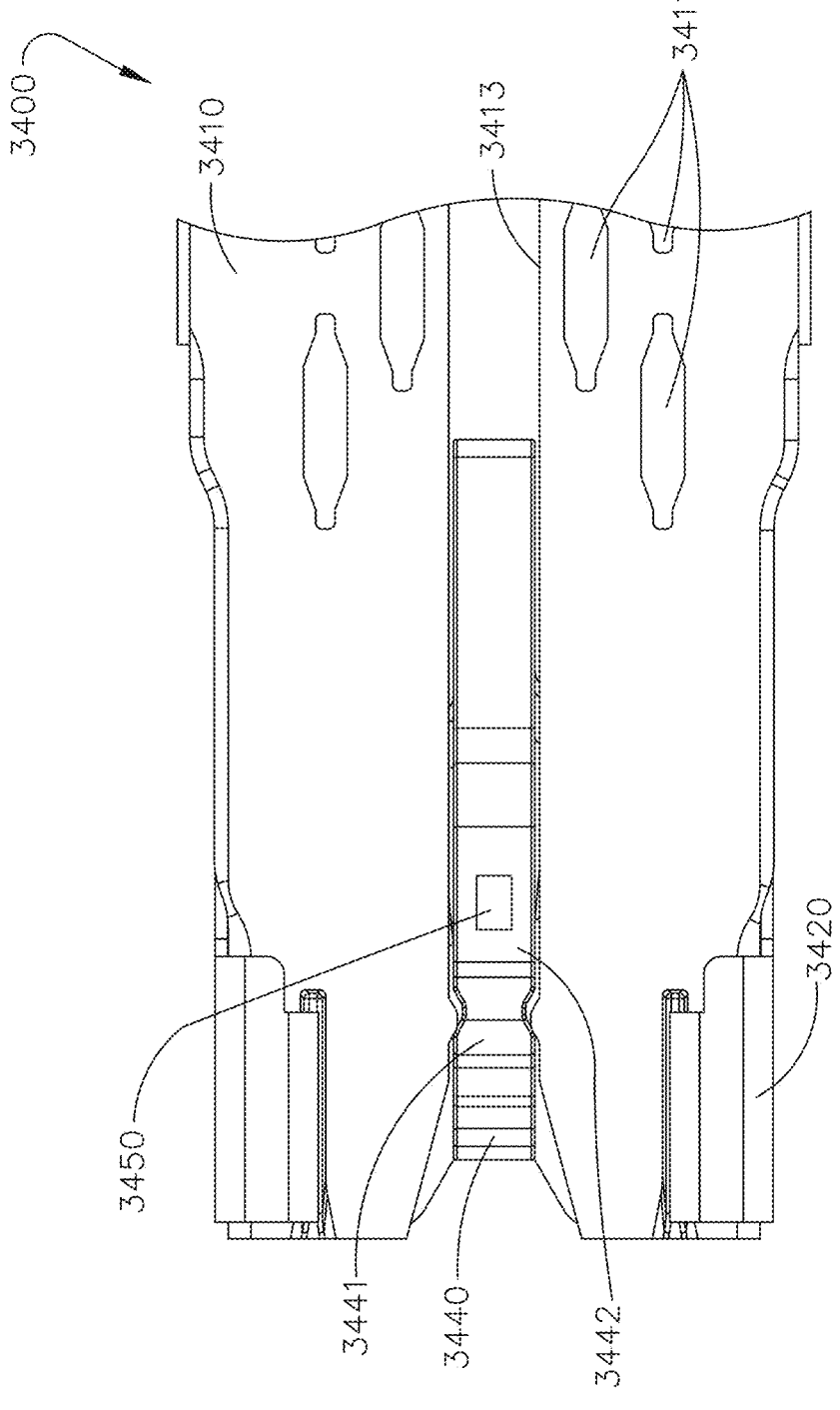
FIG. 13 is a plan view of a staple cartridge assembly comprising a cartridge body, a cartridge pan, and a sled comprising an RFID tag.
Figures 14, 15:
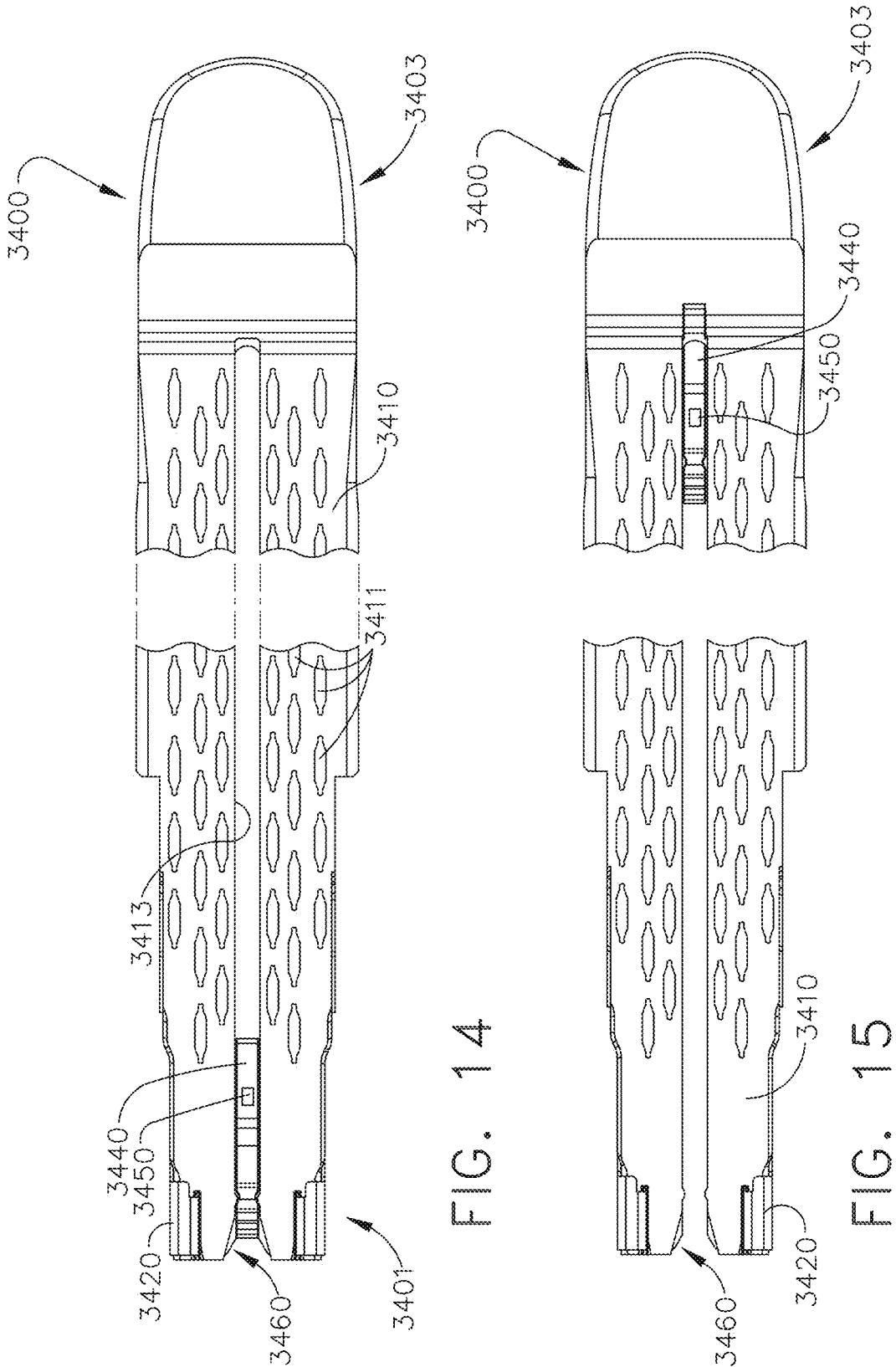
FIG. 14 is a plan view of the staple cartridge assembly of FIG. 13, wherein the sled is illustrated in an unfired position.
FIG. 15 is a plan view of the staple cartridge assembly of FIG. 13, wherein the sled is illustrated in a fired position.

FIGS. 13-15 depict a staple cartridge assembly 3400 detectable by an RFID reader, for example. The staple cartridge assembly 3400 may be used with a handle assembly such as, for example, the handle assembly 3100. The staple cartridge assembly 3400 further comprises means for voiding a non-authentic staple cartridge assembly, discussed in greater detail below. The staple cartridge assembly 3400 comprises a cartridge body 3410, a pan 3420, and a sled 3440. The cartridge body 3410 comprises a plurality of staple cavities 3411 defined in a deck surface of the cartridge body 3410 and a longitudinal slot 3414 defined in and extending between a proximal end 3401 and a distal end 3403 of the staple cartridge assembly 3400 through which the sled 3440 is configured to translate to eject staples from the cartridge body 3410. The sled 3440 is translatable between a proximal unfired position (FIG. 14) and a distal fully fired position (FIG. 15).

The sled 3440 comprises a central portion 3441 defining a top surface 3342. The sled 3440 further comprises an RFID tag 3450. In at least one instance, the RFID tag 3450 is embedded within the top surface 3342. In at least one instance, the RFID tag 3450 is positioned on the top surface 3342. The RFID tag 3450 is detectable by an RFID reader of a handle assembly, for example. The staple cartridge assembly 3400 further comprises an authentication key 3460. In at least one instance, the authentication key 3460 comprises the proximal profile of the staple cartridge assembly 3400 which comprises the notched, or angled, profile of the cartridge body 3410 at the proximal end 3401 and the notched, or angled, profile of a proximal end of the sled 3440. The authentication key 3460 is configured to correspond to a corresponding profile of the housing aperture 3150 such that, if the profiles of the authentication key 3460 and the housing aperture 3150 do not match, the RFID tag is unreadable and/or undetectable. In at least one instance, if the profiles do not match, a feature within the housing aperture 3150 is configured to push the sled of the non-authentic staple cartridge assembly distally into a spent, or partially spent, position. Such a configuration may void non-authentic staple cartridge assemblies, for example, preventing their use with an authentic surgical stapling assembly.

In at least one instance, the authentication key 3460 comprises a "V" notch profile and is complemented by both the proximal end 3401 of the cartridge body 3410 in addition to the proximal end of the sled 3440. In at least one instance, the "V" notch profile is matched within the housing aperture 3150 within which the staple cartridge assembly 3400 is designed to be inserted.

In at least one instance, RFID tags and/or chips disclosed herein comprise integrated antennas which can provide a predetermined detectability range. The range may comprise, for example, 10 mm and/or 15 mm, for example. In at least one instance, the detectability range is less than 10 mm, more than 10 mm but less than 15 mm, and/or more than 15 mm.

In at least one instance, a light 3155 of the handle assembly 3100 illuminates upon detection of an RFID tag. In at least one instance, the light 3155 is configured to flash and/or change colors to specifically convey information corresponding to the detected RFID tag. For example, the light may flash red if a non-authentic staple cartridge assembly has been inserted into the aperture window and/or if a non-authentic RFID tag has been detected. In at least one instance, the light is configured to illuminate solid green if an unspent, authentic staple cartridge assembly and/or RFID tag is detected.

In at least one instance, the light 3155 may blink red, for example, so as to provide a warning signal to a user. The warning signal may indicate an issue with a firing sequence of a surgical stapling system and/or staple cartridge assembly, for example. The warning signal may indicate a jam within one or more drivetrain components of a surgical stapling system.

In at least one instance, only one of the ends 3401, 3403 is sized so as to fit within the housing aperture 3150. Such a configuration may prevent the insertion of an incorrect end of the staple cartridge assembly 3400 into the housing aperture 3150. In at least one instance, a staple cartridge assembly including a staple retainer is configured to be inserted into the housing aperture 3150 while the staple retainer is attached to the staple cartridge assembly.

Figure 16:
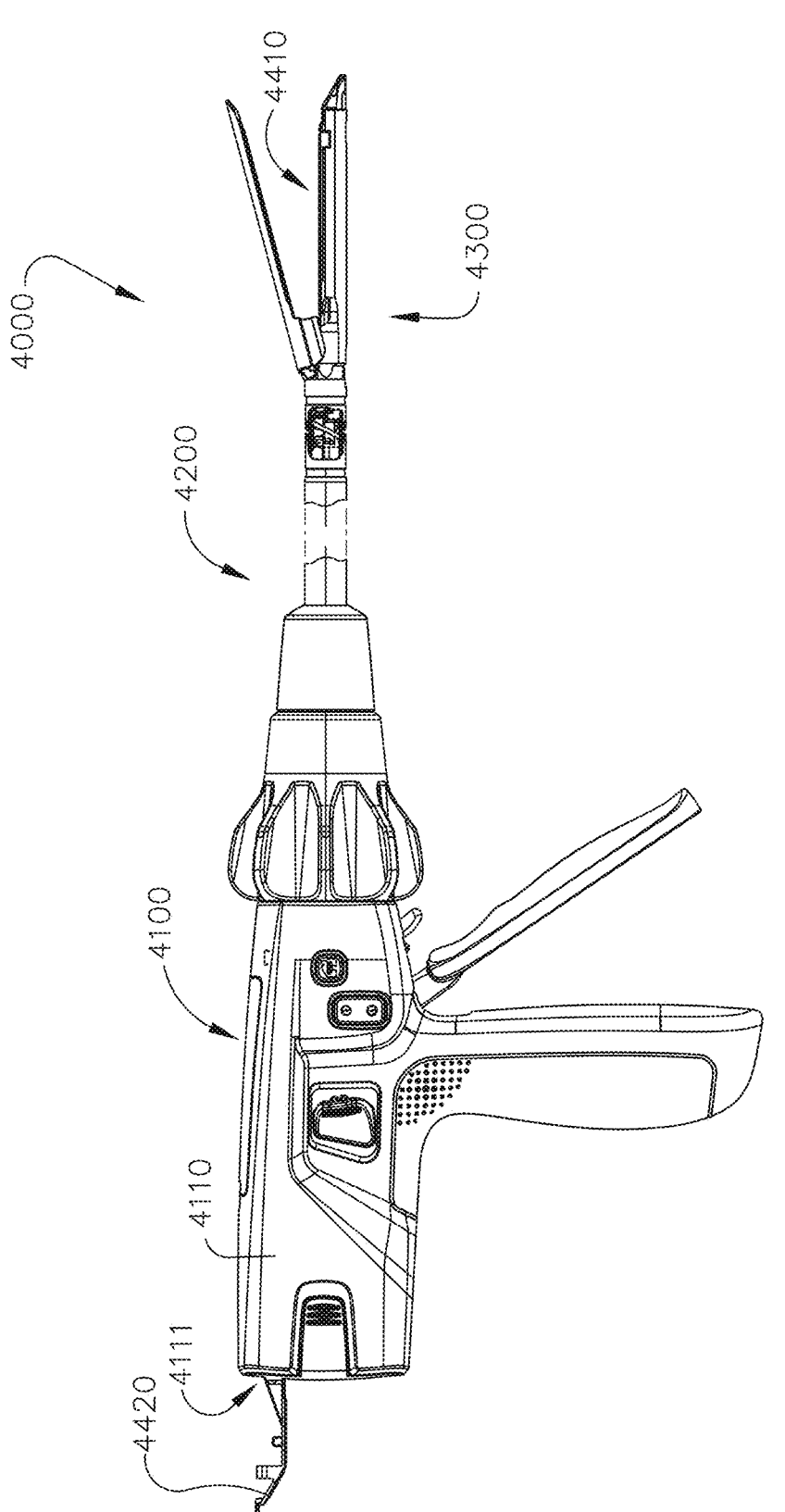
FIG. 16 is an elevational view of a surgical stapling assembly comprising an instrument handle, a shaft assembly, an end effector assembly, and a staple cartridge assembly comprising a staple retainer and a cartridge assembly.
Figure 17:
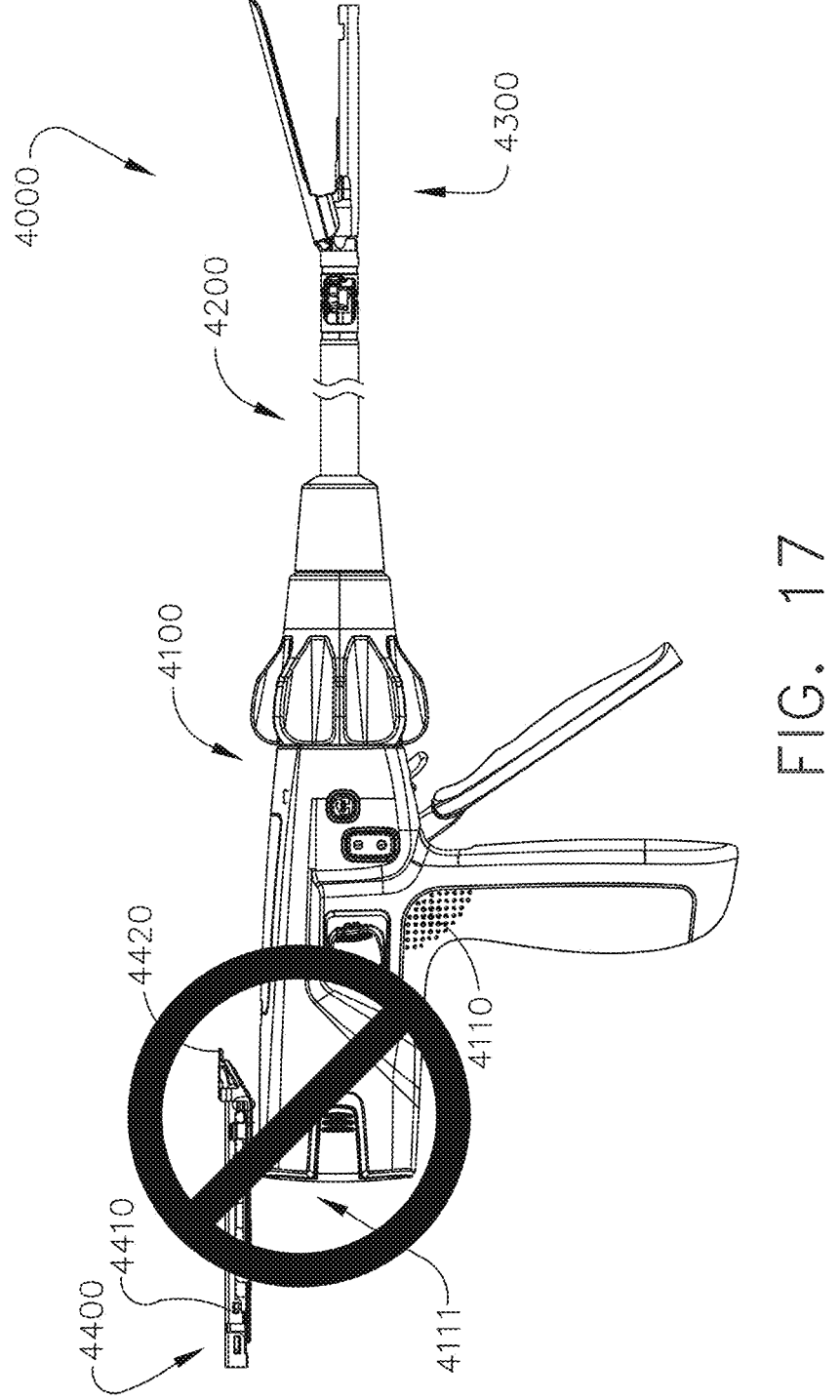
FIG. 17 is an elevational view of the surgical stapling assembly of FIG. 16, wherein the staple cartridge assembly is illustrated in a non-readable configuration.

In at least one instance, a housing aperture of a handle assembly configured to receive one or more portions of a staple cartridge assembly is sized so as to only receive a specific portion of the staple cartridge assembly. FIGS. 16 and 17 depict a surgical stapling assembly 4000 comprising a handle assembly 4100, a shaft assembly 4200, and an end effector assembly 4300. The surgical stapling assembly 4000 further comprises a staple cartridge assembly 4400 comprising a cartridge assembly 4410 and a staple retainer 4420 removable from the cartridge assembly 4410. The handle assembly 4100 comprises a housing 4110 comprising a scanning aperture 4111 defined therein configured to receive only the staple retainer 4420. The staple retainer 4420 comprises an RFID tag, for example. As can be seen in FIG. 17, a user may not be able to scan the RFID tag of the staple retainer 4420 while the staple retainer 4420 is still attached to the cartridge assembly 4410. Such a configuration may prevent a staple cartridge assembly from being scanned while the stapler retainer and the cartridge assembly are attached to each other. Such a configuration may help prevent scanning an RFID tag of one staple cartridge assembly, misplacing the just-scanned staple cartridge assembly prior to installation, picking up a different staple cartridge assembly and removing the staple retainer to install the different staple cartridge assembly. A user may follow a routine of installing the cartridge assembly 4410 into the end effector assembly 4300 and then scanning for an RFID tag by inserting the staple retainer of the just-installed cartridge assembly 4410 into the scanning aperture 4111. In at least one instance, the surgical stapling assembly 4000 is locked out until an RFID tag of the installed reload, or staple cartridge assembly, is detected.

Figure 18:
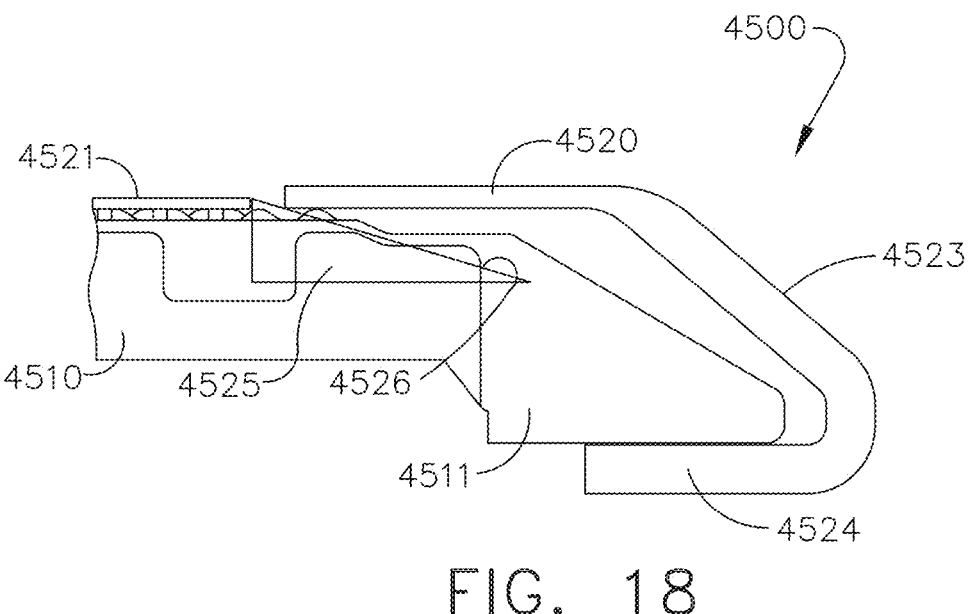
FIG. 18 is a partial elevational view of a staple cartridge assembly comprising a staple retainer and a cartridge assembly, wherein the staple retainer comprises a locking feature configured to prevent removal of the staple retainer prior to installation of the staple cartridge assembly into a cartridge channel of a surgical instrument, wherein the locking feature is illustrated in a locked configuration.
Figure 19:
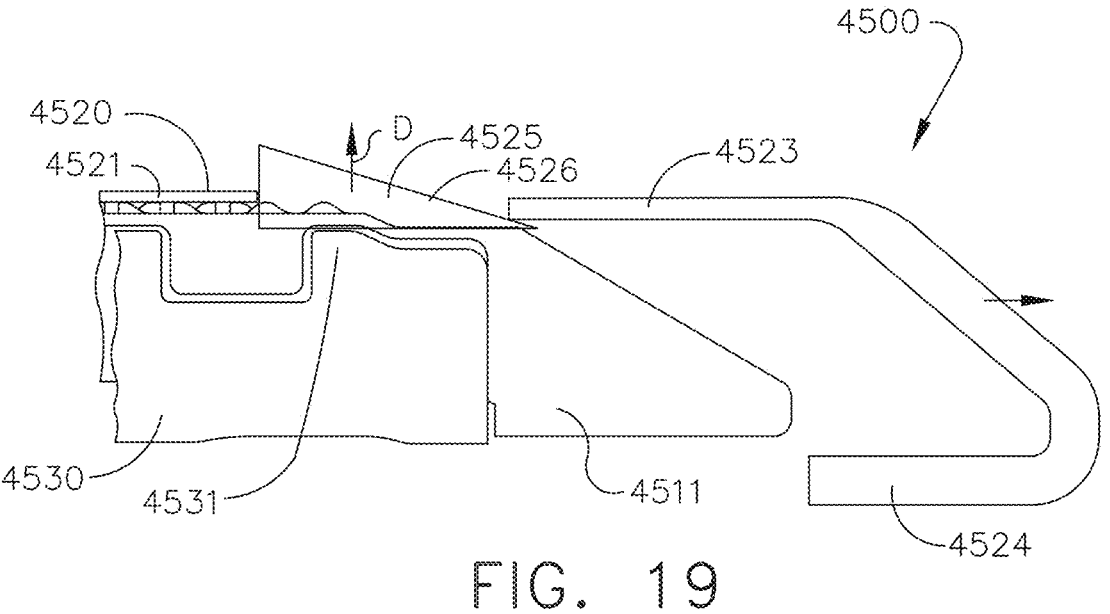
FIG. 19 is a partial elevational view of the staple cartridge assembly of FIG. 18 installed in a cartridge channel, wherein the locking feature is illustrated in an unlocked configuration.

FIGS. 18 and 19 depict a staple cartridge assembly 4500 configured to be installed into a cartridge channel jaw 4530. The staple cartridge assembly 4500 comprises a cartridge assembly 4510 comprising a distal nose 4511. The staple cartridge assembly 4500 further comprises a staple retainer 4520 configured to be attached to and detached from the cartridge assembly 4510. The staple retainer 4520 comprises a primary body portion 4521 configured to cover a top portion of the cartridge assembly 4510 such as, for example, the staple cavities, longitudinal slot, and cartridge deck surface. The staple retainer 4520 further comprises a distal hook nose 4523 fitted around the distal nose 4511 of the cartridge assembly 4510. The staple retainer 4520 is prevented from being removed prior to installation of the staple cartridge assembly 4500 into the cartridge channel jaw 4530.

The staple retainer 4520 further comprises a camming feature 4526. In at least one instance, the camming feature 4526 fits within the longitudinal slot of the cartridge assembly 4510. The camming feature 4526 is configured to be pushed vertically away from the cartridge assembly 4510 upon installation of the staple cartridge assembly 4500 into the cartridge channel jaw 4530 by one or more sidewalls 4531 of the cartridge channel jaw 4530. The camming feature 4526 is configured to detach and/or at least partially detach the distal hook nose 4523 of the staple retainer 4520 from the primary body portion 4521 as the camming feature 4526 is pushed vertically away from the cartridge assembly 4510 to allow the staple retainer 4520 to be removed from the cartridge assembly 4510 after the staple cartridge assembly 4500 is fully installed within the cartridge channel jaw 4530. In at least one instance, the staple retainer 4520 is molded with perforations designed to tear during installation of the staple cartridge assembly 4500 into the cartridge channel jaw 4530 allowing the distal hook nose 4523 to disengage from the distal nose 4511 of the cartridge assembly 4510. In at least one instance, the distal hook nose 4523 is completely torn away from the body portion 4521. In at least one instance, the camming feature 4526 comprises a spring feature biased downwardly into the position illustrated in FIG. 18 and the camming feature 4526 reverts back to this position after the staple retainer 4520 is slid away, or detached from, the distal nose 4511 and the cartridge assembly 4510. Nonetheless, once the staple cartridge assembly 4500 is fully installed, the staple retainer 4520 can then be removed from the cartridge assembly 4510.

Figures 20, 21:
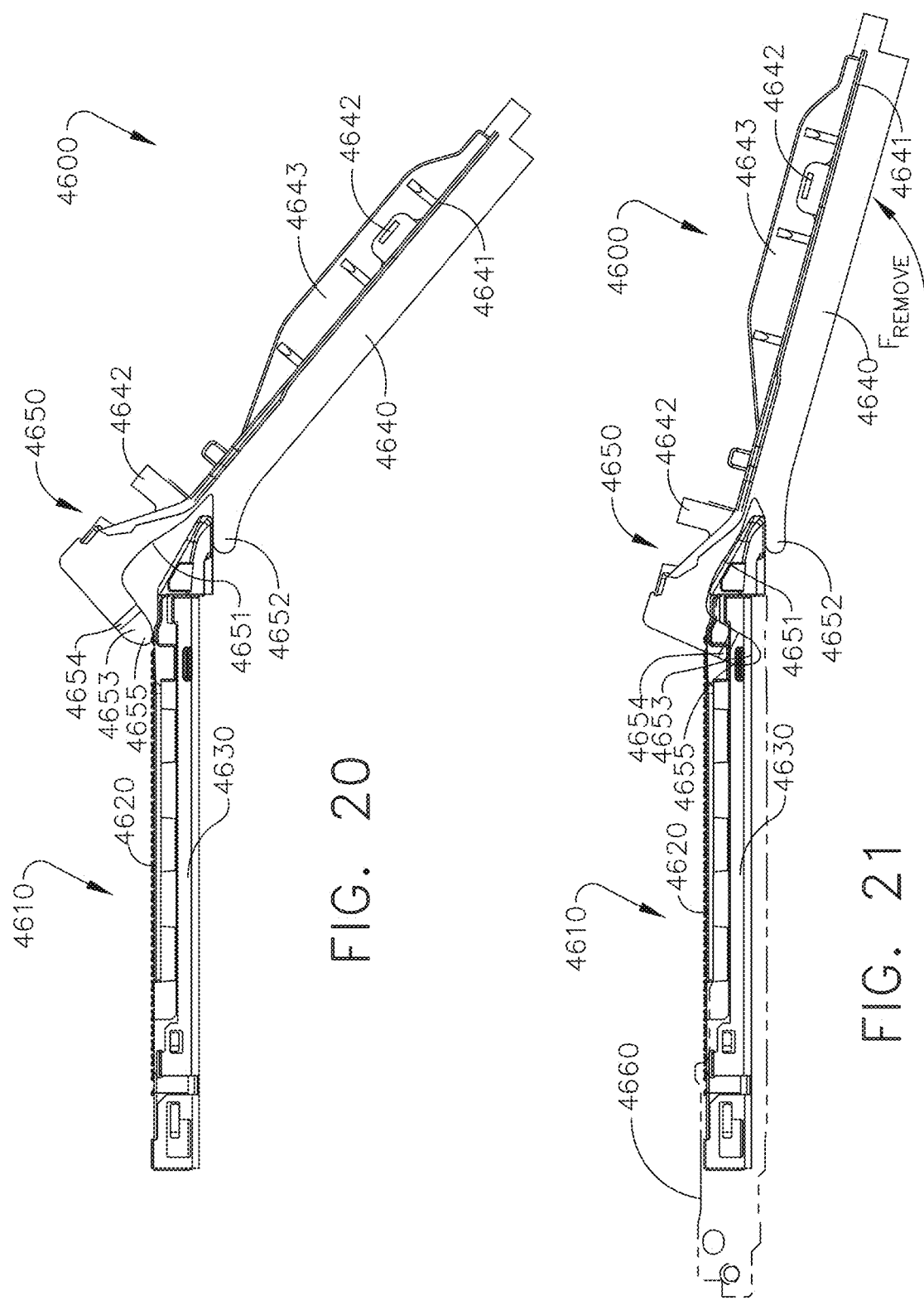
FIG. 20 is an elevational view of a staple cartridge assembly comprising a cartridge assembly and a staple retainer, wherein the staple retainer comprises a pry feature and a locking feature configured to lock the staple retainer to the cartridge assembly upon using the pry feature to remove the cartridge assembly from a cartridge channel.
FIG. 21 is an elevational view of the staple cartridge assembly of FIG. 20 installed in a cartridge channel, wherein the locking feature is illustrated in a locked configuration.
Figure 22:
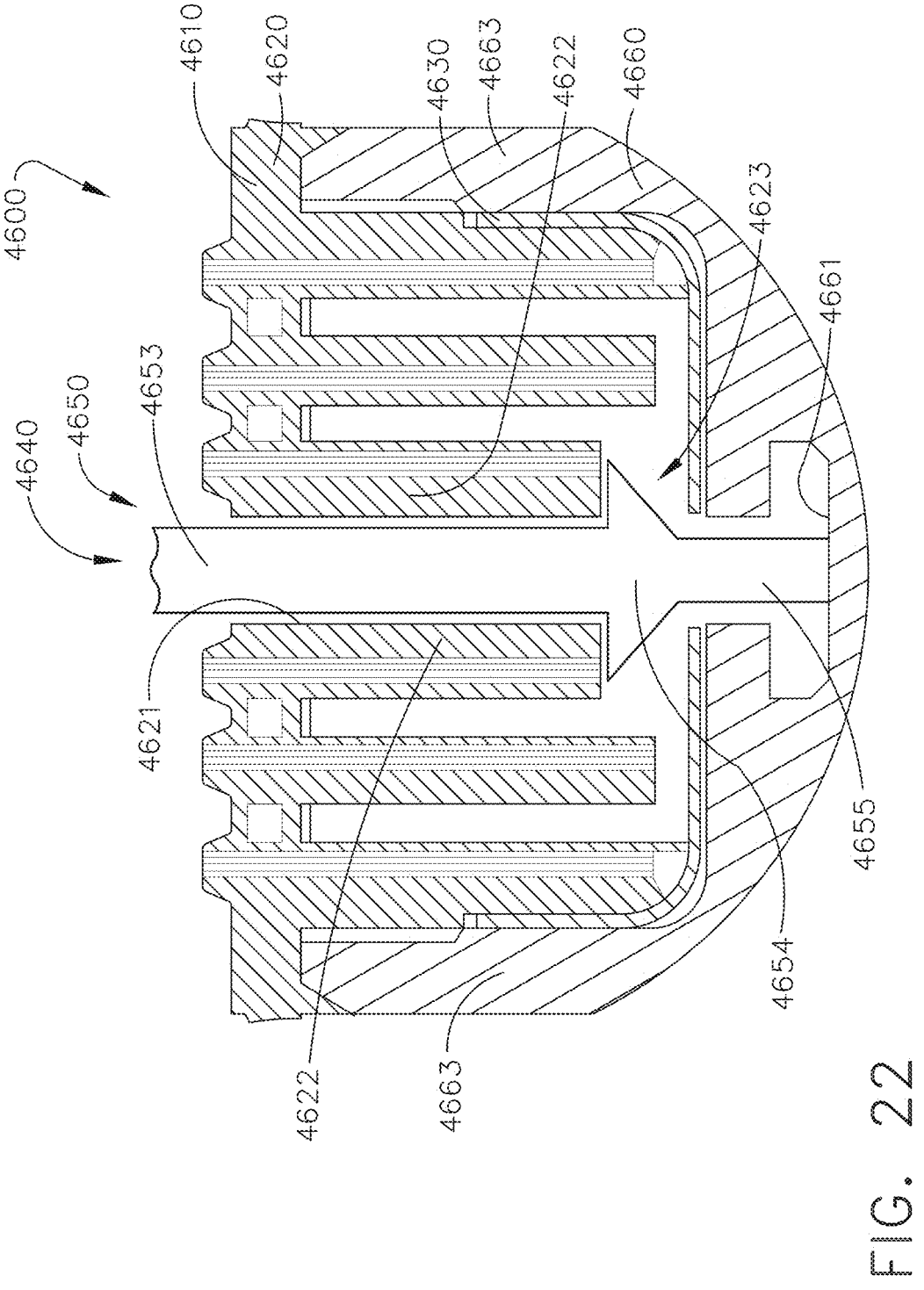
FIG. 22 is a cross-sectional view of the staple cartridge assembly of FIG. 20 installed within the cartridge channel, wherein the locking feature is illustrated in the locked configuration.
Figure 23:
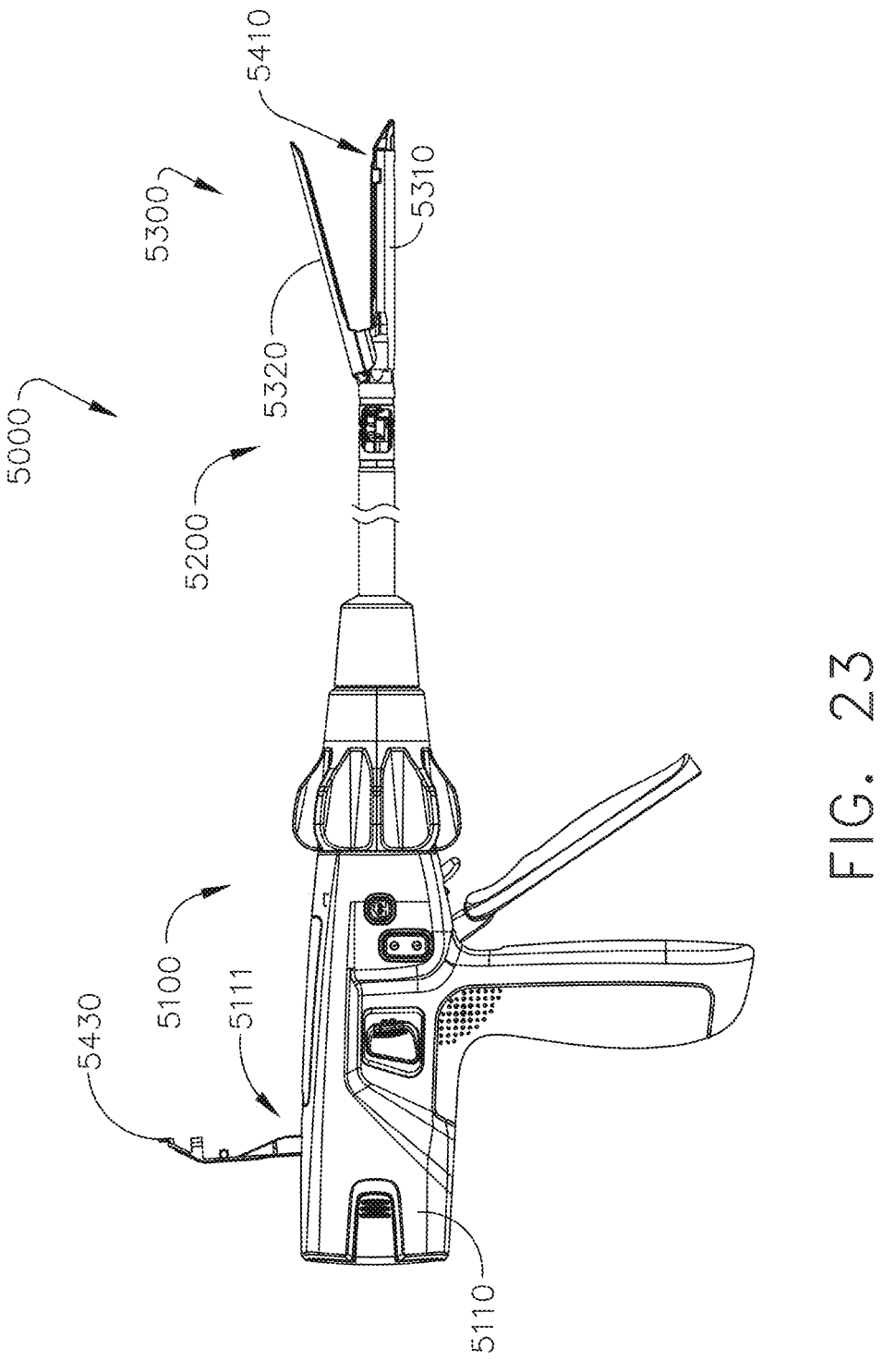
FIG. 23 is an elevational view of a surgical stapling assembly comprising an instrument interface and a staple cartridge assembly, wherein the staple cartridge assembly comprises a staple retainer comprising a pattern of features configured to be detected by the instrument interface and indicative of information specific to the staple cartridge assembly.

FIGS. 20-22 depict a staple cartridge assembly 4600 for use with a surgical stapling assembly such as those disclosed herein, for example. The staple cartridge assembly 4600 comprises a cartridge assembly 4610 and a staple retainer 4640 configured to be removed from the cartridge assembly 4610 prior to use of the cartridge assembly 4610 installed within a stapling assembly. The cartridge assembly 4610 comprises a cartridge body 4620 and a pan 4630. The cartridge body 4620 further comprises a longitudinal slot 4621 configured to receive a firing member therethrough defined by inner cartridge body walls 4622. The cartridge body 4620 further comprises a lower cavity channel 4623 configured to receive at least a portion of a sled, for example, therethrough.

The staple cartridge assembly 4600 is configured to be installed in a cartridge channel 4660 comprising channel walls 4663 and a longitudinal camming slot 4661 configured to receive a camming foot of a firing member therethrough. The staple retainer 4640 is configured to be removed from the cartridge assembly 4610 prior to firing the cartridge assembly 4610. Once the cartridge assembly 4610 has been fired and/or is ready to be removed from the cartridge channel 4660, the staple retainer 4640 can be used to pry the cartridge assembly 4610 from the cartridge channel 4660. The staple retainer 4640 comprises a body portion 4641, a longitudinal rib 4643 extending from the body portion 4641 and configured to be received within the slot 4621, holding arms 4642 configured to hold the staple retainer 4640 to the cartridge assembly 4610, and a proximal portion 4650 configured to be used as a pry tool for removing the cartridge assembly 4610 from the cartridge channel 4660 and a locking feature to prevent the cartridge assembly 4610 from being used again.

The proximal portion 4650 of the staple retainer 4640 comprises a pry cavity 4651 defined by a leverage hook 4652 and a pry tool portion 4653. The pry cavity 4651 is configured to be positioned around the nose of the cartridge assembly 4610 such that the hook 4652 engages a bottom surface of the nose of the cartridge assembly 4610 and the pry tool portion 4653 can be positioned within the longitudinal slot 4621. The proximal portion 4650 is lifted to pivot the retainer 4640 relative to the cartridge assembly 4610 so as to insert the pry tool portion fully into the slot 4621 and toward a bottom surface 4661 of the cartridge channel 4660. Once the position in FIGS. 21 and 22 is attained, leverage is gained on the cartridge assembly 4610 against the cartridge channel 4660 to pry the cartridge assembly 4610 out of the cartridge channel 4610.

The pry tool portion 4653 further comprises locking ledges 4653 extending laterally from the pry tool portion 4653. The locking ledges 4653 are configured to bias the inner walls 4621 laterally outwardly so as to insert the locking ledges 4653 into the lower cavity channel 4623. Once the ledges 4653 clear the bottom of the walls 4622, the walls spring back inwardly into their home position (FIG. 22). At this point, the staple retainer 4640 is locked to the cartridge assembly 4610 as the ledges 4654 prevent the staple retainer 4640 from being detached from the cartridge assembly 4610. Such a configuration can prevent inadvertent reuse of a cartridge assembly 4610 by permanently, in at least one instance, locking the staple retainer 4640 to the cartridge assembly 4610 in a non-functional configuration (FIG. 21). A user would not install the staple cartridge assembly 4600 in the non-functional configuration illustrated in FIG. 21. In at least one instance, the ledges 2653 are flexible and walls 4621 are more rigid than the ledges 2653. In such an instance, the ledges 2653 deform inwardly as the ledges 2653 move vertically through the slot 4621 and spring back to their undeformed position (FIG. 22) upon reaching the lower cavity channel 4623.

In at least one instance, the staple retainer 4640 is required to remove the cartridge assembly 4610 from the cartridge channel 4660. In such instance, locking the staple retainer 4640 to the cartridge channel 4660 also prevents an attempt to reuse the staple retainer 4640 with a non-authentic staple cartridge assembly, for example. The pry tool may also reduce the force required to remove the cartridge assembly 4610 from the cartridge channel 4660.

FIGS. 23-26 depict a surgical stapling assembly 5000. The surgical stapling assembly 5000 comprises a handle assembly 5100, a shaft assembly 5200, and an end effector assembly 5300 configured to receive a replaceable staple cartridge assembly therein. The handle assembly 5100 comprises a handle housing 5110 comprising an aperture 5111 defined therein. Discussed in greater detail below, a user is configured to insert a staple retainer 5430 of the staple cartridge assembly into the aperture 5111 in order to detect the type of staple cartridge assembly that is installed in the end effector assembly 5300. The end effector assembly 5300 comprises an anvil jaw 5320 and a cartridge channel jaw 5310 configured to receive the staple cartridge assembly therein.

Figure 24:
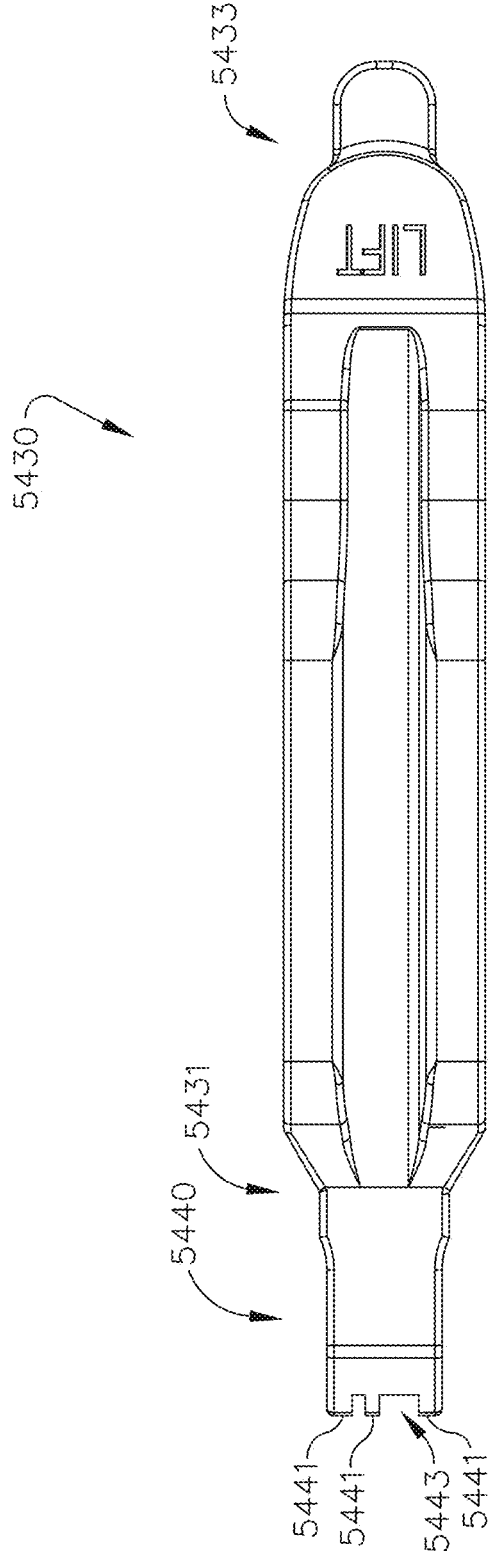
FIG. 24 is a plan view of the staple retainer of FIG. 23.
Figures 25, 26:
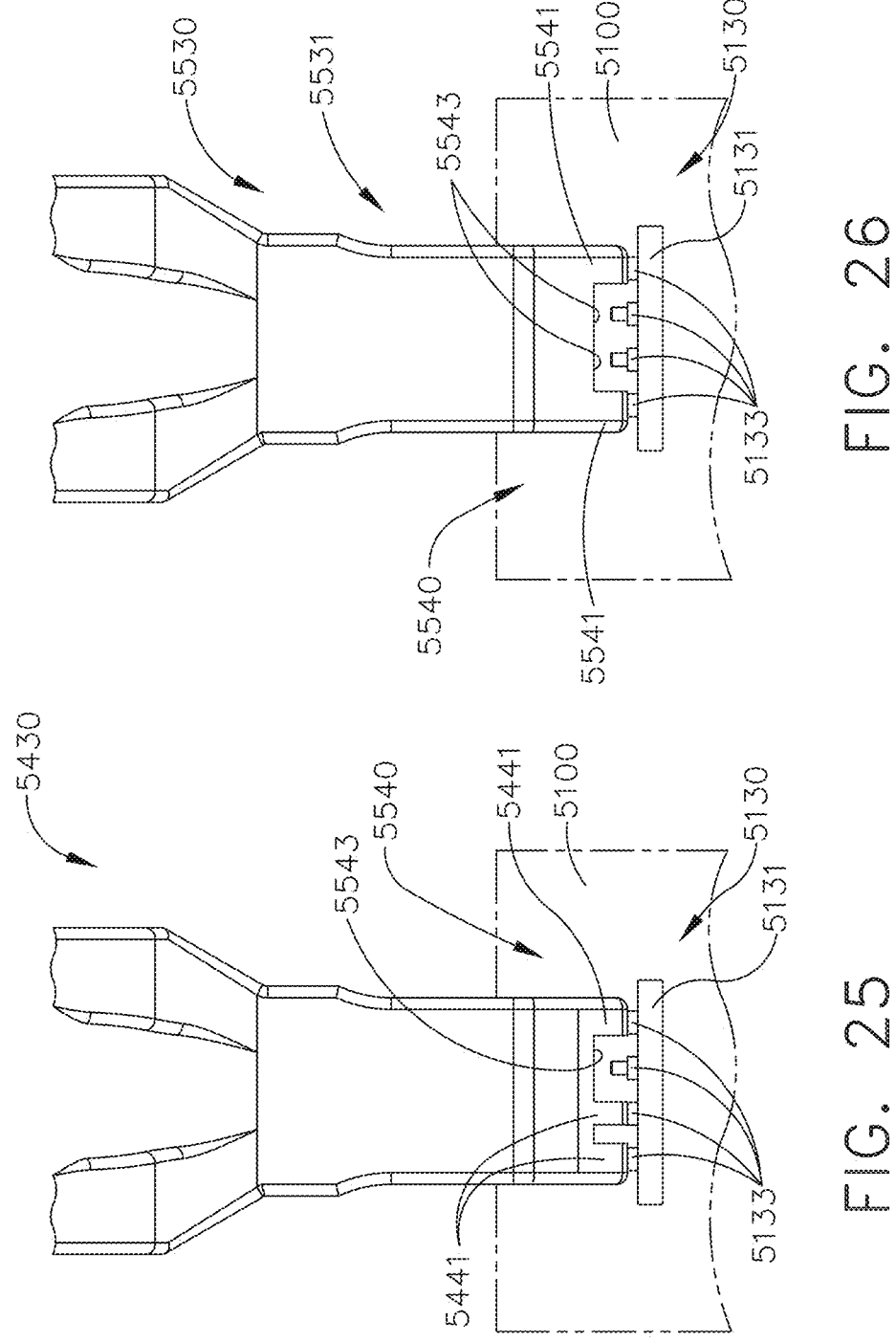
FIG. 25 is a partial elevational view of the staple retainer and the instrument interface of FIG. 23.
FIG. 26 is a partial elevational view of a staple retainer different than the staple retainer of FIG. 23 and the instrument interface of FIG. 23.

The staple cartridge assembly comprises a cartridge assembly 5410 and a cartridge retainer 5430. The cartridge retainer 5430 is configured to be removed from the cartridge assembly 5410 after the staple cartridge assembly is installed within the cartridge channel jaw 5310. Referring to FIG. 24, the staple retainer 5430 comprises a proximal end and a distal end 5433. The proximal end 5431 of the staple retainer 5430 further comprises a unique profile 5440 of features 5441, 5443. The features 5441, 5443 comprise proximally-extending tabs 5441 and one or more gaps 5443 between the tabs 5441. The features 5441, 5443 are unique to each type of staple cartridge assembly. For example, the profile of features 5441, 5443 are specific so as to be able to identify the type of staple cartridge assembly to which the staple retainer 5430 is attached.

The proximal end 5431 is configured to be inserted into the aperture 5111 of the housing 5100 to engage a detection system 5130. The detection system 5130 comprises a plurality of sensors 5133 such as switches, for example, which are coupled to a printed circuit board 5131 and a control circuit. The specific combination of switches which are detected to be switched on, for example, can indicate one or more identifiable parameters of the staple cartridge assembly. A different staple retainer 5530 having different identifiable parameters comprises a different unique profile 5540 of features 5541, 5543 configured to press a different combination of the switches 5133, for example. The features 5541, 5543 comprise proximally-extending tabs 5541 and one or more gaps 5543 between the tabs 5541. The different unique profile 5540 is configured to indicate different identifiable parameters of a different staple cartridge assembly to which the staple retainer 5530 is attached to a control circuit of the surgical stapling system 5500.

Various aspects of the subject matter described herein are set out in the following numbered examples:

Example 1—A surgical stapling system comprising an instrument interface comprising a control circuit and an RFID reader. The surgical stapling system further comprises a shaft assembly attachable to and detachable from the instrument interface. The shaft assembly comprises a shaft and an end effector. The end effector comprises a first jaw, a second jaw movable relative to the first jaw, an anvil, and a cartridge channel. The surgical stapling system further comprises a replaceable staple cartridge assembly removably positioned within the cartridge channel. The replaceable staple cartridge assembly comprises a cartridge body, a longitudinal slot, a plurality of staple cavities defined in the cartridge body, a plurality of staples removably stored within the staple cavities, and a staple cartridge retainer removable from the cartridge body prior to firing the staple cartridge assembly. The staple cartridge retainer comprises a rib configured to be received within the longitudinal slot, a body portion, and an RFID tag embedded within the body portion, wherein the RFID tag comprises a memory, wherein the memory comprises identifier information stored in the memory specific to the staple cartridge, and wherein the identifier information is accessible by the RFID reader.

Example 2—The surgical stapling system of Example 1, wherein the control circuit is configured to modify a motor control program according to the identifier information.

Example 3—The surgical stapling system of Examples 1 or 2, wherein the instrument interface comprises a handle housing.

Example 4—The surgical stapling system of Examples 1, 2, or 3, wherein staple cartridge retainer comprises a distal end, and wherein the RFID tag is embedded within the distal end.

Example 5—The surgical stapling system of Examples 1, 2, 3, or 4, wherein the staple cartridge retainer comprises a proximal end, and wherein the RFID tag is embedded within the proximal end.

Example 6—The surgical stapling system of Examples 1, 2, 3, 4, or 5, wherein the handle housing comprises an aperture defined therein configured to receive a portion of the staple cartridge retainer therein to read the RFID tag with the RFID reader.

Example 7—The surgical stapling system of Examples 1, 2, 3, 4, 5, or 6, wherein the RFID tag cannot be read by the RFID reader if the staple cartridge retainer is attached to the cartridge body.

Example 8—The surgical stapling system of Examples 1, 2, 3, 4, 5, 6, or 7, wherein the control circuit is configured to alert a user of a validity status of the staple cartridge assembly installed within the cartridge channel upon reading the RFID tag with the RFID reader.

Example 9—A staple cartridge assembly comprising a staple cartridge comprising a cartridge body, a longitudinal slot defined in the cartridge body configured to receive a firing member of a surgical instrument therethrough, a plurality of staple cavities defined in the cartridge body, and a plurality of staples removably stored within the staple cavities, wherein the staples are configured to be deployed by the surgical instrument. The staple cartridge assembly further comprises a staple cartridge retainer configured to hold the staples within the staple cartridge prior to firing the staple cartridge and during the installation of the staple cartridge into the surgical instrument. The staple cartridge retainer comprises a rib configured to be received within the longitudinal slot, a body portion, and an RFID tag embedded within the body portion, wherein the RFID tag comprises a memory, wherein the memory comprises data stored in the memory specific to the staple cartridge assembly, and wherein the data is accessible by an RFID reader of a surgical instrument handle.

Example 10—The staple cartridge assembly of Example 9, wherein the RFID tag comprises a writable RFID tag.

Example 11—The staple cartridge assembly of Examples 9 or 10, wherein the staple cartridge retainer comprises a proximal end, and wherein the RFID tag is embedded within the staple cartridge retainer within the proximal end.

Example 12—A staple cartridge assembly comprising a staple cartridge comprising a cartridge body comprising a cartridge nose, a longitudinal slot defined in the cartridge body, a plurality of staple cavities defined in the cartridge body, and a plurality of staples removably stored within the staple cavities. The staple cartridge assembly further comprises a staple retainer configured to hold the staples within the staple cartridge prior to firing the staple cartridge and during the installation of the staple cartridge in a cartridge channel. The staple retainer comprises a rib removably received within the longitudinal slot and a pry tool portion configured to engage the cartridge nose to pry the cartridge body out of the cartridge channel. The pry tool portion comprises a locking feature configured to be inserted into the longitudinal slot during the removal of the cartridge body out of the cartridge channel, wherein the locking feature is configured to be locked within the cartridge body such that the staple retainer remains connected to the cartridge body after the cartridge body is removed from the cartridge channel to prevent reuse of the staple cartridge assembly.

Example 13—The staple cartridge assembly of Example 12, wherein the pry tool portion comprises a foot portion configured to be inserted through the longitudinal slot to engage the cartridge channel.

Example 14—The staple cartridge assembly of Example 13, wherein the foot portion comprises a lateral width greater than a lateral width of the longitudinal slot.

Example 15—The staple cartridge assembly of Examples 12, 13, or 14, wherein the staple retainer is snap fit around the cartridge body prior to removal.

Example 16—A staple cartridge assembly comprising a staple cartridge comprising a cartridge body, a longitudinal slot defined in the cartridge body, a plurality of staple cavities defined in the cartridge body, and a plurality of staples removably stored within the staple cavities. The staple cartridge assembly further comprises a staple retainer configured to hold the staples within the staple cartridge prior to firing the staple cartridge and during the installation of the staple cartridge in a cartridge channel. The staple retainer comprises arms configured to hold the staple retainer to the cartridge body prior to removal and features detectable by an instrument interface, wherein a unique profile of the features represents information specific to the staple cartridge.

Example 17—The staple cartridge assembly of Example 16, wherein the features comprise tabs extending from a proximal end of the staple retainer.

Example 18—The staple cartridge assembly of Examples 16 or 17, wherein the features are configured to engage switches positioned within a surgical instrument handle housing.

Many of the surgical instrument systems described herein are motivated by an electric motor; however, the surgical instrument systems described herein can be motivated in any suitable manner. In various instances, the surgical instrument systems described herein can be motivated by a manually-operated trigger, for example. In certain instances, the motors disclosed herein may comprise a portion or portions of a robotically controlled system. Moreover, any of the end effectors and/or tool assemblies disclosed herein can be utilized with a robotic surgical instrument system. U.S. patent application Ser. No. 13/118,241, entitled SURGICAL STAPLING INSTRUMENTS WITH ROTATABLE STAPLE DEPLOYMENT ARRANGEMENTS, now U.S. Pat. No. 9,072,535, for example, discloses several examples of a robotic surgical instrument system in greater detail and is incorporated by reference herein in its entirety.

The surgical instrument systems described herein have been described in connection with the deployment and deformation of staples; however, the embodiments described herein are not so limited. Various embodiments are envisioned which deploy fasteners other than staples, such as clamps or tacks, for example. Moreover, various embodiments are envisioned which utilize any suitable means for sealing tissue. For instance, an end effector in accordance with various embodiments can comprise electrodes configured to heat and seal the tissue. Also, for instance, an end effector in accordance with certain embodiments can apply vibrational energy to seal the tissue.

Various embodiments described herein are described in the context of linear end effectors and/or linear fastener cartridges. Such embodiments, and the teachings thereof, can be applied to non-linear end effectors and/or non-linear fastener cartridges, such as, for example, circular and/or contoured end effectors. For example, various end effectors, including non-linear end effectors, are disclosed in U.S. patent application Ser. No. 13/036,647, filed Feb. 28, 2011, entitled SURGICAL STAPLING INSTRUMENT, now U.S. Patent Application Publication No. 2011/0226837, now U.S. Pat. No. 8,561,870, which is hereby incorporated by reference in its entirety. Additionally, U.S. patent application Ser. No. 12/893,461, filed Sep. 29, 2012, entitled STAPLE CARTRIDGE, now U.S. Patent Application Publication No. 2012/0074198, is hereby incorporated by reference in its entirety. U.S. patent application Ser. No. 12/031,873, filed Feb. 15, 2008, entitled END EFFECTORS FOR A SURGICAL CUTTING AND STAPLING INSTRUMENT, now U.S. Pat. No. 7,980,443, is also hereby incorporated by reference in its entirety. U.S. Pat. No. 8,393,514, entitled SELECTIVELY ORIENTABLE IMPLANTABLE FASTENER CARTRIDGE, which issued on Mar. 12, 2013, is also hereby incorporated by reference in its entirety.

The entire disclosures of:

U.S. Pat. No. 5,403,312, entitled ELECTROSURGICAL HEMOSTATIC DEVICE, which issued on Apr. 4, 1995;

U.S. Pat. No. 7,000,818, entitled SURGICAL STAPLING INSTRUMENT HAVING SEPARATE DISTINCT CLOSING AND FIRING SYSTEMS, which issued on Feb. 21, 2006;

U.S. Pat. No. 7,422,139, entitled MOTOR-DRIVEN SURGICAL CUTTING AND FASTENING INSTRUMENT WITH TACTILE POSITION FEEDBACK, which issued on Sep. 9, 2008;

U.S. Pat. No. 7,464,849, entitled ELECTRO-MECHANICAL SURGICAL INSTRUMENT WITH CLOSURE SYSTEM AND ANVIL ALIGNMENT COMPONENTS, which issued on Dec. 16, 2008;

U.S. Pat. No. 7,670,334, entitled SURGICAL INSTRUMENT HAVING AN ARTICULATING END EFFECTOR, which issued on Mar. 2, 2010;

U.S. Pat. No. 7,753,245, entitled SURGICAL STAPLING INSTRUMENTS, which issued on Jul. 13, 2010;

U.S. Pat. No. 8,393,514, entitled SELECTIVELY ORIENTABLE IMPLANTABLE FASTENER CARTRIDGE, which issued on Mar. 12, 2013;

U.S. patent application Ser. No. 11/343,803, entitled SURGICAL INSTRUMENT HAVING RECORDING CAPABILITIES, now U.S. Pat. No. 7,845,537;

U.S. patent application Ser. No. 12/031,573, entitled SURGICAL CUTTING AND FASTENING INSTRUMENT HAVING RF ELECTRODES, filed Feb. 14, 2008;

U.S. patent application Ser. No. 12/031,873, entitled END EFFECTORS FOR A SURGICAL CUTTING AND STAPLING INSTRUMENT, filed Feb. 15, 2008, now U.S. Pat. No. 7,980,443;

U.S. patent application Ser. No. 12/235,782, entitled MOTOR-DRIVEN SURGICAL CUTTING INSTRUMENT, now U.S. Pat. No. 8,210,411;

U.S. patent application Ser. No. 12/235,972, entitled MOTORIZED SURGICAL INSTRUMENT, now U.S. Pat. No. 9,050,083.

U.S. patent application Ser. No. 12/249,117, entitled POWERED SURGICAL CUTTING AND STAPLING APPARATUS WITH MANUALLY RETRACTABLE FIRING SYSTEM, now U.S. Pat. No. 8,608,045;

U.S. patent application Ser. No. 12/647,100, entitled MOTOR-DRIVEN SURGICAL CUTTING INSTRUMENT WITH ELECTRIC ACTUATOR DIRECTIONAL CONTROL ASSEMBLY, filed Dec. 24, 2009, now U.S. Pat. No. 8,220,688;

U.S. patent application Ser. No. 12/893,461, entitled STAPLE CARTRIDGE, filed Sep. 29, 2012, now U.S. Pat. No. 8,733,613;

U.S. patent application Ser. No. 13/036,647, entitled SURGICAL STAPLING INSTRUMENT, filed Feb. 28, 2011, now U.S. Pat. No. 8,561,870;

U.S. patent application Ser. No. 13/118,241, entitled SURGICAL STAPLING INSTRUMENTS WITH ROTATABLE STAPLE DEPLOYMENT ARRANGEMENTS, now U.S. Pat. No. 9,072,535;

U.S. patent application Ser. No. 13/524,049, entitled ARTICULATABLE SURGICAL INSTRUMENT COMPRISING A FIRING DRIVE, filed on Jun. 15, 2012, now U.S. Pat. No. 9,101,358;

U.S. patent application Ser. No. 13/800,025, entitled STAPLE CARTRIDGE TISSUE THICKNESS SENSOR SYSTEM, filed on Mar. 13, 2013, now U.S. Pat. No. 9,345,481;

U.S. patent application Ser. No. 13/800,067, entitled STAPLE CARTRIDGE TISSUE THICKNESS SENSOR SYSTEM, filed on Mar. 13, 2013, now U.S. Patent Application Publication No. 2014/0263552;

U.S. Patent Application Publication No. 2007/0175955, entitled SURGICAL CUTTING AND FASTENING INSTRUMENT WITH CLOSURE TRIGGER LOCKING MECHANISM, filed Jan. 31, 2006; and U.S. Patent Application Publication No. 2010/0264194, entitled SURGICAL STAPLING INSTRUMENT WITH AN ARTICULATABLE END EFFECTOR, filed Apr. 22, 2010, now U.S. Pat. No. 8,308,040, are hereby incorporated by reference herein.

While several forms have been illustrated and described, it is not the intention of Applicant to restrict or limit the scope of the appended claims to such detail. Numerous modifications, variations, changes, substitutions, combinations, and equivalents to those forms may be implemented and will occur to those skilled in the art without departing from the scope of the present disclosure. Moreover, the structure of each element associated with the described forms can be alternatively described as a means for providing the function performed by the element. Also, where materials are disclosed for certain components, other materials may be used. It is therefore to be understood that the foregoing description and the appended claims are intended to cover all such modifications, combinations, and variations as falling within the scope of the disclosed forms. The appended claims are intended to cover all such modifications, variations, changes, substitutions, modifications, and equivalents.

The foregoing detailed description has set forth various forms of the devices and/or processes via the use of block diagrams, flowcharts, and/or examples. Insofar as such block diagrams, flowcharts, and/or examples contain one or more functions and/or operations, it will be understood by those within the art that each function and/or operation within such block diagrams, flowcharts, and/or examples can be implemented, individually and/or collectively, by a wide range of hardware, software, firmware, or virtually any combination thereof. Those skilled in the art will recognize that some aspects of the forms disclosed herein, in whole or in part, can be equivalently implemented in integrated circuits, as one or more computer programs running on one or more computers (e.g., as one or more programs running on one or more computer systems), as one or more programs running on one or more processors (e.g., as one or more programs running on one or more microprocessors), as firmware, or as virtually any combination thereof, and that designing the circuitry and/or writing the code for the software and or firmware would be well within the skill of one of skill in the art in light of this disclosure. In addition, those skilled in the art will appreciate that the mechanisms of the subject matter described herein are capable of being distributed as one or more program products in a variety of forms, and that an illustrative form of the subject matter described herein applies regardless of the particular type of signal bearing medium used to actually carry out the distribution.

Instructions used to program logic to perform various disclosed aspects can be stored within a memory in the system, such as dynamic random access memory (DRAM), cache, flash memory, or other storage. Furthermore, the instructions can be distributed via a network or by way of other computer readable media. Thus a machine-readable medium may include any mechanism for storing or transmitting information in a form readable by a machine (e.g., a computer), but is not limited to, floppy diskettes, optical disks, compact disc, read-only memory (CD-ROMs), and magneto-optical disks, read-only memory (ROMs), random access memory (RAM), erasable programmable read-only memory (EPROM), electrically erasable programmable read-only memory (EEPROM), magnetic or optical cards, flash memory, or a tangible, machine-readable storage used in the transmission of information over the Internet via electrical, optical, acoustical or other forms of propagated signals (e.g., carrier waves, infrared signals, digital signals, etc.). Accordingly, the non-transitory computer-readable medium includes any type of tangible machine-readable medium suitable for storing or transmitting electronic instructions or information in a form readable by a machine (e.g., a computer).

As used in any aspect herein, the term "control circuit" may refer to, for example, hardwired circuitry, programmable circuitry (e.g., a computer processor including one or more individual instruction processing cores, processing unit, processor, microcontroller, microcontroller unit, controller, digital signal processor (DSP), programmable logic device (PLD), programmable logic array (PLA), or field programmable gate array (FPGA)), state machine circuitry, firmware that stores instructions executed by programmable circuitry, and any combination thereof. The control circuit may, collectively or individually, be embodied as circuitry that forms part of a larger system, for example, an integrated circuit (IC), an application-specific integrated circuit (ASIC), a system on-chip (SoC), desktop computers, laptop computers, tablet computers, servers, smart phones, etc. Accordingly, as used herein "control circuit" includes, but is not limited to, electrical circuitry having at least one discrete electrical circuit, electrical circuitry having at least one integrated circuit, electrical circuitry having at least one application specific integrated circuit, electrical circuitry forming a general purpose computing device configured by a computer program (e.g., a general purpose computer configured by a computer program which at least partially carries out processes and/or devices described herein, or a microprocessor configured by a computer program which at least partially carries out processes and/or devices described herein), electrical circuitry forming a memory device (e.g., forms of random access memory), and/or electrical circuitry forming a communications device (e.g., a modem, communications switch, or optical-electrical equipment). Those having skill in the art will recognize that the subject matter described herein may be implemented in an analog or digital fashion or some combination thereof.

As used in any aspect herein, the term "logic" may refer to an app, software, firmware and/or circuitry configured to perform any of the aforementioned operations. Software may be embodied as a software package, code, instructions, instruction sets and/or data recorded on non-transitory computer readable storage medium. Firmware may be embodied as code, instructions or instruction sets and/or data that are hard-coded (e.g., nonvolatile) in memory devices.

As used in any aspect herein, the terms "component," "system," "module" and the like can refer to a computer-related entity, either hardware, a combination of hardware and software, software, or software in execution.

As used in any aspect herein, an "algorithm" refers to a self-consistent sequence of steps leading to a desired result, where a "step" refers to a manipulation of physical quantities and/or logic states which may, though need not necessarily, take the form of electrical or magnetic signals capable of being stored, transferred, combined, compared, and otherwise manipulated. It is common usage to refer to these signals as bits, values, elements, symbols, characters, terms, numbers, or the like. These and similar terms may be associated with the appropriate physical quantities and are merely convenient labels applied to these quantities and/or states.

A network may include a packet switched network. The communication devices may be capable of communicating with each other using a selected packet switched network communications protocol. One example communications protocol may include an Ethernet communications protocol which may be capable permitting communication using a Transmission Control Protocol/Internet Protocol (TCP/IP). The Ethernet protocol may comply or be compatible with the Ethernet standard published by the Institute of Electrical and Electronics Engineers (IEEE) titled "IEEE 802.3 Standard", published in December 2008 and/or later versions of this standard. Alternatively or additionally, the communication devices may be capable of communicating with each other using an X.25 communications protocol. The X.25 communications protocol may comply or be compatible with a standard promulgated by the International Telecommunication Union-Telecommunication Standardization Sector (ITU-T). Alternatively or additionally, the communication devices may be capable of communicating with each other using a frame relay communications protocol. The frame relay communications protocol may comply or be compatible with a standard promulgated by Consultative Committee for International Telegraph and Telephone (CCITT) and/or the American National Standards Institute (ANSI). Alternatively or additionally, the transceivers may be capable of communicating with each other using an Asynchronous Transfer Mode (ATM) communications protocol. The ATM communications protocol may comply or be compatible with an ATM standard published by the ATM Forum titled "ATM-MPLS Network Interworking 2.0" published August 2001, and/or later versions of this standard. Of course, different and/or after-developed connection-oriented network communication protocols are equally contemplated herein.

Unless specifically stated otherwise as apparent from the foregoing disclosure, it is appreciated that, throughout the foregoing disclosure, discussions using terms such as "processing," "computing," "calculating," "determining," "displaying," or the like, refer to the action and processes of a computer system, or similar electronic computing device, that manipulates and transforms data represented as physical (electronic) quantities within the computer system's registers and memories into other data similarly represented as physical quantities within the computer system memories or registers or other such information storage, transmission or display devices.

One or more components may be referred to herein as "configured to," "configurable to," "operable/operative to," "adapted/adaptable," "able to," "conformable/conformed to," etc. Those skilled in the art will recognize that "configured to" can generally encompass active-state components and/or inactive-state components and/or standby-state components, unless context requires otherwise.

The terms "proximal" and "distal" are used herein with reference to a clinician manipulating the handle portion of the surgical instrument. The term "proximal" refers to the portion closest to the clinician and the term "distal" refers to the portion located away from the clinician. It will be further appreciated that, for convenience and clarity, spatial terms such as "vertical", "horizontal", "up", and "down" may be used herein with respect to the drawings. However, surgical instruments are used in many orientations and positions, and these terms are not intended to be limiting and/or absolute. Those skilled in the art will recognize that, in general, terms used herein, and especially in the appended claims (e.g., bodies of the appended claims) are generally intended as "open" terms (e.g., the term "including" should be interpreted as "including but not limited to," the term "having" should be interpreted as "having at least," the term "includes" should be interpreted as "includes but is not limited to," etc.). It will be further understood by those within the art that if a specific number of an introduced claim recitation is intended, such an intent will be explicitly recited in the claim, and in the absence of such recitation no such intent is present. For example, as an aid to understanding, the following appended claims may contain usage of the introductory phrases "at least one" and "one or more" to introduce claim recitations. However, the use of such phrases should not be construed to imply that the introduction of a claim recitation by the indefinite articles "a" or "an" limits any particular claim containing such introduced claim recitation to claims containing only one such recitation, even when the same claim includes the introductory phrases "one or more" or "at least one" and indefinite articles such as "a" or "an" (e.g., "a" and/or "an" should typically be interpreted to mean "at least one" or "one or more"); the same holds true for the use of definite articles used to introduce claim recitations.

In addition, even if a specific number of an introduced claim recitation is explicitly recited, those skilled in the art will recognize that such recitation should typically be interpreted to mean at least the recited number (e.g., the bare recitation of "two recitations," without other modifiers, typically means at least two recitations, or two or more recitations). Furthermore, in those instances where a convention analogous to "at least one of A, B, and C, etc." is used, in general such a construction is intended in the sense one having skill in the art would understand the convention (e.g., "a system having at least one of A, B, and C" would include but not be limited to systems that have A alone, B alone, C alone, A and B together, A and C together, B and C together, and/or A, B, and C together, etc.). In those instances where a convention analogous to "at least one of A, B, or C, etc." is used, in general such a construction is intended in the sense one having skill in the art would understand the convention (e.g., "a system having at least one of A, B, or C" would include but not be limited to systems that have A alone, B alone, C alone, A and B together, A and C together, B and C together, and/or A, B, and C together, etc.). It will be further understood by those within the art that typically a disjunctive word and/or phrase presenting two or more alternative terms, whether in the description, claims, or drawings, should be understood to contemplate the possibilities of including one of the terms, either of the terms, or both terms unless context dictates otherwise. For example, the phrase "A or B" will be typically understood to include the possibilities of "A" or "B" or "A and B."

With respect to the appended claims, those skilled in the art will appreciate that recited operations therein may generally be performed in any order. Also, although various operational flow diagrams are presented in a sequence(s), it should be understood that the various operations may be performed in other orders than those which are illustrated, or may be performed concurrently. Examples of such alternate orderings may include overlapping, interleaved, interrupted, reordered, incremental, preparatory, supplemental, simultaneous, reverse, or other variant orderings, unless context dictates otherwise. Furthermore, terms like "responsive to," "related to," or other past-tense adjectives are generally not intended to exclude such variants, unless context dictates otherwise.

It is worthy to note that any reference to "one aspect," "an aspect," "an exemplification," "one exemplification," and the like means that a particular feature, structure, or characteristic described in connection with the aspect is included in at least one aspect. Thus, appearances of the phrases "in one aspect," "in an aspect," "in an exemplification," and "in one exemplification" in various places throughout the specification are not necessarily all referring to the same aspect. Furthermore, the particular features, structures or characteristics may be combined in any suitable manner in one or more aspects.

Any patent application, patent, non-patent publication, or other disclosure material referred to in this specification and/or listed in any Application Data Sheet is incorporated by reference herein, to the extent that the incorporated materials is not inconsistent herewith. As such, and to the extent necessary, the disclosure as explicitly set forth herein supersedes any conflicting material incorporated herein by reference. Any material, or portion thereof, that is said to be incorporated by reference herein, but which conflicts with existing definitions, statements, or other disclosure material set forth herein will only be incorporated to the extent that no conflict arises between that incorporated material and the existing disclosure material.

In summary, numerous benefits have been described which result from employing the concepts described herein. The foregoing description of the one or more forms has been presented for purposes of illustration and description. It is not intended to be exhaustive or limiting to the precise form disclosed. Modifications or variations are possible in light of the above teachings. The one or more forms were chosen and described in order to illustrate principles and practical application to thereby enable one of ordinary skill in the art to utilize the various forms and with various modifications as are suited to the particular use contemplated. It is intended that the claims submitted herewith define the overall scope.

What is claimed is:

1. A surgical stapling system, comprising:
an instrument interface, comprising:
    a control circuit; and
    an RFID reader;
a shaft assembly attachable to and detachable from said instrument interface, wherein said shaft assembly comprises:
    a shaft; and
    an end effector, comprising:
        a first jaw;
        a second jaw movable relative to said first jaw;
        an anvil; and
        a cartridge channel; and
a replaceable staple cartridge assembly removably positioned within said cartridge channel, wherein said replaceable staple cartridge assembly comprises:
    a cartridge body;
    a longitudinal slot;
    a plurality of staple cavities defined in said cartridge body;
    a plurality of staples removably stored within said staple cavities; and
    a staple cartridge retainer removable from said cartridge body prior to firing said staple cartridge assembly, comprising:
        a rib configured to be received within said longitudinal slot;
        a body portion; and
        an RFID tag embedded within said body portion, wherein said RFID tag comprises a memory, wherein said memory comprises identifier information stored in said memory specific to said staple cartridge, and wherein said identifier information is accessible by said RFID reader.

2. The surgical stapling system of claim 1, wherein said control circuit is configured to modify a motor control program according to said identifier information.

3. The surgical stapling system of claim 1, wherein said instrument interface comprises a handle housing.

4. The surgical stapling system of claim 1, wherein said staple cartridge retainer comprises a distal end, and wherein said RFID tag is embedded within said distal end.

5. The surgical stapling system of claim 1, wherein said staple cartridge retainer comprises a proximal end, and wherein said RFID tag is embedded within said proximal end.

6. The surgical stapling system of claim 5, wherein said handle housing comprises an aperture defined therein configured to receive a portion of said staple cartridge retainer therein to read said RFID tag with said RFID reader.

7. The surgical stapling system of claim 6, wherein said RFID tag cannot be read by said RFID reader if said staple cartridge retainer is attached to said cartridge body.

8. The surgical stapling system of claim 1, wherein said control circuit is configured to alert a user of a validity status of said staple cartridge assembly installed within said cartridge channel upon reading said RFID tag with said RFID reader.

9. A staple cartridge assembly, comprising:
a staple cartridge, comprising:
    a cartridge body;
    a longitudinal slot defined in said cartridge body configured to receive a firing member of a surgical instrument therethrough;
    a plurality of staple cavities defined in said cartridge body; and
    a plurality of staples removably stored within said staple cavities, wherein said staples are configured to be deployed by the surgical instrument; and
a staple cartridge retainer configured to hold said staples within said staple cartridge prior to firing said staple cartridge and during the installation of said staple cartridge into the surgical instrument, wherein said staple cartridge retainer comprises:
    a rib configured to be received within said longitudinal slot;
    a body portion; and
    an RFID tag embedded within said body portion, wherein said RFID tag comprises a memory, wherein said memory comprises data stored in said memory specific to said staple cartridge assembly, and wherein said data is accessible by an RFID reader of a surgical instrument handle.

10. The staple cartridge assembly of claim 9, wherein said RFID tag comprises a writable RFID tag.

11. The staple cartridge assembly of claim 9, wherein said staple cartridge retainer comprises a proximal end, and wherein said RFID tag is embedded within said staple cartridge retainer within said proximal end.

* * * * *